United States Patent
Fisher et al.

(10) Patent No.: US 10,327,996 B2
(45) Date of Patent: Jun. 25, 2019

(54) UNIT DOSE DISPENSING MECHANISMS

(71) Applicant: Omnicell, Inc., Mountain View, CA (US)

(72) Inventors: Herbert Lawson Fisher, Portola Valley, CA (US); Gerardo Moreno, Pleasanton, CA (US)

(73) Assignee: Omnicell, Inc., Mountain View, CA (US)

( * ) Notice: Subject to any disclaimer, the term of this patent is extended or adjusted under 35 U.S.C. 154(b) by 0 days.

(21) Appl. No.: 15/729,355

(22) Filed: Oct. 10, 2017

(65) Prior Publication Data

US 2019/0060178 A1 Feb. 28, 2019

Related U.S. Application Data

(62) Division of application No. 15/693,276, filed on Aug. 31, 2017.

(51) Int. Cl.
*A61J 7/04* (2006.01)
*B65D 83/04* (2006.01)
(Continued)

(52) U.S. Cl.
CPC ........... *A61J 7/0445* (2015.05); *A61F 15/001* (2013.01); *A61J 1/065* (2013.01); *A61J 7/0076* (2013.01);
(Continued)

(58) Field of Classification Search
CPC ........ A61J 7/0445; A61J 1/065; A61J 7/0076; A61J 7/0481; A61J 2200/70;
(Continued)

(56) References Cited

U.S. PATENT DOCUMENTS 3,258,109 A 6/1966 Brettenstein et al.
3,258,153 A 6/1966 Morgan
(Continued)

FOREIGN PATENT DOCUMENTS

| JP | 2014204744 | 10/2014 |
| WO | 2014145413 | 9/2014 |
| WO | 2016137961 | 9/2016 |

OTHER PUBLICATIONS

U.S. Appl. No. 14/634,063, Final Office Action, dated Mar. 31, 2017, 10 pages.
(Continued)

*Primary Examiner* — Rakesh Kumar
(74) *Attorney, Agent, or Firm* — Kilpatrick Townsend & Stockton LLP

(57) ABSTRACT

Mechanisms for dispensing items such as medications and medical supplies. Different mechanisms may be tailored to dispensing different kinds of items, for example medications in single dose packages, vials, syringes, or other similarly-shaped items. The dispensers may be placed in a dispensing unit that includes a lockable restock drawer and a dispense drawer into which items are dispensed by the dispensing mechanisms. The various kinds of dispensing mechanisms may be installed in the restock drawer in any workable proportion and arrangement. The dispensing mechanisms include multiple sensing technologies for tracking and inventory of items and for accurate sensing of items as they are dispensed.

7 Claims, 44 Drawing Sheets

(51) Int. Cl.
*A61J 7/00* (2006.01)
*A61F 15/00* (2006.01)
*G07F 17/00* (2006.01)
*A61J 1/06* (2006.01)

(52) U.S. Cl.
CPC ........ *A61J 7/0481* (2013.01); *B65D 83/0409* (2013.01); *B65D 83/0445* (2013.01); *B65D 83/0454* (2013.01); *G07F 17/0092* (2013.01); *A61J 2200/70* (2013.01)

(58) Field of Classification Search
CPC ............ B65D 83/0409; B65D 83/0445; B65D 83/0454; A61F 15/001
USPC ...................................................... 221/12, 2
See application file for complete search history.

(56) References Cited

U.S. PATENT DOCUMENTS

| | | | |
|---|---|---|---|
| 3,369,697 A | 2/1968 | Glucksman | |
| 3,410,452 A | 11/1968 | Igel | |
| 3,443,509 A | 5/1969 | Sandy | |
| 3,677,437 A * | 7/1972 | Haigler | G06M 7/00 221/7 |
| 3,921,806 A | 11/1975 | Wawracz | |
| 4,266,563 A | 5/1981 | Fujita | |
| 4,310,103 A | 1/1982 | Reilly, Jr. et al. | |
| 4,573,606 A * | 3/1986 | Lewis | A61J 7/0481 221/15 |
| 4,597,091 A | 6/1986 | Blake et al. | |
| 4,597,864 A | 7/1986 | Wiesemann | |
| 4,778,042 A | 10/1988 | Warren et al. | |
| 4,872,591 A | 10/1989 | Konopka | |
| 4,980,292 A * | 12/1990 | Elbert | G01N 35/0092 221/2 |
| 5,148,944 A | 9/1992 | Kaufman | |
| 5,190,185 A | 3/1993 | Blechl | |
| 5,197,632 A | 3/1993 | Kaufman | |
| 5,318,200 A | 6/1994 | Allen et al. | |
| 5,329,459 A | 7/1994 | Kaufman | |
| 5,377,864 A | 1/1995 | Blechl | |
| 5,671,262 A | 9/1997 | Boyer | |
| 5,745,366 A | 4/1998 | Higham et al. | |
| 5,755,357 A | 5/1998 | Orkin | |
| 5,805,455 A | 9/1998 | Lipps | |
| 5,805,456 A | 9/1998 | Higham et al. | |
| 5,905,653 A | 5/1999 | Higham et al. | |
| 5,927,540 A | 7/1999 | Godlewski | |
| 6,004,020 A | 12/1999 | Bartur | |
| 6,011,999 A | 1/2000 | Holmes | |
| 6,039,467 A | 3/2000 | Holmes | |
| 6,151,536 A | 11/2000 | Arnold et al. | |
| 6,170,929 B1 | 1/2001 | Wilson et al. | |
| 6,227,407 B1 | 5/2001 | Simeri et al. | |
| 6,272,394 B1 | 8/2001 | Lipps | |
| 6,385,505 B1 | 5/2002 | Lipps | |
| 6,510,962 B1 | 1/2003 | Lim | |
| 6,581,797 B2 | 6/2003 | McKinney et al. | |
| 6,609,047 B1 | 8/2003 | Lipps | |
| 6,625,952 B1 | 9/2003 | Chudy | |
| 6,640,159 B2 | 10/2003 | Holmes et al. | |
| 6,640,994 B2 | 11/2003 | Chen et al. | |
| 6,760,643 B2 | 7/2004 | Lipps | |
| 6,975,922 B2 | 12/2005 | Duncan et al. | |
| 7,348,884 B2 | 3/2008 | Higham | |
| 7,359,765 B2 | 4/2008 | Varvarelis | |
| 7,383,965 B2 | 6/2008 | Matsumoto et al. | |
| 7,395,946 B2 | 7/2008 | Yuyama | |
| 7,454,880 B1 | 11/2008 | Austin et al. | |
| 7,571,024 B2 | 8/2009 | Duncan et al. | |
| 7,675,421 B2 | 3/2010 | Higham | |
| 7,819,281 B2 | 10/2010 | Guindulain et al. | |
| 7,835,819 B2 | 11/2010 | Duncan et al. | |
| 7,978,564 B2 | 7/2011 | De La Huerga | |
| 8,027,749 B2 | 9/2011 | Vahlberg et al. | |
| 8,073,563 B2 | 12/2011 | Vahlberg et al. | |
| 8,126,590 B2 | 2/2012 | Vahlberg et al. | |
| 8,131,397 B2 | 3/2012 | Vahlberg et al. | |
| 8,140,186 B2 | 3/2012 | Vahlberg et al. | |
| 8,155,786 B2 | 4/2012 | Vahlberg et al. | |
| 8,453,874 B2 | 6/2013 | Simpson | |
| 8,744,621 B2 | 6/2014 | Michael | |
| 8,851,265 B2 | 10/2014 | Morishita et al. | |
| 8,924,227 B2 * | 12/2014 | Fellows | B65G 1/045 705/2 |
| 8,936,175 B1 | 1/2015 | Song | |
| 8,944,281 B2 | 2/2015 | Inoue | |
| 9,113,729 B2 | 8/2015 | Righetti | |
| 9,149,405 B2 | 10/2015 | Braun | |
| 9,492,357 B2 * | 11/2016 | MacVittie | A61J 7/0472 |
| 9,540,177 B1 | 1/2017 | Yasinski | |
| 9,682,016 B1 * | 6/2017 | Balasubramanian | A61J 7/02 |
| 9,818,251 B2 | 11/2017 | Wilson et al. | |
| 2004/0251266 A1 | 12/2004 | Yuyama | |
| 2006/0273106 A1 * | 12/2006 | Kim | B65B 5/103 221/200 |
| 2007/0169437 A1 | 7/2007 | Yuyama | |
| 2008/0319577 A1 | 12/2008 | Vahlberg et al. | |
| 2008/0319579 A1 | 12/2008 | Vahlberg et al. | |
| 2008/0319789 A1 | 12/2008 | Vahlberg et al. | |
| 2008/0319790 A1 | 12/2008 | Vahlberg et al. | |
| 2010/0042437 A1 | 2/2010 | Levy et al. | |
| 2010/0228392 A1 | 9/2010 | Braun | |
| 2012/0029692 A1 * | 2/2012 | Owen | G01V 8/20 700/240 |
| 2012/0123587 A1 | 5/2012 | Mockus et al. | |
| 2012/0248947 A1 | 10/2012 | Kijowski et al. | |
| 2012/0259456 A1 | 10/2012 | Saltsov | |
| 2013/0204432 A1 | 8/2013 | Panetta et al. | |
| 2014/0138398 A1 | 5/2014 | Daniels | |
| 2014/0158705 A1 | 6/2014 | Wid | |
| 2014/0288698 A1 | 9/2014 | Handfield et al. | |
| 2016/0253860 A1 | 9/2016 | Wilson et al. | |
| 2018/0033233 A1 | 2/2018 | Wilson et al. | |

OTHER PUBLICATIONS

U.S. Appl. No. 14/634,063, Final Office Action, dated Jul. 29, 2016, 8 pages.
U.S. Appl. No. 14/634,063, Non-Final Office Action, dated Jan. 6, 2016, 11 pages.
U.S. Appl. No. 14/634,063, Non-Final Office Action, dated Nov. 25, 2016, 11 pages.
U.S. Appl. No. 14/634,063, Notice of Allowance, dated Jul. 13, 2017, 7 pages.
International Patent Application No. PCT/US2016/019082, "Invitation to Pay Add'l Fees and Partial Search Rpt", dated Apr. 18, 2016, 2 pages.
International Patent Application No. PCT/US2016/019082 , "International Search Report and Written Opinion", dated Jul. 26, 2016, 13 pages.
International Patent Application No. PCT/US2016/019082, "International Preliminary Report on Patentability", dated Aug. 29, 2017, 9 pages.
U.S. Appl. No. 15/729,339, Non-Final Office Action dated Mar. 22, 2018, 11 pages.
U.S. Appl. No. 15/729,353 received a Non-Final Office Action dated May 3, 2018, all pages.
U.S. Appl. No. 15/723,707 received a Non-Final Office Action dated May 30, 2018, all pages.
U.S. Appl. No. 15/693,276, received a Non-Final Office Action, dated Jun. 5, 2018, 11 pages.
International Search Report and Written Opinion dated Aug. 30, 2018 for International Patent Application No. PCT/US2018/045124 filed Aug. 3, 2018, all pages.

* cited by examiner

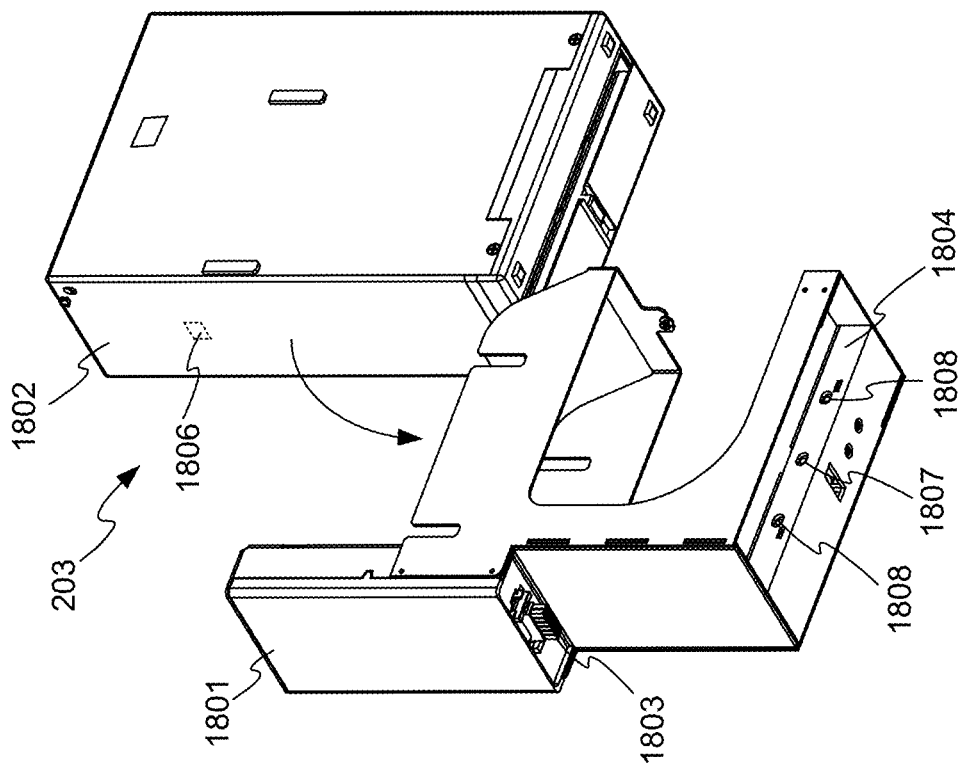
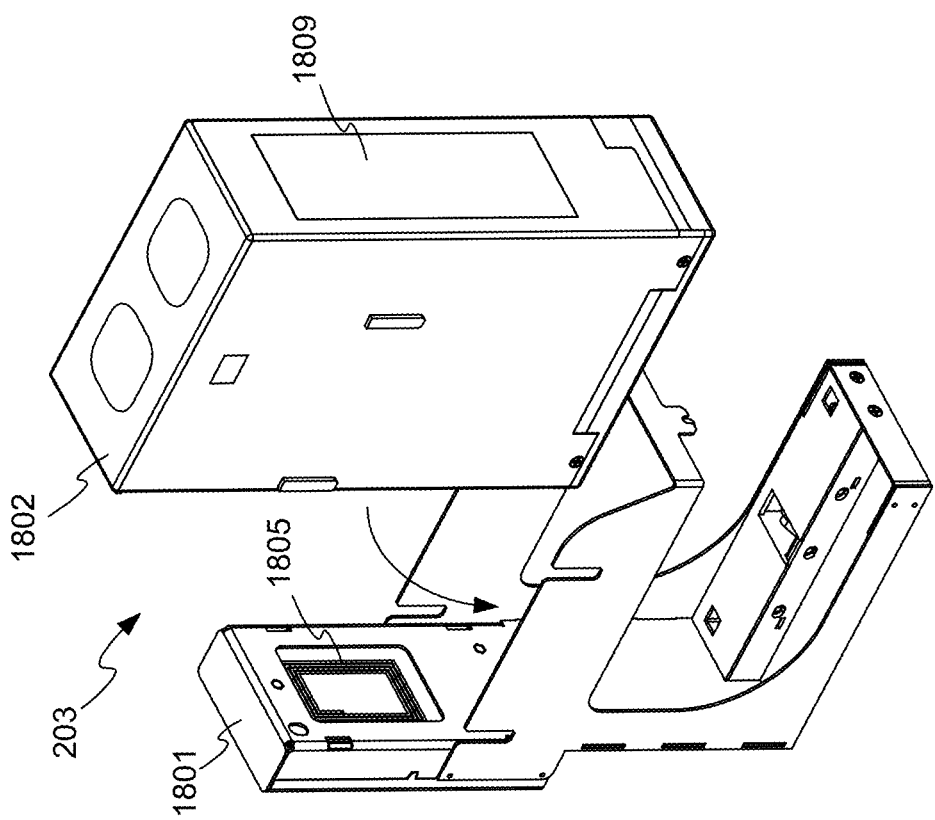
FIG. 18B
FIG. 18A

UNIT DOSE DISPENSING MECHANISMS

CROSS REFERENCE TO RELATED APPLICATIONS

This application is a division of U.S. patent application Ser. No. 15/693,276, filed Aug. 31, 2017 and titled "Unit Dose Dispensing Mechanisms", the entire disclosure of which is hereby incorporated by reference herein for all purposes.

BACKGROUND OF THE INVENTION

Many industries rely on the accurate inventory and dispensing of secure items. For example, in a hospital setting, it is of paramount importance that patients be given the correct medications in the correct doses. In addition, it is legally required that controlled substances be secured and accurately tracked, and it is also important that inventories of medications and supplies be tracked so that proper business controls can be implemented.

Various dispensing cabinets and carts have been developed to assist in the management of medications and other items. However, improvements are still desired in the reliability of dispensing and tracking of items, and it is also desirable to reduce the amount of space required for item storage and dispensing.

BRIEF SUMMARY OF THE INVENTION

According to one aspect, a dispensing mechanism comprises a connector for receiving electrical signals from a cabinet in which the dispensing mechanism is installed, an actuator that operates in response to the electrical signals, a non-circular sprocket driven by the actuator, and a belt driven by the sprocket. The belt comprises a plurality of links, and is configured to circulate within a chamber when driven by the actuator. The dispensing mechanism further comprises a plurality of paddles integrally formed with the links of the belt for receiving between pairs of the paddles items to be dispensed, the paddles extending from the belt. The dispensing mechanism also includes a housing defining the chamber and defining an opening at the bottom of the chamber, such that a single item drops from between its respective paddles and through the opening when the segmented belt is incrementally advanced and the paddle supporting the item approaches a vertical orientation due to the advancement of the belt.

According to another aspect, a dispensing mechanism comprises a set of vertical channels of a shape and size to receive a number of vials and hold the vials in vertical stacks. The dispensing mechanism also includes a connector for receiving electrical signals from a cabinet in which the dispensing mechanism is installed, an actuator that moves in response to the electrical signals, and a plurality of rotatable receivers driven by the actuator. Each of the rotatable receivers is positioned under a respective one of the vertical channels and defines an open-sided cavity of a shape and size to receive a vial. The dispensing mechanism also includes a housing defining opening at the bottom of the dispensing mechanism. When the rotatable receivers are rotated, their respective cavities sequentially align with the vertical channels, such that upon alignment, one of the vials drops into the respective cavity through the open side of the cavity, and when one of the cavities holding a vial approaches a downward vertical orientation, a single vial drops from the open side of the downwardly-oriented cavity and through the opening.

According to another aspect, a dispensing mechanism comprises a connector for receiving electrical signals from a cabinet in which the dispensing mechanism is installed, an actuator that moves in response to the electrical signals, and a housing for storing items to be dispensed. The housing comprises a floor having an opening through which items are to be dispensed, and the housing includes means for feeding items by gravity toward the opening in the floor. The dispensing mechanism further comprises a moveable slide driven by the actuator, the moveable slide having a slot through the movable slide, into which slot items to be dispensed fall one at a time, and a spring that biases the slide into a default position in which the slot of the moveable slide is not aligned with the opening in the floor. When the slide is moved by the actuator, the slide translates against the action of the spring into a position in which the slot in the slide aligns with the opening in the floor, allowing a single item in the slot to fall through the opening to be dispensed.

According to another aspect, a system for detecting items comprises one or more light emitters directed across an opening, and one or more light receivers. Each of the light receivers generates a signal indicating the intensity of light received by the respective light receiver. The system further comprises a dispensing mechanism that contains one or more items to be dispensed, and is configured to cause the items to be dispensed one at a time through the opening. The system also comprises circuitry that compares the outputs of the one or more light receivers with respective reference signals and generates a detection signal based on the result of the comparisons. The detection signal indicates one or more conditions selected from the set of conditions consisting of a) any one or any number of the one or more light receivers is producing an output signal that is below one of the reference signals, and b) any one or any number of the one or more light receivers is producing an output signal that is above one of the reference signals. The system also includes a controller that receives the detection signal. The controller is configured to command the dispensing of an item, monitor the output of the circuitry for a detection signal produced in conjunction with the dispensing of the item, and during a time when no dispensing is required, monitor the output of the circuitry for a detection signal that is not produced in conjunction with the dispensing of any item.

BRIEF DESCRIPTION OF THE DRAWINGS

FIGS. 18A and 18B illustrate upper and lower views of a third dispensing mechanism in accordance with embodiments of the invention.

DETAILED DESCRIPTION OF THE INVENTION

Figure 1:
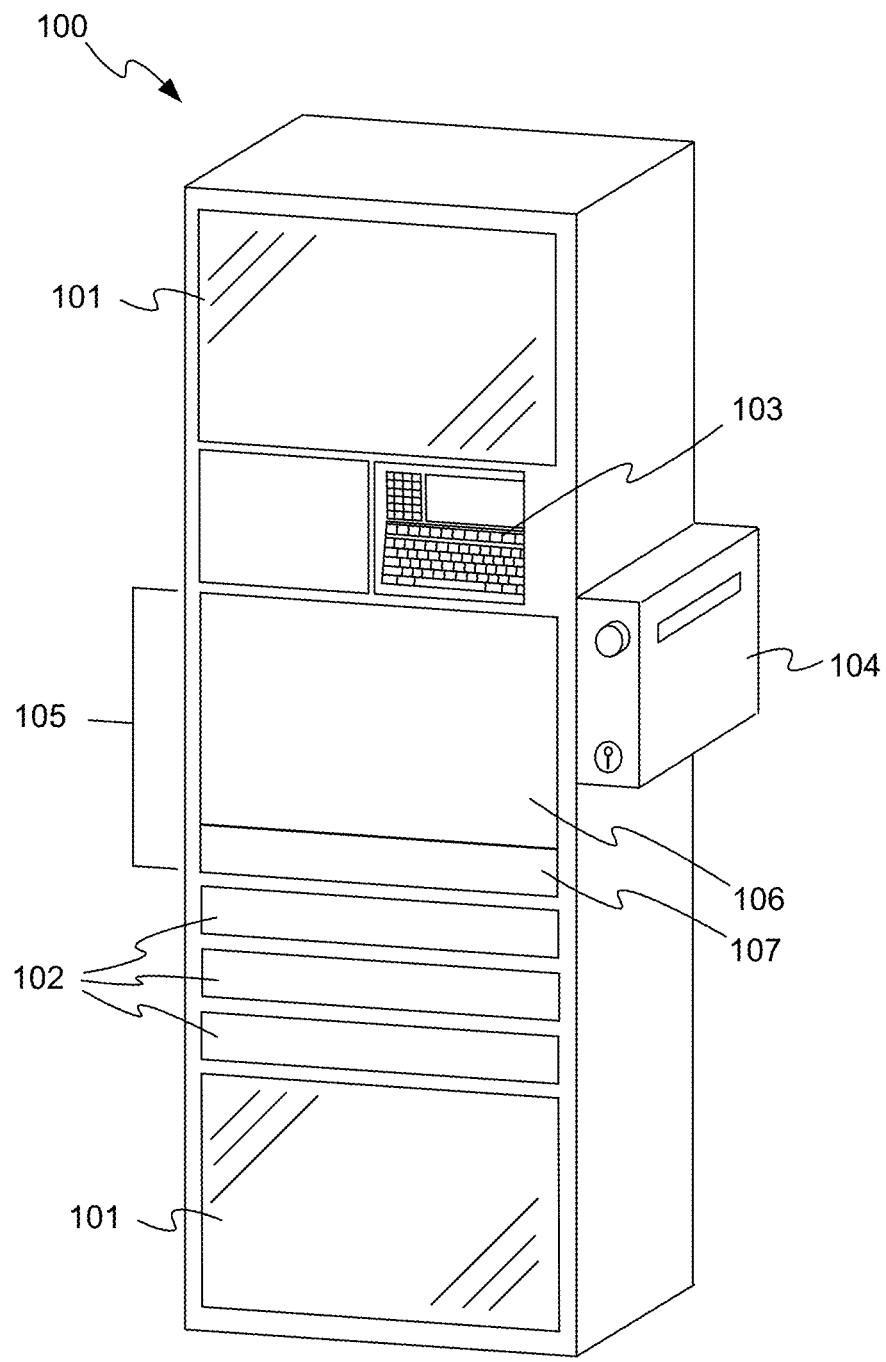
FIG. 1 illustrates an example cabinet in which the invention may be embodied.

FIG. 1 illustrates an example cabinet 100 in which the invention may be embodied. Cabinet 100 includes various doors 101 and drawers 102 providing access to compartments for storing items such as medical supplies or medications. For example, supplies such as bandages, swabs, and the like may be stored in unlocked compartments such as may be accessed through one of doors 101. Medications may be stored in individually lockable compartments within drawers such as drawers 102. A computer 103 maintains records of the contents of cabinet 100, and may control access to individual compartments. For example, a floor nurse needing to obtain a dose of medication for a hospital patient may enter his or her identification and the medication required into computer 103. Computer 103 verifies that the nurse is authorized to remove the medication, and unlocks a particular drawer 102 and a particular compartment within the drawer containing the required medication. Computer 103 may also control lights that guide the nurse to the correct drawer and compartment, to help ensure that the correct medication is dispensed. In addition, computer 103 may communicate with a central computer system that coordinates information from many storage and dispensing devices such as cabinet 100.

While embodiments of the invention are described in the context of stationary cabinet 100, it will be recognized that the invention may be embodied in other kinds of storage devices, for example movable cabinets, carts, storage rooms, and the like. Example dispensing devices are described in the following commonly owned U.S. patents and patent applications, the contents of which are hereby incorporated by reference: U.S. Pat. No. 6,272,394, issued on Aug. 7, 2001 to Lipps, U.S. Pat. No. 6,385,505, issued on May 7, 2002 to Lipps, U.S. Pat. No. 6,760,643, issued on Jul. 6, 2004 to Lipps, U.S. Pat. No. 5,805,455, issued on Sep. 8, 1998 to Lipps, U.S. Pat. No. 6,609,047, issued on Aug. 19, 2003 to Lipps, U.S. Pat. No. 5,805,456, issued on Sep. 8, 1998 to Higham et al., U.S. Pat. No. 5,745,366, issued on Apr. 28, 1998 to Higham et al., an U.S. Pat. No. 5,905,653, issued on May 18, 1999 to Higham et al., U.S. Pat. No. 5,927,540, issued on Jul. 27, 1999 to Godlewski, U.S. Pat. No. 6,039,467, issued on Mar. 21, 2000 to Holmes, U.S. Pat. No. 6,640,159, issued on Oct. 28, 2003 to Holmes et al., U.S. Pat. No. 6,151,536, issued on Nov. 21, 2000 to Arnold et al., U.S. Pat. No. 5,377,864, issued on Jan. 3, 1995 to Blechl et al., U.S. Pat. No. 5,190,185, issued on Mar. 2, 1993 to Blechl, U.S. Pat. No. 6,975,922, issued on Dec. 13, 2005 to Duncan et al., U.S. Pat. No. 7,571,024, issued on Aug. 4, 2009 to Duncan et al., U.S. Pat. No. 7,835,819, issued on Nov. 16, 2010 to Duncan et al., U.S. Pat. No. 6,011,999, issued on Jan. 4, 2000 to Holmes, U.S. Pat. No. 7,348,884, issued on Mar. 25, 2008 to Higham, U.S. Pat. No. 7,675,421, issued on Mar. 9, 2010 to Higham, U.S. Pat. No. 6,170,929, issued on Jan. 9, 2001 to Wilson et al., U.S. Pat. No. 8,155,786 to Vahlberg et al., issued on Apr. 10, 2012, U.S. Pat. No. 8,073,563 to Vahlberg et al., issued on Dec. 6, 2011, U.S. Patent Application Publication No. 2008/0319577 of Vahlberg et al., published on Dec. 25, 2008, U.S. Pat. No. 8,140,186 to Vahlberg et al., issued on Mar. 20, 2012, U.S. Pat. No. 8,126,590 to Vahlberg et al., issued on Feb. 28, 2012, U.S. Pat. No. 8,027,749 to Vahlberg et al., issued on Sep. 27, 2011, U.S. Patent Application Publication No. 2008/0319790 of Vahlberg et al., published on Dec. 25, 2008, U.S. Patent Application Publication No. 2008/0319789 of Vahlberg et al., published on Dec. 25, 2008, U.S. Pat. No. 8,131,397 to Vahlberg et al., issued on Mar. 6, 2012, U.S. Patent Application Publication No. 2008/0319579 of Vahlberg et al., published on Dec. 25, 2008, and U.S. Patent Application Publication No. 2010/0042437 of Levy et al., published on Feb. 18, 2010. Embodiments of the present invention may incorporate features from the devices described in these documents, in any workable combination.

In the above scenario, the nurse may be given access to a compartment having a large number of doses of the medication, and he or she may simply remove the number immediately required.

Cabinet 100 also includes a return bin 104, into which unused items can be placed, for later return to stock by a pharmacy technician.

When further control and tracking accuracy is required, medications may be placed in a dispensing unit such as dispensing unit 105. Dispensing unit 105 includes a restock drawer 106 and a dispense drawer 107. Restock drawer includes in turn a number of dispensing mechanisms (not visible in FIG. 1) that, under control of computer 103, can dispense single items into dispense drawer 107. Dispense drawer 107 can then be opened to retrieve the dispensed items. Restock drawer 106 is accessible only by specially-authorized persons, for example for restocking by a pharmacy technician.

Figure 2:
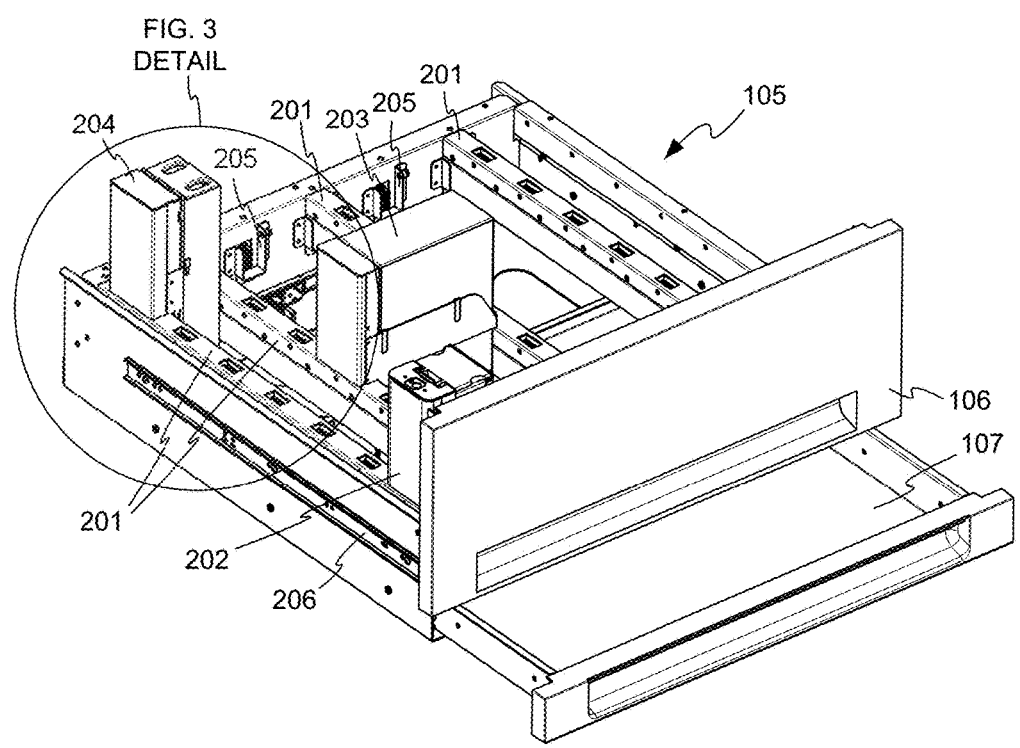
FIG. 2 illustrates a dispensing unit in accordance with embodiments of the invention.

FIG. 2 illustrates dispensing unit 105 in more detail, including restock drawer 106 and dispense drawer 107. A number of dispensing mechanisms may be installed within restock drawer by 106 attaching them to rails 201. Only a few dispensing mechanisms 202, 203, 204 are shown in FIG. 2. Different types of dispensing mechanisms may be present, depending on the kinds of items to be dispensed, as is discussed in more detail below. The different kinds of dispensers may be of differing sizes, and rails 201 may be configured as necessary to accommodate a particular mix of dispensing mechanisms, by fixing rails 201 to different sets of hangers 205.

For example, dispensing mechanism 203 is a double width mechanism, placed between rails that are two bays wide, while dispensing mechanisms 202 and 204 are single width mechanisms, placed between rails 201 that are connected to adjacent sets of hangers 205. Other sizes of dispensers, for example triple and quadruple widths are also possible.

FIG. 2 also illustrates that dispense drawer 107 and restock drawer 106 form a nested pair of drawers. That is, restock drawer 106 can slide out of cabinet 100 on guides 206 for restocking, maintenance, and the like, carrying dispense drawer 107 with restock drawer 106. Similarly, dispense drawer 107 can slide in and out of restock drawer 106 on similar guides not easily visible in FIG. 2.

In some embodiments, dispense drawer 107 may conveniently serve as a work surface for the user of cabinet 100 or a similar device. For example, once an item has been dispensed into dispense drawer 107 and the user has opened dispense drawer 107 to retrieve the item, the user may use the flat bottom of dispense drawer 107 to rest a note pad, computer, or other item he or she may use to document or make notes about the transaction. Dispensing unit 105 may include features to facilitate the use of dispense drawer 107 as a work surface. For example, the guides or other slide mechanism by which dispense drawer opens may include a detent at the openmost position of dispense drawer 107, to lend stability to dispense drawer 107 while it is used as a work surface.

Figure 3:
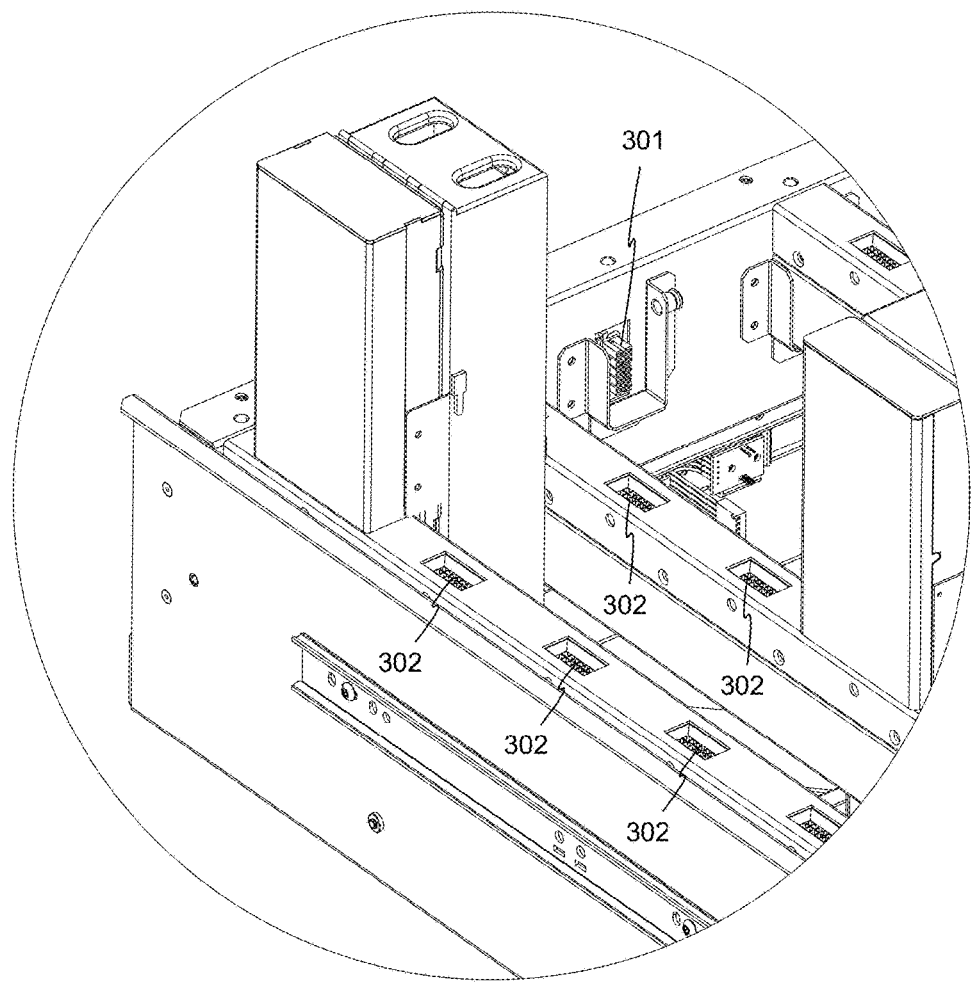
FIG. 3 is a detail view of a portion of FIG. 2.

FIG. 3 is a detail view of a portion of FIG. 2, showing that at each hanger 205 is an electrical connector 301. Each connector 301 connects with a mating connector attached to wiring within a rail 201 positioned at the respective hanger 205, supplying power and signals coming from other systems within cabinet 100. Other connectors 302 are spaced along the rails, for making electrical connections with the dispensing mechanisms such as dispensing mechanisms 202, 203, and 204. To accomplish the required electrical connections, each rail 201 may house a wiring harness, a printed circuit board assembly (PCBA), or the like. Thus, computer 103 can communicate individually with any dispensing mechanism within restock drawer 106. Cabling from all of the connectors converges at a circuit board (not visible) at the back of dispensing unit 105, which in turn connects to other electronics within cabinet 100 via one or more flexible cables (not visible in FIG. 3), which permits dispensing unit 105 to slide out of cabinet 100 for restocking, maintenance, and the like.

Figure 4A:
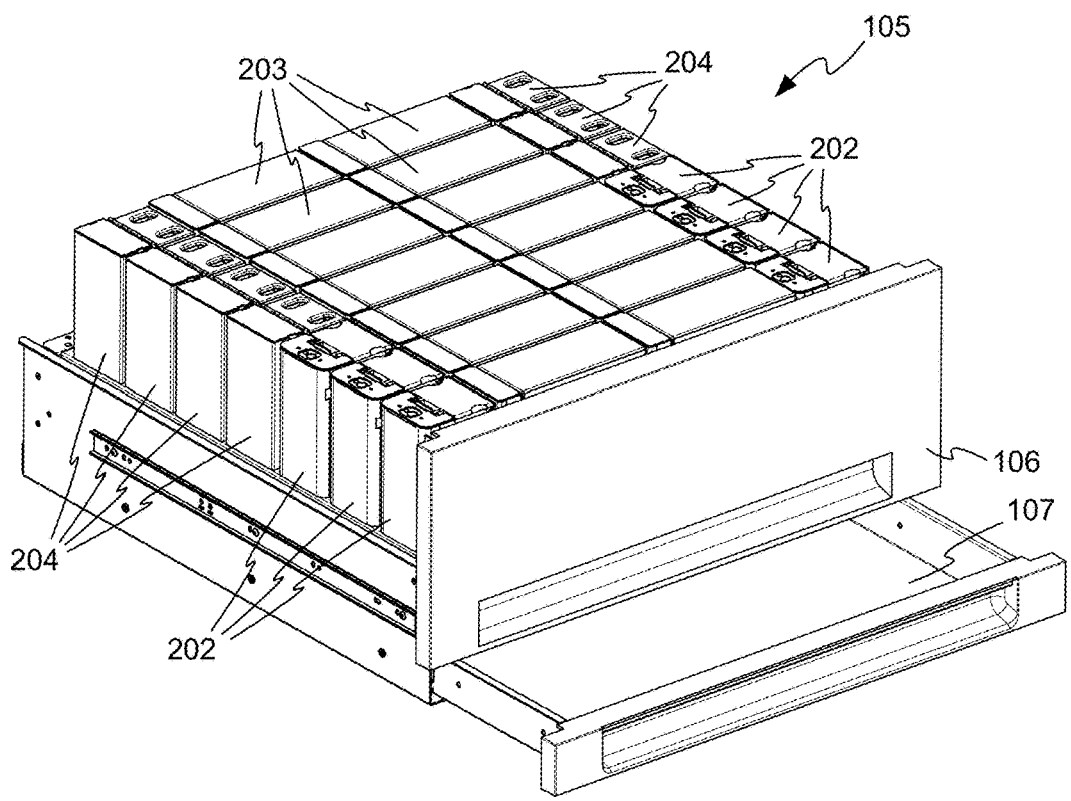
FIG. 4A illustrates the dispensing unit of FIG. 2 fully loaded with dispensing mechanisms.
Figure 4B:
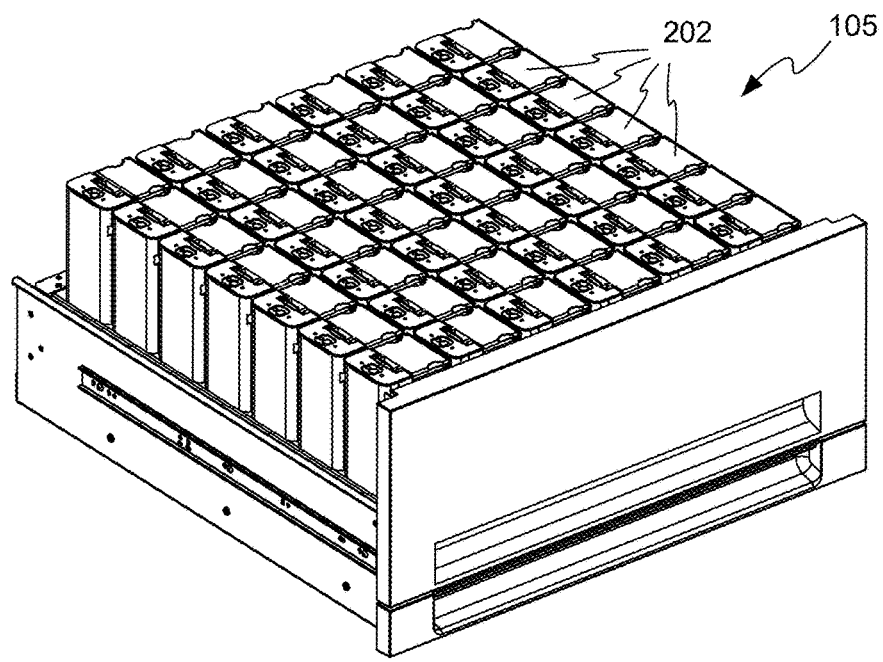
FIG. 4B illustrates the dispensing unit of FIG. 2 fully loaded with a different mix of dispensing mechanisms.

FIG. 4A illustrates dispensing unit 105 fully loaded with seven dispensing mechanisms 202, 14 dispensing mechanisms 203, and seven dispensing mechanisms 204, fully populating the available spaces on rails 201. It will be recognized that this arrangement of dispensing units is but one example of many, many arrangements of dispensing units that could be employed. For example, restock drawer 106 may not be fully populated with dispensing units. Only one or two different kinds of dispensing mechanisms may be present, or four or more kinds of dispensing units may be present. Different kinds of dispensing units may be present in any workable proportions, and like dispensing units need not be installed next to each other. Example dispensing unit 105 can hold up to 42 single width dispensing mechanisms (with two additional rails 201 installed). One example of this is shown in FIG. 4B, in which dispensing unit is loaded with 42 dispensing mechanisms 202.

Preferably, each dispensing unit can identify itself through its respective connector 302, and computer 103 can create a map of the particular arrangement of dispensing units that are installed. Computer 103 can also preferably detect the presence of a dispensing unit at any one of the bay positions, through the respective connector 302 or via a separate sensor. In addition, each dispensing unit can preferably also communicate to computer 103 the kind and quantity of items it contains and stands ready to dispense.

Figure 5:
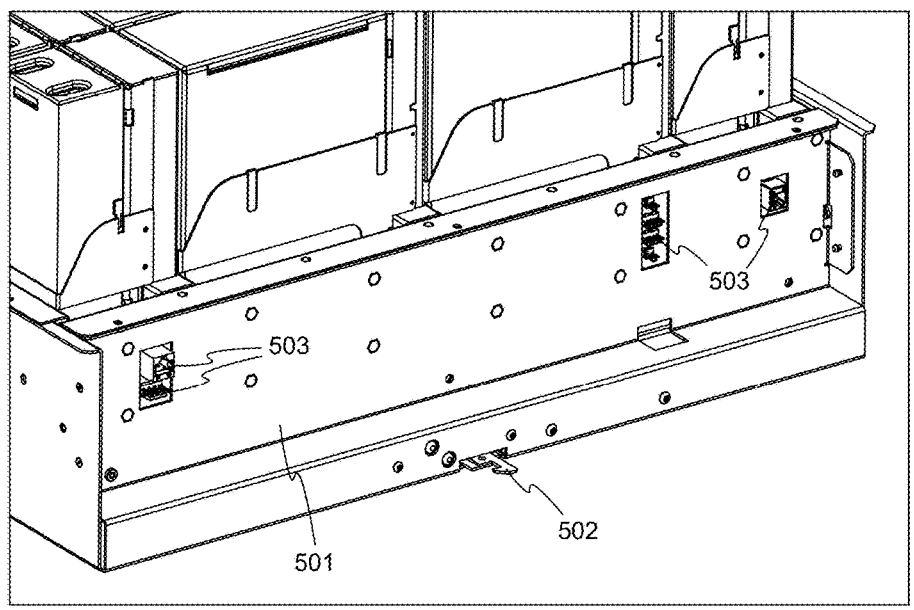
FIG. 5 is a reverse angle view of a portion of the fully-loaded dispensing unit of FIG. 4A.

FIG. 5 is a reverse angle view of a portion of the fully-loaded dispensing unit 105 of FIG. 4A, showing a back panel 501 of restock drawer 106. Preferably, both restock drawer 106 and dispense drawer 107 include latching mechanisms operable by computer 103, to prevent the opening of the drawers at improper times. For example, computer 103 may permit restock drawer 106 to be opened only when computer 103 has received a proper security code from a restocking technician, and may permit dispense drawer 107 to be opened only after an item has been dispensed from one of dispensing mechanisms 202, 203, 204. A latching mechanism 502 for locking and unlocking restock drawer 106 is visible in FIG. 5. A similar latching mechanism may be provided inside restock drawer 106 for locking and unlocking dispense drawer 107. Also visible in FIG. 5 are various connectors 503 for connecting to other electronics within cabinet 100, for example a power supply, computer 103, or other electronic components through one or more flexible cables (not shown).

Dispensing Mechanisms

The dispensing mechanisms 202, 203, 204 may be tailored to the size and type of items to be dispensed, and provide improvements over prior dispensing mechanisms. For example, one prior type of dispensing mechanism used a helical coil, and items to be dispensed were positioned between the coils of the helix. The coil was rotated until an item was advanced beyond the grasp of the coil and was dispensed. This kind of dispenser, although widely and successfully used, is somewhat limited in the shapes and sizes of items that could be dispensed, as the items must be compatible with the pitch and size of the coil.

Dispensing Mechanism for Blister Packs and Other Small Items

Figure 6A:
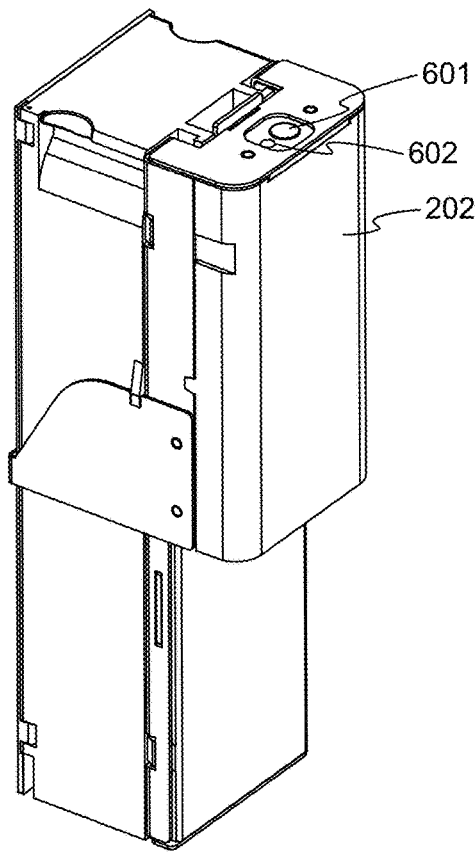
FIGS. 6A and 6B illustrate upper and lower views of a first dispensing mechanism in accordance with embodiments of the invention.
Figure 6B:
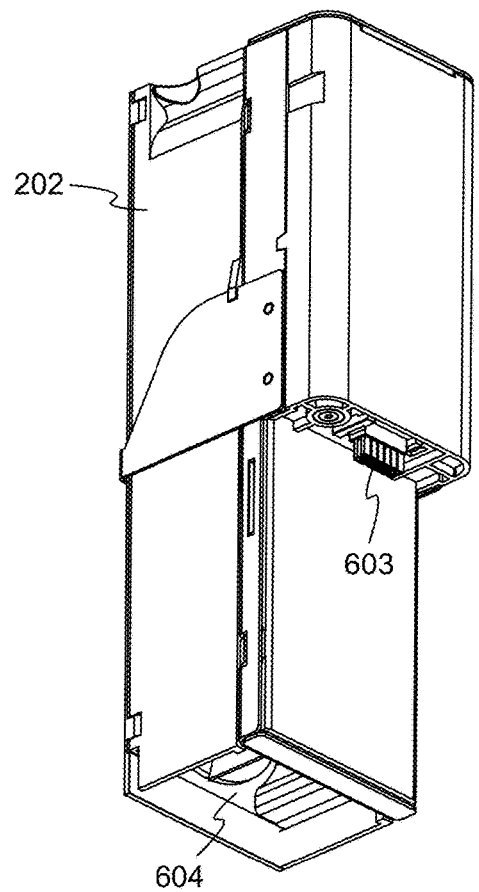

FIGS. 6A and 6B illustrate upper and lower views of dispensing mechanism 202 in more detail. Dispensing mechanism 202 may be especially useful for dispensing small items such as individual medicine doses packaged in well-known "blister packs", although dispensing mechanism 202 may be useful for dispensing may other kinds of items as well.

As is visible in FIG. 6A, a button 601 at the top of dispensing mechanism 202 allows a user authorized to access the interior of restock drawer 106 to signal computer 103, for example to record the fact that dispensing mechanism 202 has been refilled. A light 602 enables computer 103 to communicate to the user, for example flashing the light to direct the user to restock this particular dispensing mechanism.

As is visible in FIG. 6B, a connector 603, compatible with connectors 302 on rails 201, is positioned to engage one of connectors 302 when dispensing mechanism 202 is installed in restock drawer 106. Various parts of dispensing mechanism 202 collectively constitute a housing that defines an opening 604 at the bottom of dispensing mechanism 202, through which items are dispensed. Dispensing mechanism 202 may be removably secured to one of rails 201 using a snap mechanism, one or more screws, or by another method.

Figure 7B:
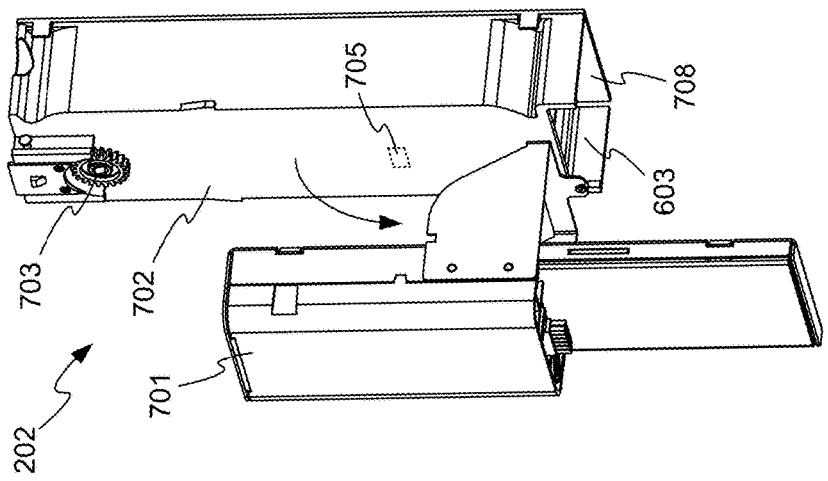
FIGS. 7A and 7B illustrate partially exploded views of the dispensing mechanism of FIGS. 6A and 6B.
Figure 7A:
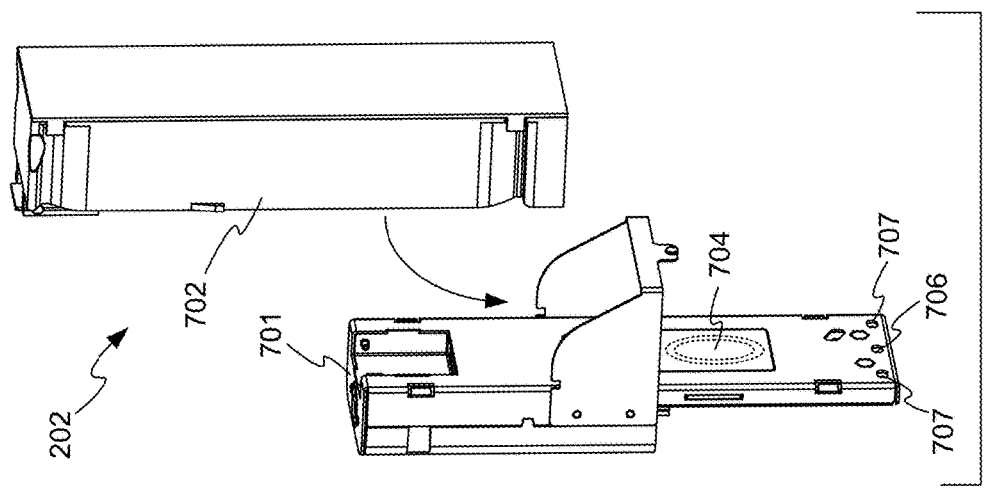

As is shown in FIGS. 7A and 7B, example dispensing mechanism 202 comprises a dispenser 701 and a cassette 702, which are separable. For example, dispenser 701 and cassette 702 may snap together, may be separable with the removal of one or a small number of screws, or may be reasonably separable in some other way without damage to either dispenser 701 or cassette 702. In this way, restocking may be accomplished by replacing a depleted cassette 702 with a full cassette 702. A gear 703 engages a driving gear (not easily visible in FIG. 7A) within dispenser 701 when cassette 702 is assembled to dispenser 701.

Preferably, as will be discussed in more detail below, cassette 702 does not contain any active electrical components. All of the active components of example dispensing mechanism 202 reside in dispenser 701. For example, an antenna 704 can excite a passive memory chip 705 in cassette 702, to determine the contents of cassette 702 (written into passive memory chip 705 when cassette 702 was filled at a remote location). If desired, antenna 704 can also be used to update the data in passive memory chip 705. This wireless data exchange may use any suitable wireless protocol, for example Near Field Communications (NFC), radio frequency identification (RFID), or another wireless protocol.

Dispenser 701 can preferably automatically detect the installation and removal of cassette 702. This automatic detection may facilitate the inventory and tracking of items, and also can help prevent illicit diversion of items. The detection may be accomplished in any suitable way, for example periodic polling using antenna 704, a contact sensor (not shown) that can detect the presence of cassette 702 electromechanically, or by another technique.

In other embodiments, a dispensing mechanism in accordance with embodiments of the invention may not have the separable architecture of dispensing mechanism 202, but may be a single unit including space for storing items to be dispense and including an actuator and other components for dispensing items. In other embodiments that do include a cassette, the cassette may include active components, for example a motor or other actuator, light emitters for sensing, or other components.

As are visible in FIG. 7A, a light emitter 706 and two light receivers 707 are positioned near the bottom of dispenser 701. In operation, light from light emitter 706 reflects from reflective surface 708 (visible in FIG. 7B) and returns to light receivers 707, so long as it is not interrupted by an item being dispensed and falling through the "light curtain" formed across opening. When an item is dispensed through opening 604, it interrupts the light received by either or both of light receivers 707, and dispenser 701 can note that an item has in fact been dispensed. If no light interruption is detected despite a command to dispense an item, computer 103 may assume that a misfeed or other problem has occurred, or that cassette 702 is empty. By using more sophisticated monitoring strategies, accidental dispensing of multiple items may be detected. For example, if two interruptions of the light curtain are detected closely spaced in time, a double feed may be indicated. Emitter 706 may be of any suitable type of emitter, and may emit light in any suitable wavelength or combinations of wavelengths. For example, light emitter 706 may be a light emitting diode, a laser such as a vertical cavity semiconductor emitting laser (VCSEL) or another kind of light source, and may emit visible light, infrared light, or light in other suitable wavelength bands or combinations of wavelength bands.

In other embodiments, light emitter 706 and receivers 707 may be on opposite sides of opening 604, so that receivers 707 receive light directly from light emitter 706 until the light is interrupted by the dispensing of an item.

Figure 8:
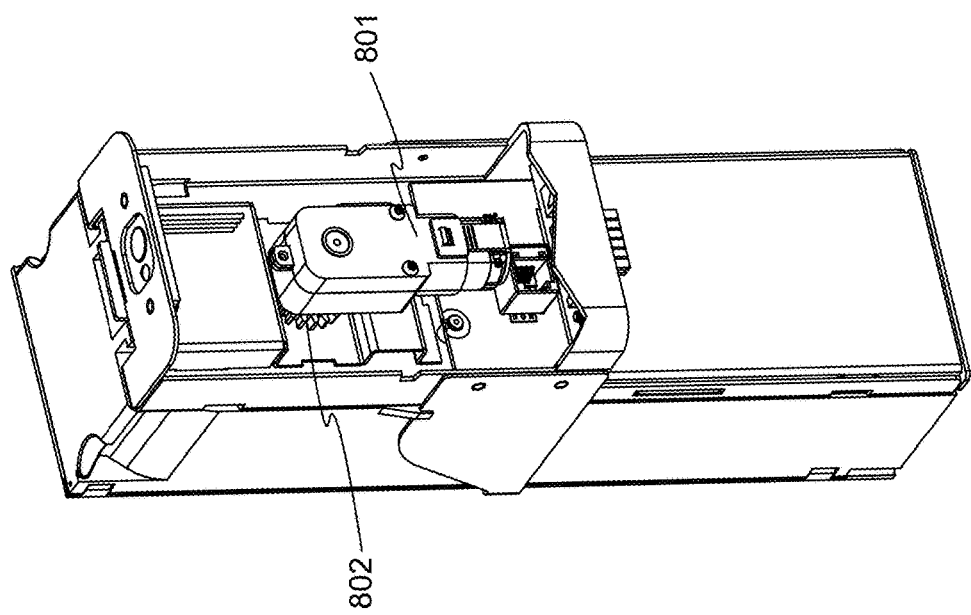
FIG. 8 shows a partially cutaway oblique view of the dispensing mechanism of FIGS. 6A and 6B.

FIG. 8 shows a partially cutaway oblique view of dispensing mechanism 202, revealing some internal details of dispenser 701. A motor 801 having a right-angle drive turns driving gear 802, which engages gear 703 on cassette 702 to actuate cassette 702. Motor 801 may be, for example, a stepper motor whose angular position can be readily moved incrementally and held. In that case, an item may be dispensed by advancing motor 801 by a number of steps known to correspond to one dispensing operation. If the light curtain does not detect that an item is dispensed, motor 801 may be advanced further, and if no dispensing is yet detected, an error message may be generated, or it may be assumed that cassette 702 is empty. Alternatively, motor 801 may be a simple DC or AC motor, in which case dispensing may be accomplished by simply running motor 801 until the dispensing of an item is detected, and then shutting off the motor so that motor 801 is advanced incrementally as far as is needed. A time limit may be imposed, such that if no dispensing is detected within the time limit with motor 801 running, the motor may be shut off and an error message generated.

In other embodiments, an actuator other than a motor may be used. For example, a solenoid or memory metal actuator may provide a reciprocating motion that is used to drive the driving gear within dispenser 701 using a ratchet or ratchet-like arrangement. Other kinds of actuators and driving arrangements are possible.

A microprocessor, microcontroller, or similar controlling circuitry may reside within dispenser 701, and may operate the various active components and sensors of dispenser 701 in response to high-level commands from a supervisory controller elsewhere within restock drawer 106, or from computer 103. In that case, dispenser 701 is considered a "smart" dispenser, because it includes some processing intelligence. However, other architectures are possible. For example, logic signals from a supervisory controller elsewhere within restock drawer 106 may operate dispenser 701.

Figure 9:
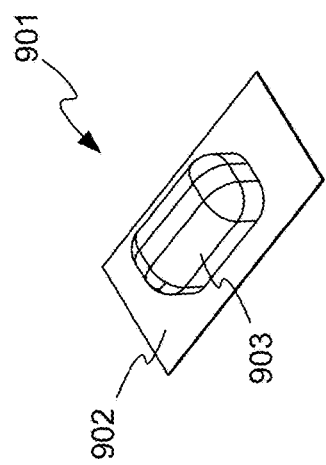
FIG. 9 illustrates a typical blister pack as may be dispensed by the dispensing mechanism of FIGS. 6A and 6B.

As was discussed above, dispensing mechanism 202 may be especially useful for dispensing individual medicine doses such as those commonly packaged in blister packs. FIG. 9 illustrates a typical blister pack 901. A flat portion 902 may be made of cardboard, a stiff plastic, or the like. A plastic bubble-like "blister" 903 is laminated to flat portion 902, with a capsule or the like (not visible) confined within blister 903.

Figure 10:
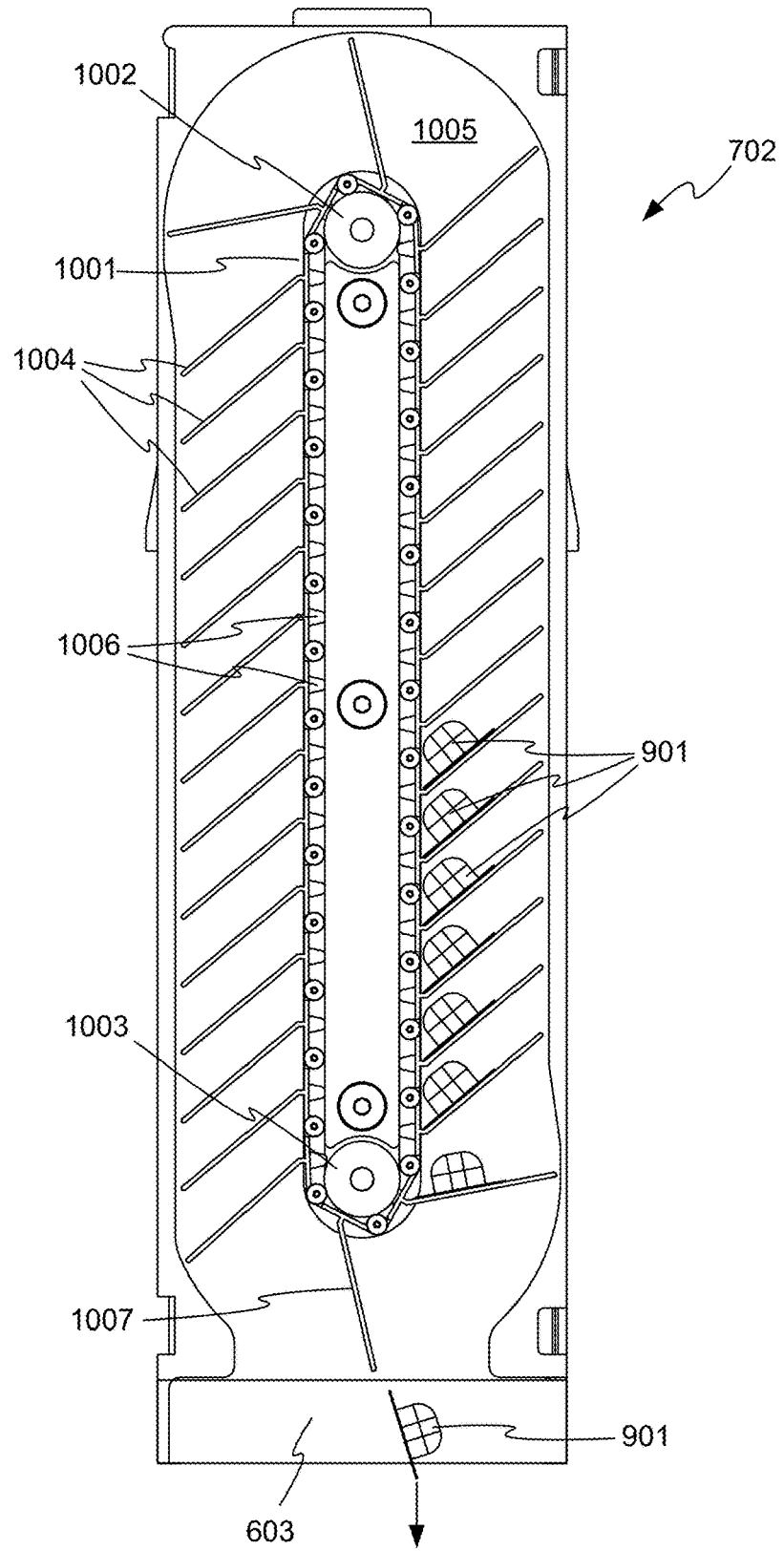
FIG. 10 shows an orthogonal view of a cassette portion of the dispensing mechanism of FIGS. 6A and 6B, with a back cover removed to show some internal workings of the cassette.

FIG. 10 shows an orthogonal view of cassette 702, with its back cover removed, and showing the internal workings of the cassette. A segmented belt 1001 is supported between drive shaft 1002 and idler shaft 1003. Drive shaft 1002 is connected to gear 802, such that belt 1001 is driven by gear 802, and ultimately by motor 801. Motor 801 (and thus belt 1001) may be driven in either direction. Paddles 1004 are integrally formed with segments of belt 1001, and circulate within chamber 1005 as the belt moves. Recesses within drive shaft 1002 and idler shaft 1003 (not visible) engage with teeth 1006 formed on the inner surface of belt 1001, providing positive relationship between the angular position of drive shaft 1002 and the travel of belt 1001.

Other arrangements are possible. For example, belt 1001 could be a continuous belt rather than a segmented belt, and paddles 1004 could be attached to the belt rather than being integrally formed with it.

The spaces between paddles 1004 form a number of storage compartments, some of which are filled with blister packs 901. To dispense an item, belt 1001 is incrementally advanced until the bottommost paddle 1004 holding an item approaches a vertical orientation, as shown by paddle 1007, and the item falls by gravity through opening 604 to dispense drawer 107.

While chamber 1005 is shown as being oriented vertically (being taller than it is wide), this is not a requirement. A dispensing mechanism according to embodiments of the invention may also position a chamber in a horizontal orientation (being wider than it is tall).

Figure 11:
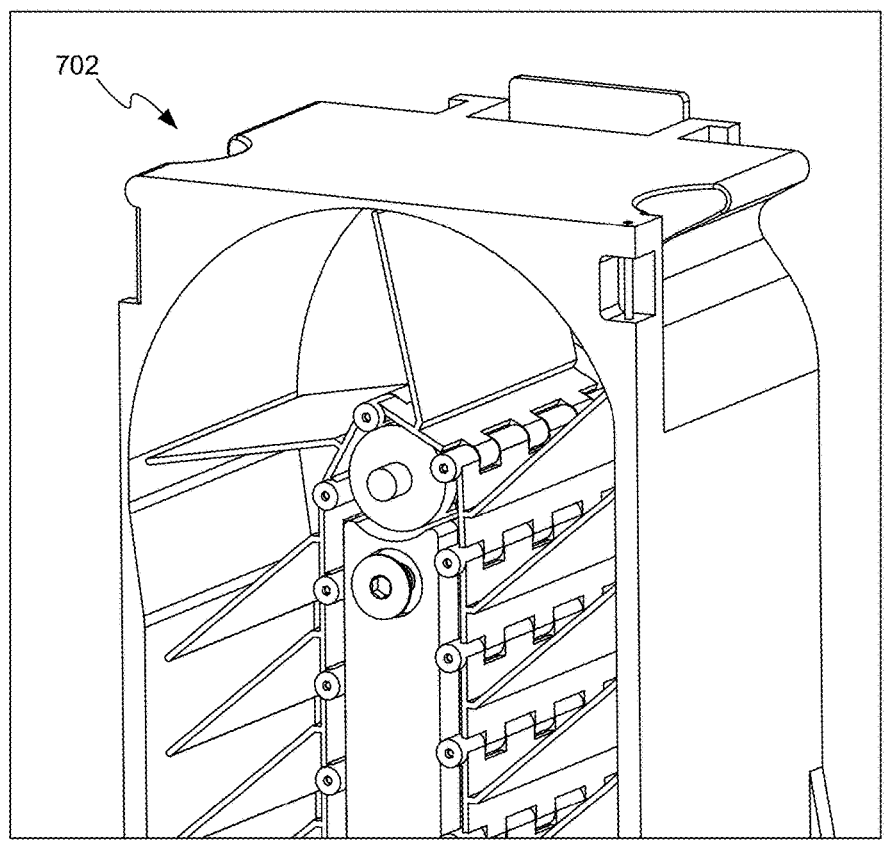
FIG. 11 is an oblique detail view of the upper portion of the cassette of FIG. 10, providing more detail about the construction of the cassette.

FIG. 11 is an oblique detail view of the upper portion of cassette 702, providing more detail about the construction of cassette 702.

The use of paddles 1004 in this manner provides the ability to store a large number of items to be dispensed, in comparison with prior cassette designs, for example the prior helical screw dispenser. Example cassette 702 uses 32 paddles 1004, providing storage for up to 30 items between paddles 1004. More or fewer paddles 1004 could be used, providing a different number of storage spaces, depending on the sizes of the items to be placed in and dispensed from the cassette. While other dimensions are possible, example cassette 702 is approximately 251 mm tall, 72 mm wide, and 49 mm deep, and thus displaces a volume of less than 900 cubic centimeters, or about 30 cubic centimeters for each item that can be stored in cassette 702. In other embodiments, more items may be stored by placing paddles 1004 closer together, making paddles 1004 smaller, or by other miniaturization techniques. For example, in various embodiments, cassette 702 may displace, less than 30, less than 25, less than 20, less than 15, or less than 10 cubic centimeters for each item stored in cassette 702 at full capacity.

In some embodiments, dispensing mechanism 202 may include one or more sensors for directly detecting movement of a mechanical component of dispensing mechanism 202. For example, the driving gear within dispenser 701 may have holes around its main portion, so that the remaining material between the holes functions as broad spokes. A reflective optical sensor may be provided within dispenser 701 that shines light (for example infrared light) onto the driving gear and can detect whether a return reflection is received. Rotation of the gear then results in an alternating signal from the sensor as the reflective "spokes" and the non-reflective holes alternately pass the sensor. A processor or other circuitry within dispenser 701 can interpret this signal to verify the motion of the driving gear. This direct measurement provides additional feedback as to the operation of dispensing mechanism 202. For example, if it is verified using the additional sensor that belt 1001 has moved sufficiently far that an item should be dispensed, but the light curtain sensor does not detect the dispensing of an item, it may be determined that cassette 702 is empty, or it may be suspected that an error has occurred.

Other kinds of sensors could be used to directly measure mechanical motion. For example, the passing of paddles 1004 may be detected by a reflective optical sensor shining light through an opening the wall of chamber 1005. Preferably, any active parts of the sensing system reside in dispenser 701, so that cassette 702 does not include active electrical components.

Dispensing Mechanism for Vials and Other Similarly-Shaped Items

Figure 13:
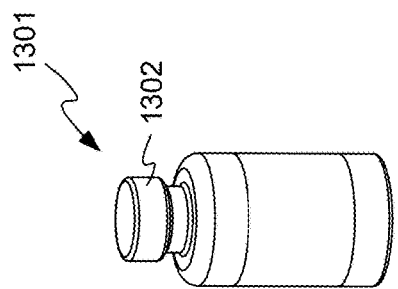
FIG. 13 illustrates a vial as may be dispensed by the dispensing mechanism of FIGS. 12A and 12B.
Figure 12B:
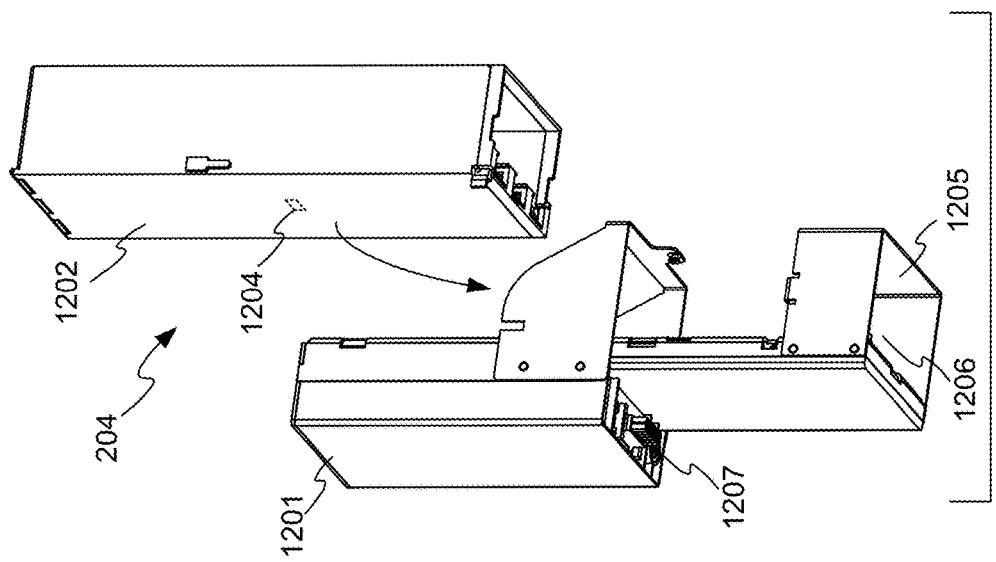
FIGS. 12A and 12B illustrate upper and lower partially exploded oblique views of a second dispensing mechanism in accordance with embodiments of the invention.
Figure 12A:
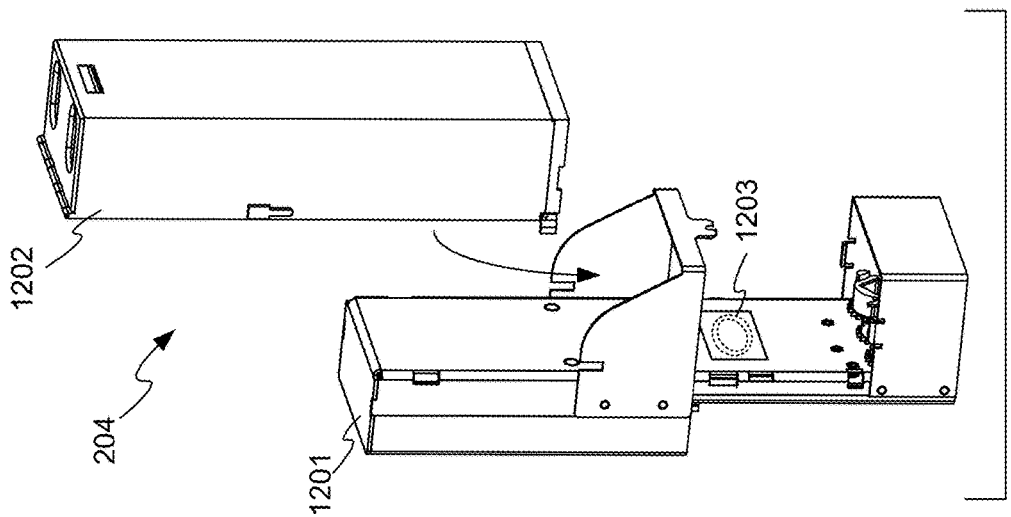

FIGS. 12A and 12B illustrate upper and lower partially exploded oblique views of dispensing mechanism 204. Dispensing mechanism 204 may be especially useful in dispensing vials such vial 1301 shown in FIG. 13, having a protruding cylindrical top 1302. Vial 1301 may be used, for example, for storing fluids for loading into a hypodermic syringe for injection into a patient. Other similarly-shaped items may also be dispensed by dispensing mechanism 204.

Referring again to FIGS. 12A and 12B, example dispensing mechanism includes a dispenser 1201 and a cassette 1202, which may be easily separable for restocking dispensing mechanism 204.

Preferably, cassette 1202 does not contain any active electrical components. All of the active components of dispensing mechanism 204 reside in dispenser 1201. For example, an antenna 1203 can excite a passive memory chip 1204 in cassette 1202, to determine the contents of cassette 1202 (written into passive memory chip 1204 when cassette 1202 was filled at a remote location). If desired, antenna 1203 can also be used to update the data in passive memory chip 1204. This wireless data exchange may use any suitable wireless protocol, for example Near Field Communications (NFC), radio frequency identification (RFID), or another wireless protocol.

Dispenser 1201 can preferably automatically detect the installation and removal of cassette 1202. This automatic detection may facilitate the inventory and tracking of items, and also can help prevent illicit diversion of items. The detection may be accomplished in any suitable way, for example periodic polling using antenna 1203, a contact sensor (not shown) that can detect the presence of cassette 1202 electromechanically, or by another technique. Dispensing mechanism 204 may be removably secured to one of by rails 201 using a snap mechanism, one or more screws, or by another method.

In other embodiments, a dispensing mechanism in accordance with embodiments of the invention may not have the separable architecture of dispensing mechanism 204, but may be a single unit including space for storing items to be dispense and including an actuator and other components for dispensing items. In other embodiments that do include a cassette, the cassette may include active components, for example a motor or other actuator, light emitters for sensing, or other components.

Although not visible in FIGS. 12A and 12B, a light emitter and light receivers are positioned near the bottom of dispenser 1201, and operate similarly to light emitter 706 and receivers 707 described above with respect to dispensing mechanism 202. In operation, light from the light emitter reflects from reflective surface 1205 (visible in FIG. 12B) and returns to the light receivers, so long as it is not interrupted by an item being dispensed and falling through the "light curtain" formed across opening 1206. When an item is dispensed through opening 1206, it interrupts the light received by either or both light receivers, and dispenser 1201 can note that an item has in fact been dispensed. If no light interruption is detected despite a command to dispense an item, computer 103 may assume that a misfeed or other problem has occurred, or that cassette 1202 is empty. By using more sophisticated monitoring strategies, accidental dispensing of multiple items may be detected. For example, if two interruptions of the light curtain are detected closely spaced in time, a double feed may be indicated.

In other embodiments, the light emitters and receivers may be on opposite sides of opening 1206, so that the receivers receive light directly from the light emitters until the light is interrupted by the dispensing of an item.

As is visible in FIG. 12B, a connector 1207, compatible with connectors 302 on rails 201, is positioned to engage one of connectors 302 when dispensing mechanism 204 is installed in restock drawer 106. Although not shown in FIGS. 12A and 12B, dispensing mechanism 204 may include a button and light similar to button 601 and light 602 discussed above, for communication between a restocking technician or other user and computer 103 of cabinet 100.

Figure 14:
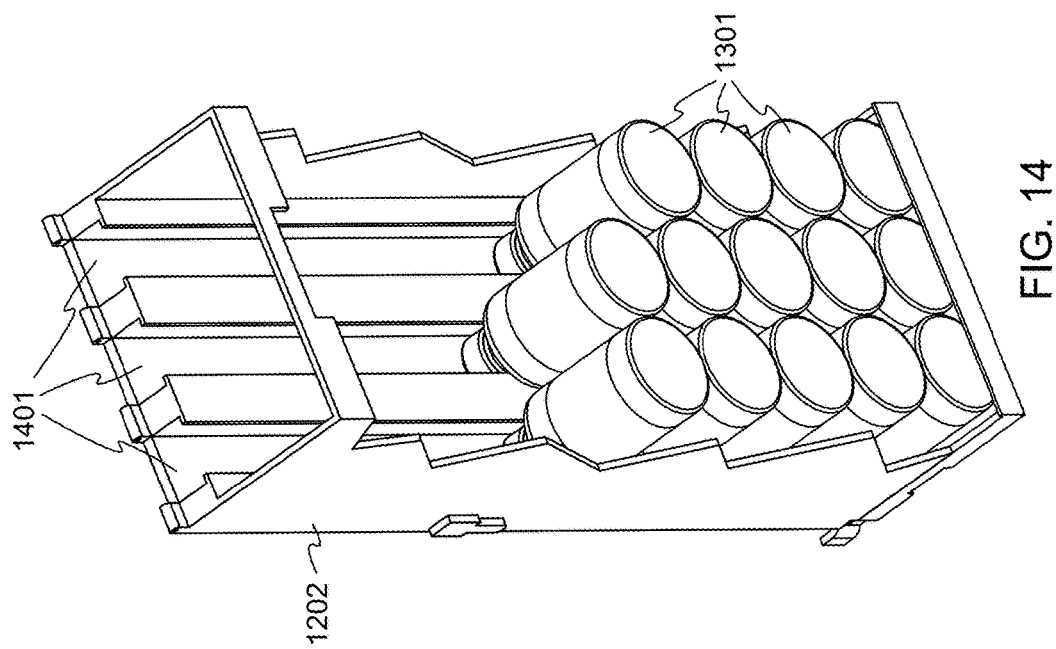
FIG. 14 is a cutaway oblique view of a cassette portion of the dispensing mechanism of FIGS. 12A and 12B, partially filled with vials.

FIG. 14 is a cutaway oblique view of example cassette 1202, partially filled with vials 1301, and with the top of cassette 1202 removed. As is visible in FIG. 14, cassette 1202 includes a number of T-shaped vertical channels 1401 of a shape and size to receive cylindrical tops 1302 of a number of vials 1301 and hold the vials in vertical stacks. Vials 1301 may be, for example, 5 ml vials, having a diameter of about 22 mm, a height of about 42.5 mm. While other dimensions may be used, example cassette 1202 is about 212 mm high, 72 mm wide, and 49 mm deep (displacing about 750 cubic centimeters), and can hold 27 vials of the 5 ml size. Thus, example cassette 1202 displaces less than 28 cubic centimeters for each vial that can be stored in cassette 1202. In other uses, 1 ml vials may be used, having a diameter of about 15 mm, in which case cassette 1202 may hold about 39 of the 1 ml vials, for a displacement of less than 20 cubic centimeters for each vial that can be stored in cassette 1202. Other vial sizes may be used as well. The protruding cylindrical tops of the various vial sizes are preferably similar enough that any compatible size vial can be retained by vertical channels 1401. In various embodiments, cassette 1202 may displace less than 30, less than 25, less than 20, or less than 15 cubic centimeters for each vial stored in cassette 1202 at full capacity.

Figure 15:
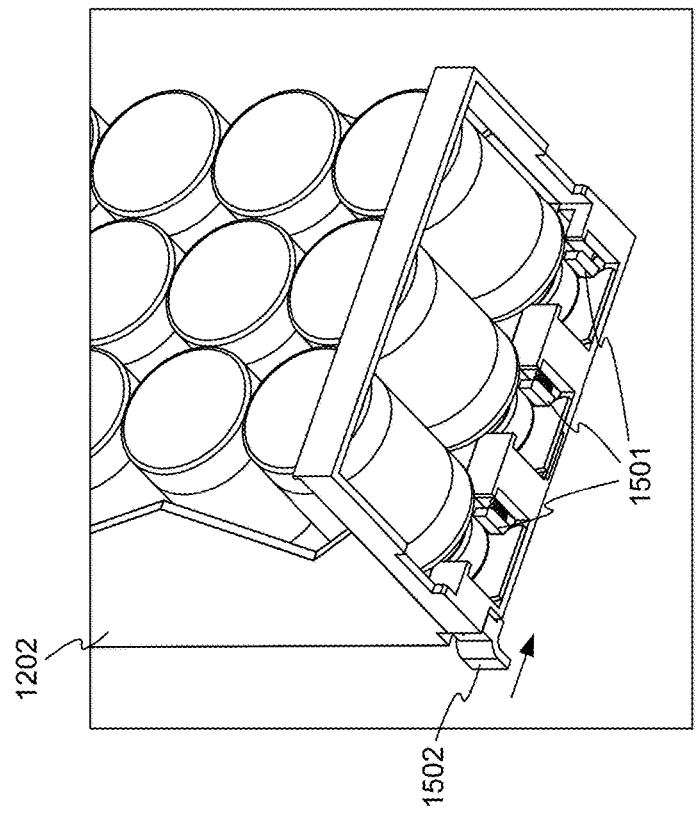
FIG. 15 illustrates a lower oblique view of the cassette portion of FIG. 14.

FIG. 15 illustrates a lower oblique view of loaded cassette 1202, showing spring-loaded latches 1501. While cassette 1202 is separated from dispenser 1201, latches 1501 partially block T-shaped channels 1401, preventing vials 1301 from falling out of cassette 1202. Latches 1501 are connected to a latch release 1502, which when actuated in the direction shown, moves latches out of channels 1401. When cassette 1202 is installed in dispenser 1201, latch release 1502 can be moved and restrained, so that vials 1301 are free to travel down T-shaped channels 1401, as is described in more detail below.

Figure 16:
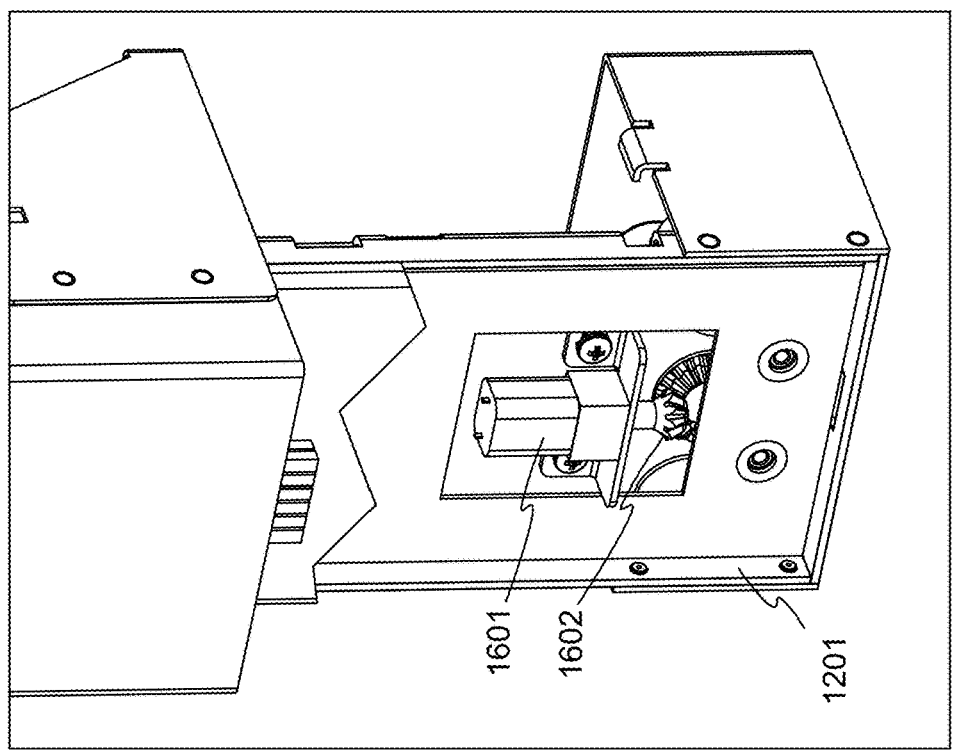
FIG. 16 illustrates a partially-cutaway rear view of the lower portion of a dispenser portion of the dispensing mechanism of FIGS. 12A and 12B.

FIG. 16 illustrates a partially-cutaway rear view of the lower portion of dispenser 1201. As is visible in FIG. 16, a motor 1601 turns a shaft through right-angle gears 1602. Motor 1601 may be, for example, a stepper motor or a simple DC or AC motor, operated in the manner described above in relation to dispensing mechanism 202. That is, motor 1601 may be incrementally advanced either by control of the steps of a stepper motor, or by running motor 1601 only until the dispensing of an item is detected.

In other embodiments, an actuator other than a motor may be used. For example, a solenoid or memory metal actuator may provide a reciprocating motion that is used to drive the gear within dispenser 1201 using a ratchet or ratchet-like arrangement. Other kinds of actuators and driving arrangements are possible.

Figure 17:
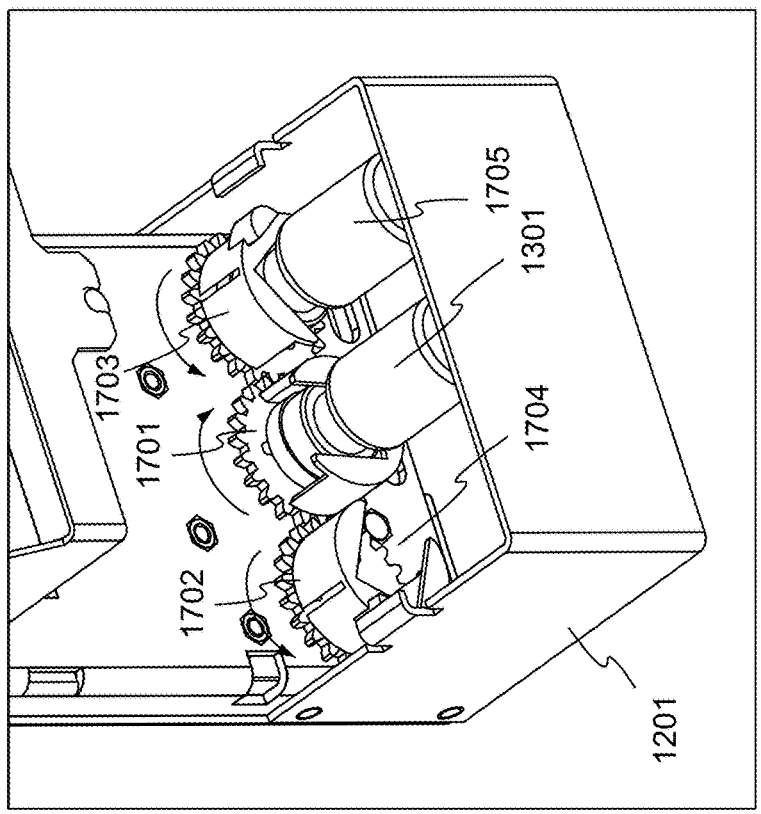
FIG. 17 illustrates a front view of the lower portion of the dispenser of FIG. 16, showing additional details of its operation.

FIG. 17 illustrates a front view of the lower portion of dispenser 1201, showing additional details of its operation. A central slotted gear 1701 is driven directly by right angle gears 1602. While a rotation direction is shown for ease of explanation, the choice of rotation direction is arbitrary, and either direction may be used. Slotted gear 1701 drives slotted gears 1702 and 1703. Each of the slotted gears has a T-shaped blind slot 1704 of a shape and size to receive the cylindrical top of a vial 1301. Here, "blind" means that the slot does not continue all the way through the slotted gear.

As the slotted gears rotate, the respective slots 1704 "take turns" reaching an upward vertical orientation and a downward vertical orientation. For example, the three slotted gears of example dispenser 1201 are meshed in such a way that one of the T-shaped slots reaches the upward vertical orientation for every 120 degrees of rotation of central slotted gear 1701. If different numbers of slotted gears are present, then a different angular separation of the gear positions may be used, but preferably slots 1704 reach the downward vertical orientation at evenly spaced angular intervals of the driving gear 1701.

When one of the slots reaches its upward vertical orientation and at least one vial is present in the corresponding T-shaped vertical channel of cassette 1202 (not shown), the vial is free to drop into the T-shaped blind slot 1704 of the respective slotted gear. In FIG. 17, slotted gear 1701 has just received a vial 1301 in this manner. Slotted gear 1703 has previously received a vial 1705. As the gears continue to turn, the slot in slotted gear 1702 approaches its downward vertical orientation. When the downward vertical orientation is reached, vial 1705 will be free to drop through opening 1206 into dispense drawer 107. Slot 1704 of slotted gear 1703 is approaching its upward vertical orientation, to receive another vial, if one is present. Thus, the vials in cassette 1202 can be dispensed one by one.

In some embodiments, dispensing mechanism 204 may include one or more sensors for directly detecting movement of a mechanical component of dispensing mechanism 204. For example, the driven gear within dispenser 1201 may have holes around its main portion, so that the remaining material between the holes functions as broad spokes. A reflective optical sensor may be provided within dispenser 1201 that shines light (for example infrared light) onto the driving gear and can detect whether a return reflection is received. Rotation of the gear then results in an alternating signal from the sensor as the reflective "spokes" and the non-reflective holes alternately pass the sensor. A processor or other circuitry within dispenser 1201 can interpret this signal to verify the motion of the driven gear. This direct measurement provides additional feedback as to the operation of dispensing mechanism 204. For example, if it is verified using the additional sensor that the gear has moved sufficiently far that an item should be dispensed (120 degrees in the example embodiment), but the light curtain sensor does not detect the dispensing of an item, it may be determined that cassette 1202 is empty, or it may be suspected that an error has occurred.

Other kinds of sensors could be used to directly measure mechanical motion. For example, the teeth of slotted gear 1702 or 1703 may be visible to a reflective optical sensor shining light through an opening the wall of dispenser 1201, and the rotation of the slotted gears may be detected by monitoring the passing of the individual gear teeth. Preferably, any active parts of the sensing system reside in dispenser 1201, so that cassette 1202 does not include active electrical components.

Dispenser for Syringes and Other Similarly-Shaped Items

FIGS. 18A and 18B illustrate upper and lower views of dispensing mechanism 203 in more detail. Dispensing mechanism 203 may be especially useful for dispensing cylindrical items such as syringes, although dispensing mechanism 203 may be useful for dispensing other similarly-shaped items as well.

Example dispensing mechanism 203 comprises a dispenser 1801 and a cassette 1802, which are separable. For example, dispenser 1801 and cassette 1802 may snap together, may be separable with the removal of one or a small number of screws, or may be reasonably separable in some other way without damage to either dispenser 1801 or cassette 1802. In this way, restocking may be accomplished by replacing a depleted cassette 1802 with a full cassette 1802.

As is visible in FIG. 18B, a connector 1803, compatible with connectors 302 on rails 201, is positioned to engage one of connectors 302 when dispensing mechanism 203 is installed in restock drawer 106. Dispenser 1801 defines an opening 1804 at the bottom of dispensing mechanism 203, through which items are dispensed. Dispensing mechanism 203 may be removably secured to one of rails 201 using a snap mechanism, one or more screws, or by another method.

Preferably, cassette 1802 does not contain any active electrical components. All of the active components of dispensing mechanism 203 reside in dispenser 1801. For example, an antenna 1805 can excite a passive memory chip 1806 in cassette 1802, to determine the contents of cassette 1802 (written into passive memory chip 1806 when cassette 1802 was filled at a remote location). If desired, antenna 1805 can also be used to update the data in passive memory chip 1806. This wireless data exchange may use any suitable wireless protocol, for example Near Field Communications (NFC), radio frequency identification (RFID), or another wireless protocol.

Dispenser 1801 can preferably automatically detect the installation and removal of cassette 1802. This automatic detection may facilitate the inventory and tracking of items, and also can help prevent illicit diversion of items. The detection may be accomplished in any suitable way, for example periodic polling using antenna 1805, a contact sensor (not shown) that can detect the presence of cassette 1802 electromechanically, or by another technique.

In other embodiments, a dispensing mechanism in accordance with embodiments of the invention may not have the separable architecture of dispensing mechanism 203, but may be a single unit including space for storing items to be dispense and including an actuator and other components for dispensing items. In other embodiments that do include a cassette, the cassette may include active components, for example a motor or other actuator, light emitters for sensing, or other components.

A light emitter 1807 and two light receivers 1808 are positioned near the bottom of dispenser 1801. In operation, light from light emitter 1807 reflects from a reflective surface of dispenser 1801 (not visible in FIGS. 18A and 18B, but opposite light emitter 1807 and receivers 1808) and returns to light receivers 1808, so long as it is not interrupted by an item being dispensed and falling through the "light curtain" formed across opening 1804. When an item is dispensed through opening 1804, it interrupts the light received by either or both of light receivers 1808, and dispenser 1801 can note that an item has in fact been dispensed. If no light interruption is detected despite a command to dispense an item, computer 103 may assume that a misfeed or other problem has occurred, or that cassette 1802 is empty. By using more sophisticated monitoring strategies, accidental dispensing of multiple items may be detected. For example, if two interruptions of the light curtain are detected closely spaced in time, a double feed may be indicated. Emitter 1807 may be of any suitable type of emitter, and may emit light in any suitable wavelength or combinations of wavelengths. For example, light emitter 1807 may be a light emitting diode, a laser such as a vertical cavity semiconductor emitting laser (VCSEL) or another kind of light source, and may emit visible light, infrared light, or light in other suitable wavelength bands or combinations of wavelength bands.

In other embodiments, light emitter 1807 and receivers 1808 may be on opposite sides of opening 1804, so that receivers 1808 receive light directly from light emitter 1807 until the light is interrupted by the dispensing of an item.

A clear window 1809 may be provided, so that a user can see the contents of cassette 1802.

Although not shown in FIGS. 18A and 18B, a button and light similar to button 601 and light 602 discussed above, for communication between a restocking technician or other user and computer 103 of cabinet 100.

Figure 19:
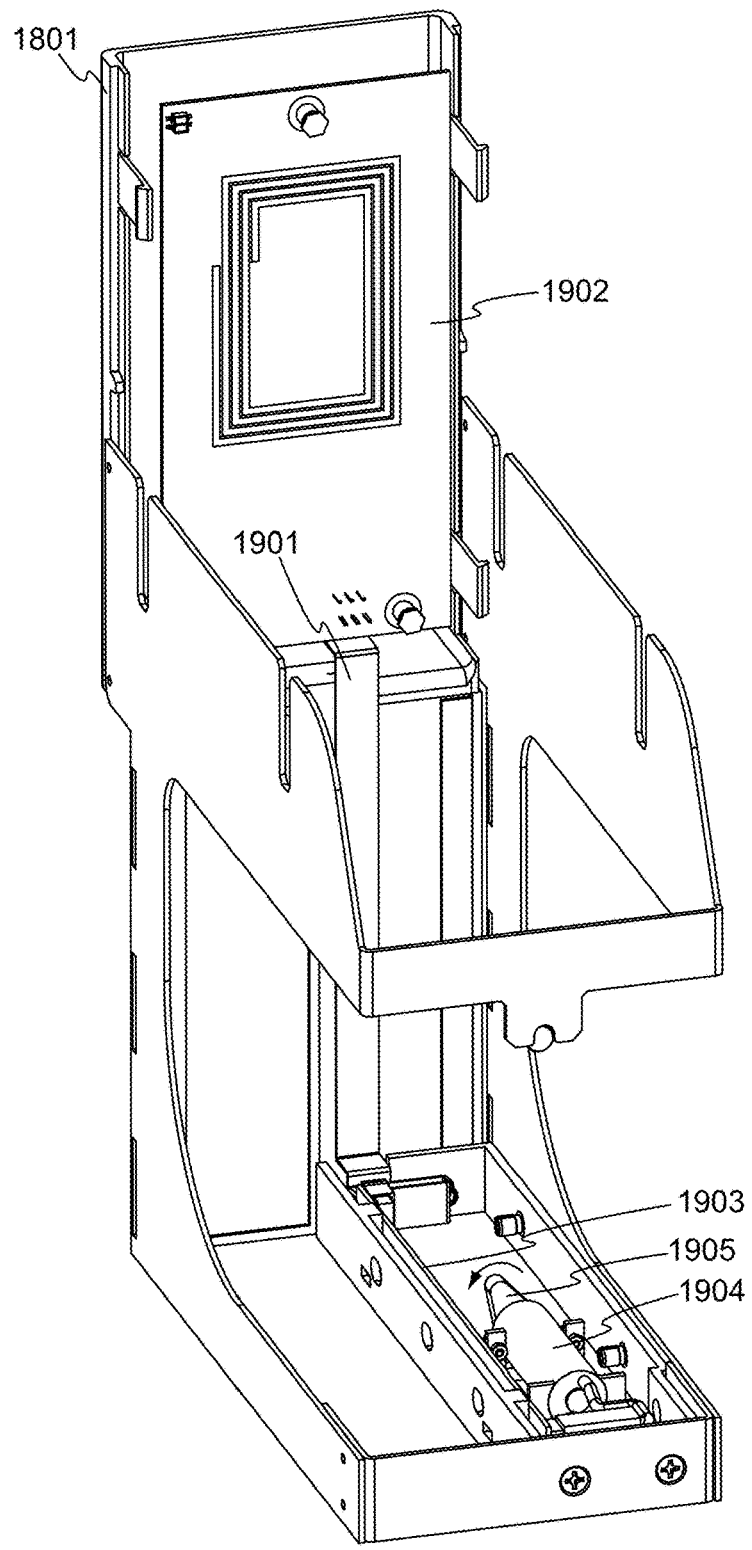
FIG. 19 shows an oblique view of a dispenser portion of the dispensing mechanism of FIGS. 18A and 18B with some parts removed, revealing internal details of the operation of the dispenser portion.

FIG. 19 shows an oblique view of dispenser 1801 with some parts removed, revealing internal details of the operation of dispenser 1801. A cable 1901 connects a first circuit board 1902 with a second circuit board 1903, to which a motor 1904 is connected. Motor 1904 may be, for example, a stepper motor whose angular position can be readily moved incrementally and held. In that case, an item may be dispensed by advancing motor 1904 by one rotation. If the light curtain does not detect that an item is dispensed, motor 1904 may be advanced further, and if no dispensing is yet detected, an error message may be generated, or it may be assumed that cassette 1802 is empty. Alternatively, motor 1904 may be a simple DC or AC motor, in which case dispensing may be accomplished by simply running motor 1904 until the dispensing of an item is detected, and then shutting off the motor. A time limit may be imposed, such that if no dispensing is detected within the time limit with motor 1904 running, the motor may be shut off and an error message generated.

Motor 1904 turns a cam 1905 in the direction shown, the function of which is explained in more detail below.

A microprocessor, microcontroller, or similar controlling circuitry may reside within dispenser 1801, and may operate the various active components and sensors of dispenser 1801 in response to high-level commands from a supervisory controller elsewhere within restock drawer 106, or from computer 103. In that case, dispenser 1801 is considered a "smart" dispenser, because it includes some processing intelligence. However, other architectures are possible. For example, logic signals from a supervisory controller elsewhere within restock drawer 106 may operate dispenser 1801.

Figure 20:
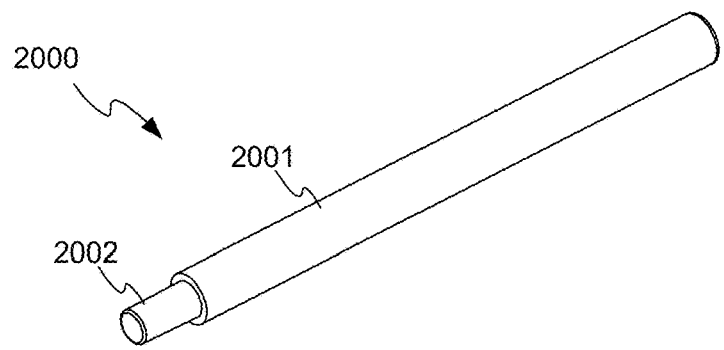
FIG. 20 illustrates a syringe as may be dispensed by the dispensing mechanism of FIGS. 18A and 18B.

As was discussed above, dispensing mechanism 203 may be especially useful for dispensing syringes or other similarly-shaped items. FIG. 20 illustrates a typical syringe 2000 of a kind that may be dispensed by dispensing mechanism 203. Syringe 2000 has a main barrel 2001 configured to hold a quantity of a serum or other liquid, and a reduced diameter portion 2002 configured to accept a hypodermic needle or the like. In some embodiments, the outer diameter of main barrel portion may be about 11.2 mm, and the overall length of syringe 2000 may be in keeping with the capacity of syringe 2000. For example, a syringe 2000 configured to hold 1 ml of liquid may have an overall length of about 115 mm, while a syringe 2000 configured to hold 2 ml of liquid may have an overall length of about 148 mm. These dimensions are given only as examples, and syringes or other items having different sizes may be used in embodiments of the invention.

Figure 21A:
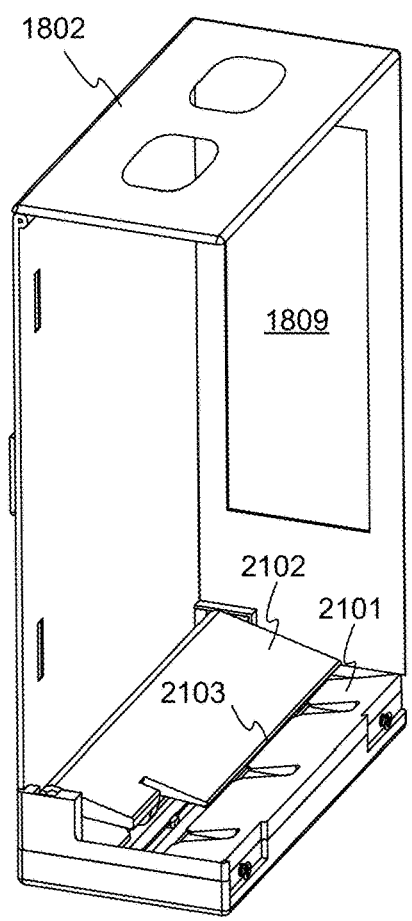
FIGS. 21A and 21B illustrate a cassette portion of the dispensing mechanism of FIGS. 18A and 18B with certain outer panels removed, and revealing internal details of the cassette portion.
Figure 21B:
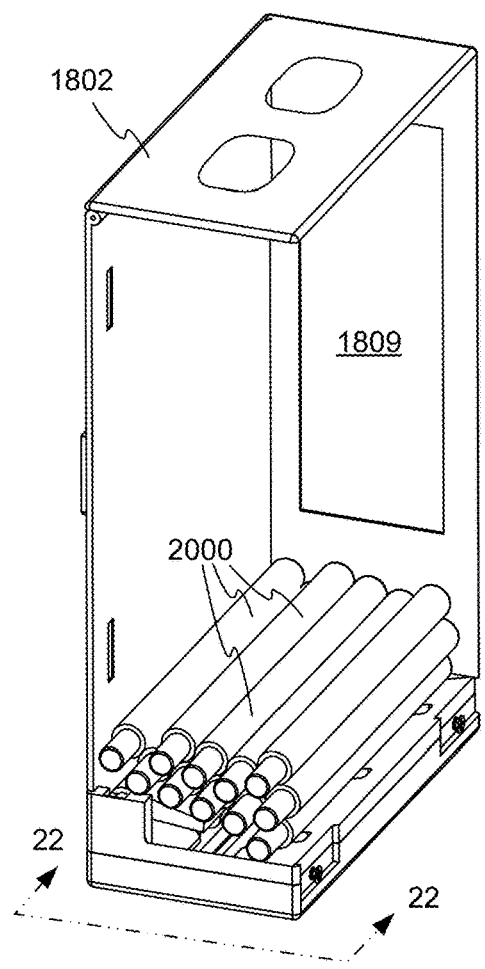

FIGS. 21A and 21B illustrate cassette 1802 with certain outer panels removed, and revealing internal details of cassette 1802. In FIG. 21A, cassette 1802 is empty, and in FIG. 21B, cassette 1802 contains a number of syringes 2000. An angled floor 2101 of cassette 1802 and an angled moveable guide 2102 serve to funnel syringes 2000 toward the lowest part 2013 of cassette 1802, to be dispensed in the manner described below. While other dimensions are possible, example cassette 1802 is about 234 mm high, 71 mm deep, and 153 mm wide, and thus displaces an overall volume of less than 2600 cubic centimeters, and can hold up to 120 or more syringes 2000. Cassette 1802 thus displaces less than 22 cubic centimeters for each syringe that can be stored in cassette 1802. While syringes 2000 having a 2 ml capacity are shown, cassette 1802 may be configured to dispense syringes having a smaller overall length by placing a spacer block (not shown) within cassette 1802. In various embodiments, cassette 1802 may displace less than 25, less than 20, less than 15, or less than 10 cubic centimeters for each item stored in cassette 1802 at full capacity.

Figure 22A:
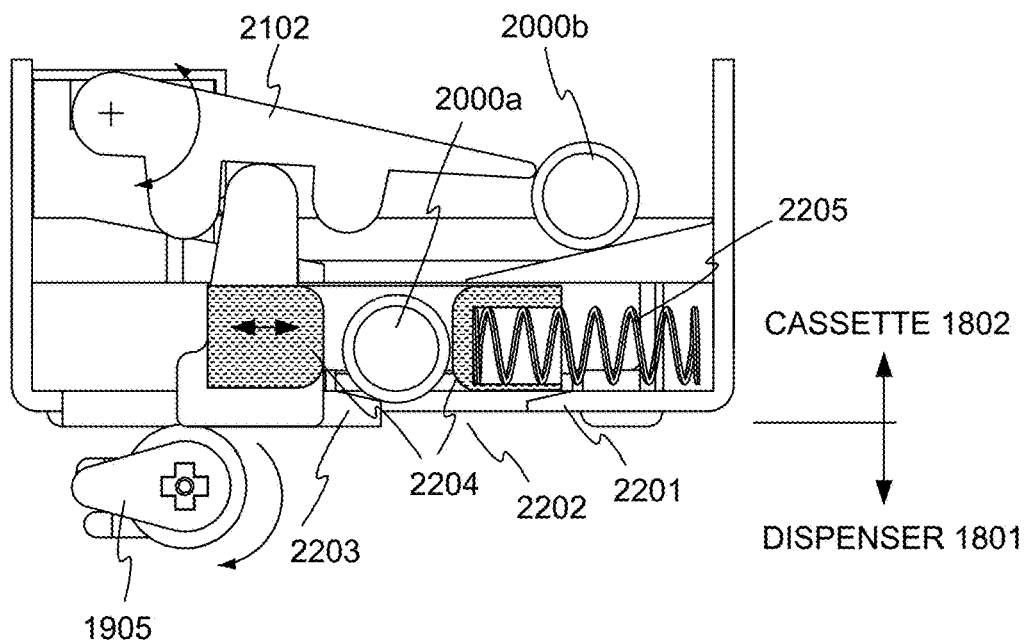
FIGS. 22A-22C illustrate a cutaway view of portions of the dispensing mechanism of FIGS. 18A and 18B and their operation to dispense a syringe.
Figure 22B:
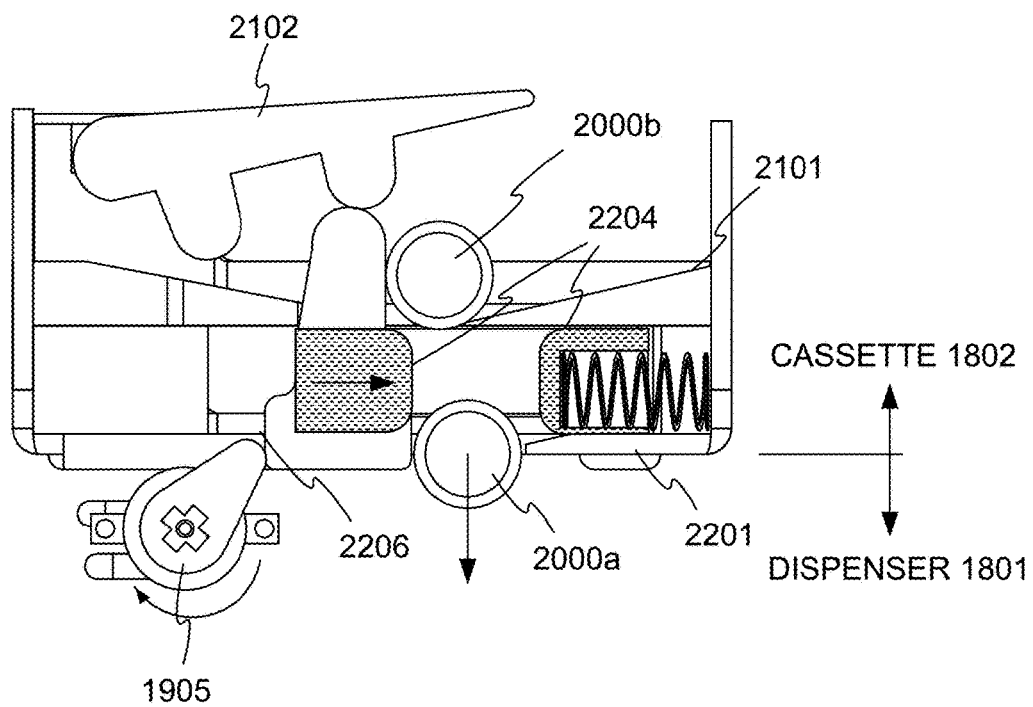
Figure 22C:
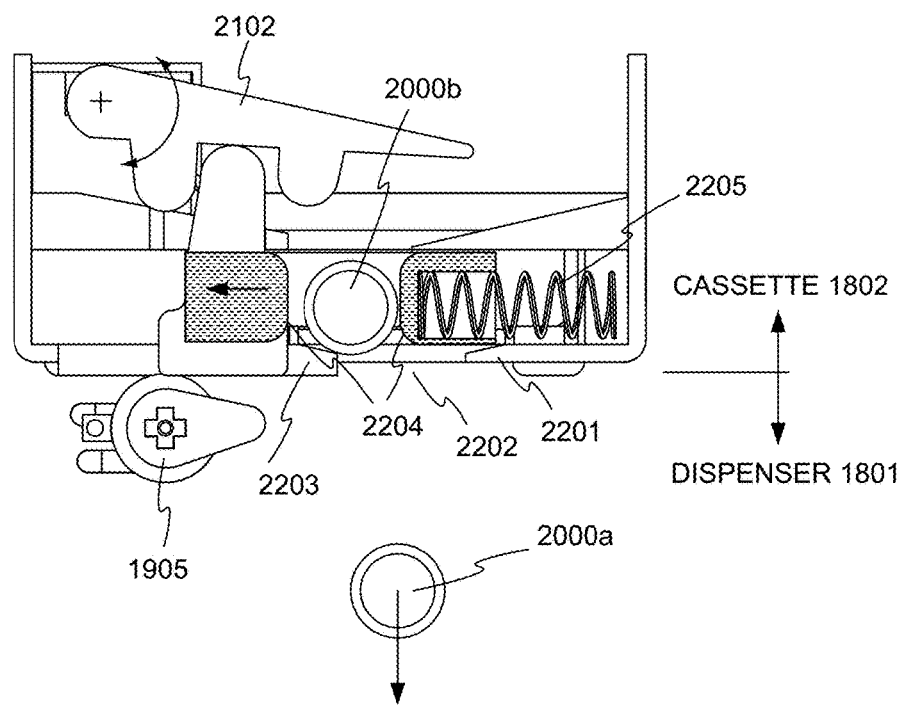

FIGS. 22A-22C illustrate a cutaway view of portions of dispenser 1801 and cassette 1802 and their operation to dispense a syringe. A bottom tray 2201 of cassette 1802 defines an opening 2202 and a ledge 2203. A movable slide 2204 defines a slot in which syringe 2000a is positioned in FIG. 22A. Slide 2204 is biased to the left by spring 2205, such that syringe 2000a remains suspended by ledge 2203. Syringe 2000a is in position to be dispensed, while cassette 1802 contains additional syringes such as syringe 2000b. Spring 2205 also ensures that the syringes in cassette 1802 are not accidentally dispensed when cassette 1802 is separated from dispenser 1801, for example during transport from a central pharmacy to cabinet 100.

When it is desired to dispense a syringe, motor 1904 (not visible in FIGS. 22A-22C) turns cam 1905 as shown in FIG. 22B. Cam 1905 acts against surface 2206 of slide 2204, moving slide 2204 to the right, aligning the slot in slide 2204 with opening 2202 in bottom tray 2201 of cassette 1802. Syringe 2000a can accordingly drop through opening 2202 and into dispense drawer 107. Syringe 2000b rolls down angled floor 2010 into position between slide 2204 and angled floor 2101. Guide 2102 is force upward by its interaction with slide 2204, to jostle any remaining syringes within cassette 1802, facilitating their future dispensing.

In FIG. 22C, cam 1905 has rotated past its contact with slide 2204, allowing spring 2205 to force slide 2204 back to its nominal position. Sensor electronics may sense the dispensing of syringe 2000a, or that slide 2204 is back to its nominal position, and may shut off motor 1904, stopping cam 1905. Syringe 2000b drops into the slot in slide 2204, resting on ledge 2203, in preparation for its future dispensing.

In other embodiments, an actuator other than a motor may be used. For example, a solenoid or memory metal actuator may provide a translational motion that is used to directly translate slide 2204 against spring 2205. Other kinds of actuators and driving arrangements are possible.

In some embodiments, dispensing mechanism 203 may include one or more sensors for directly detecting movement of a mechanical component of dispensing mechanism 203. For example, slide 2204 may be generally non-reflective, but may include a reflective sticker placed for detection by a reflective optical when slide 2204 moves under the action of cam 1905. The passing of the reflective sticker, as detected by the sensor, verifies that slide 2204 has actually moved. A similar effect may be achieved by placing a magnet on slide 2204 and detecting its passing of a Hall Effect sensor. Similarly, the movement of cam 1905 could be directly sensed. A processor or other circuitry within dispenser 1801 can interpret a signal produced by the sensor to verify the motion of the slide or cam. This direct measurement provides additional feedback as to the operation of dispensing mechanism 203. For example, if it is verified using the additional sensor that slide 2204 has moved sufficiently far that an item should be dispensed, but the light curtain sensor does not detect the dispensing of an item, it may be determined that cassette 1802 is empty, or it may be suspected that an error has occurred.

Figure 23:
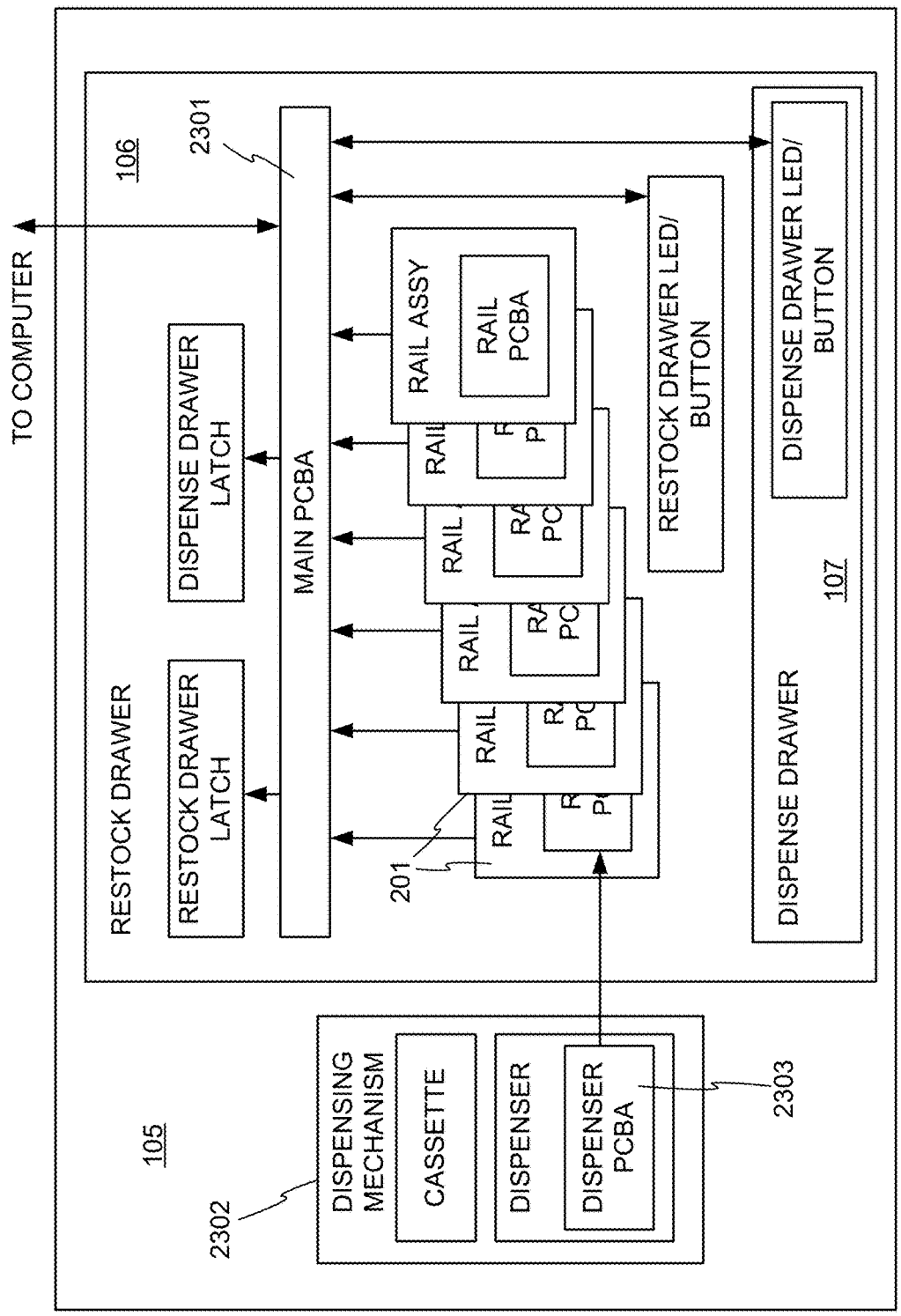
FIG. 23 illustrates an electrical block diagram of the dispensing unit of FIG. 2, in accordance with embodiments of the invention.

FIG. 23 illustrates an electrical block diagram of dispensing unit 105, in accordance with embodiments of the invention. Among other components, dispensing unit 105 includes a main PCBA 2301, and a number of rail assemblies 201, each of which includes a respective PCBA. Only one generic dispensing mechanism 2302 is shown, but it will be recognized that a number of dispensing mechanisms such as dispensing mechanisms 202, 203, and 204 may be present. Each dispensing mechanism may have its own PCBA 2303.

Figure 24:
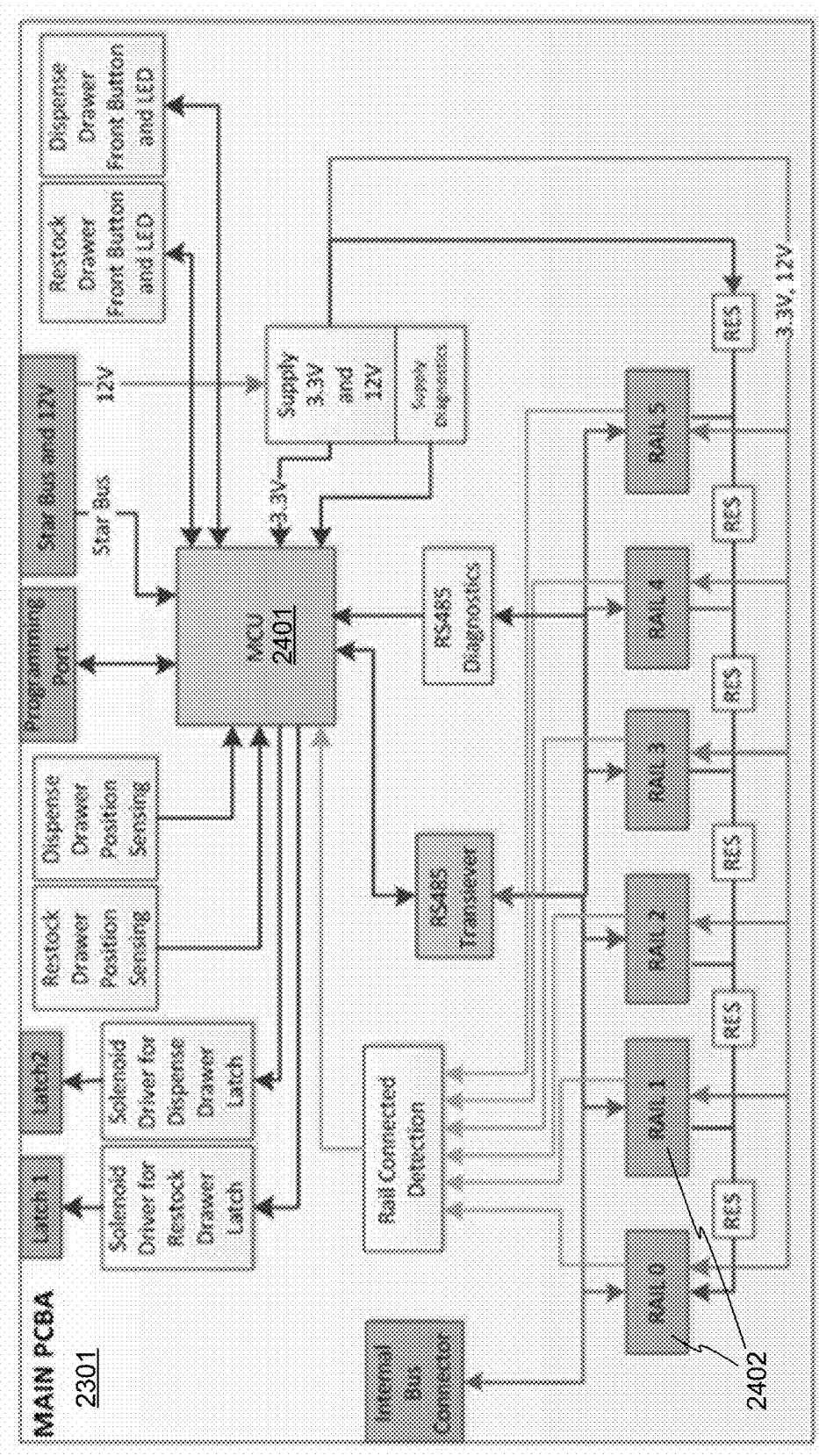
FIG. 24 illustrates an electrical block diagram of a printed circuit board in the restock drawer of FIG. 2, in accordance with embodiments of the invention.

FIG. 24 illustrates a more detailed electrical block diagram of restock drawer 106 main PCBA 2301, in accordance with embodiments of the invention. Main PCBA 2301 include a microcontroller 2401, as well as various sensing and communication circuitry, and connections 2402 for connection to rail assemblies 201.

Figure 25:
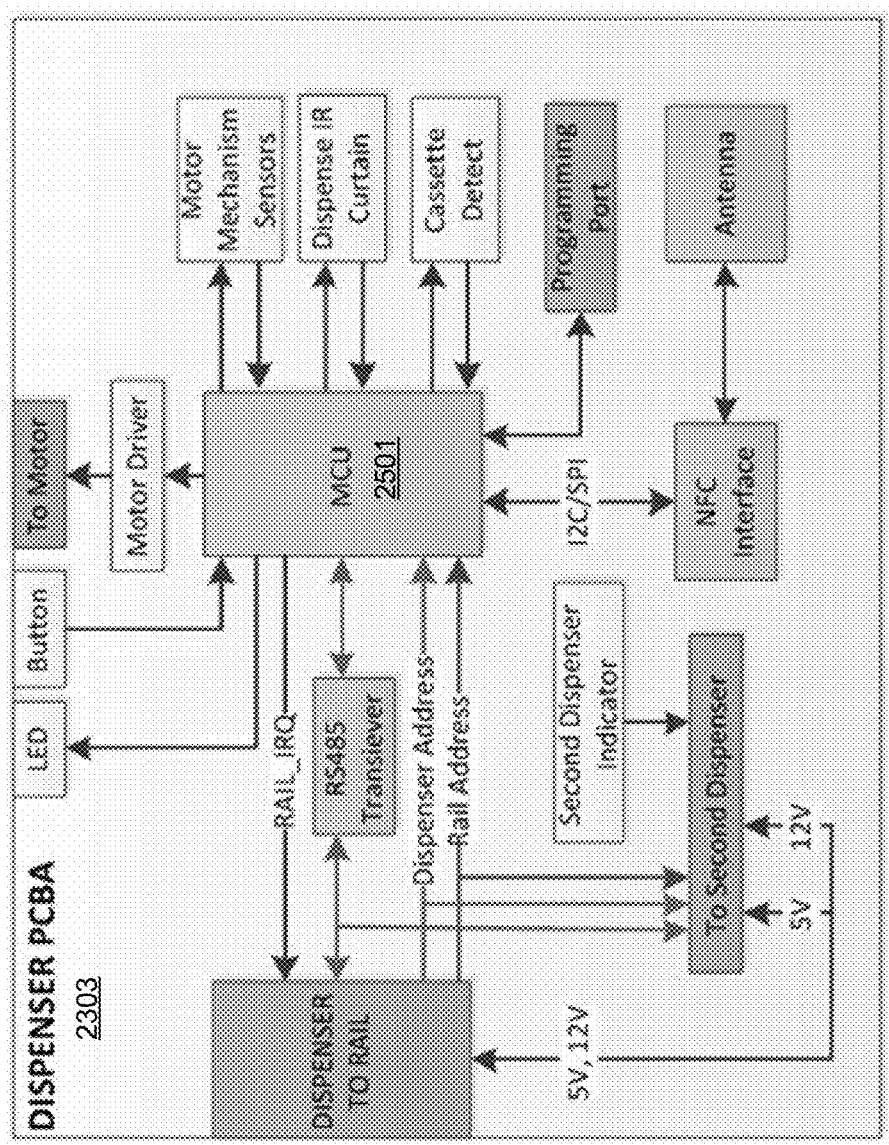
FIG. 25 illustrates an electrical block diagram of a dispenser as may be used in the dispensing mechanisms of FIGS. 6A, 12A, and 18A, in accordance with embodiments of the invention.

FIG. 25 illustrates a more detailed electrical block diagram of a dispenser PCBA 2303, in accordance with embodiments of the invention. In this example, the dispenser includes a microcontroller 2501, and the dispenser represented is a "smart" dispenser. Dispenser PCBA 2303 also includes various power and communication circuitry, driver circuitry for a motor, a wireless communication interface and antenna, various other sensors, and other components, many of which may be described above in relation to dispensers 701, 1201, and 1801.

Additional Dispensing Mechanism for Blister Packs and Other Small Items

Figure 26A:
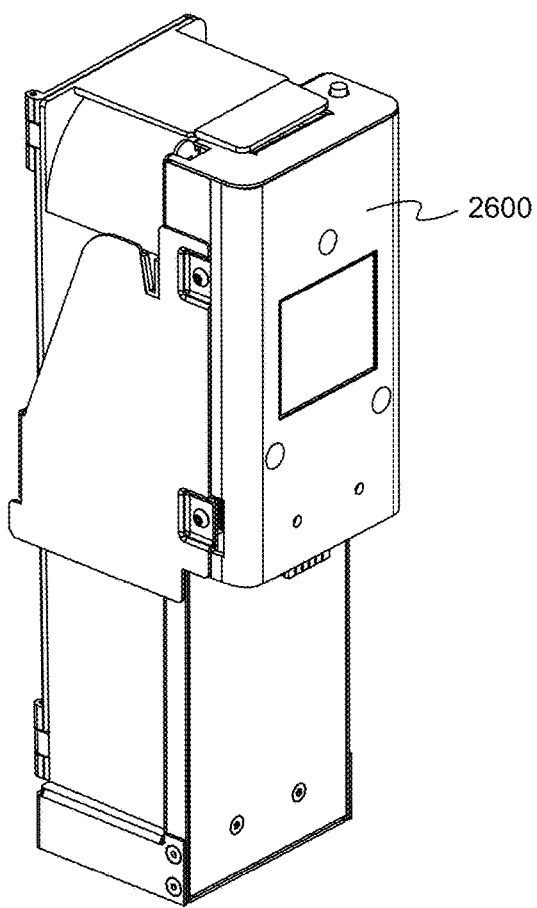
FIGS. 26A and 26B illustrate upper and lower views of a dispensing mechanism in accordance with other embodiments of the invention.
Figure 26B:
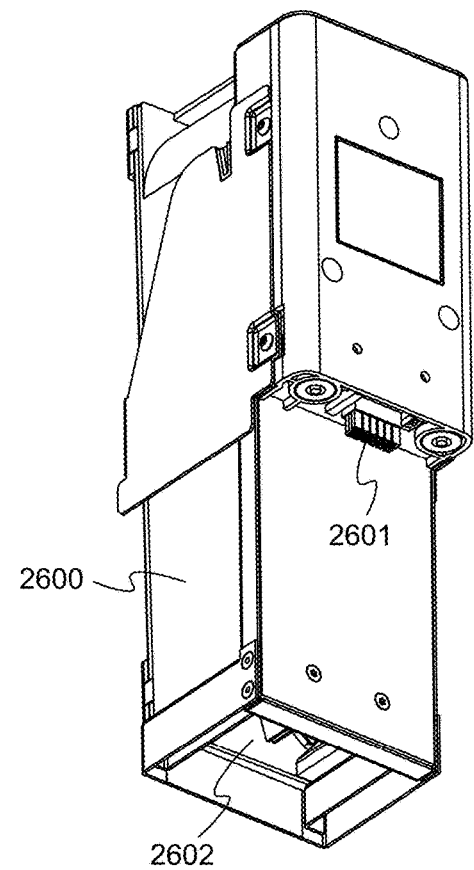

FIGS. 26A and 26B illustrate a dispensing mechanism 2600 in accordance with other embodiments of the invention. Dispensing mechanism 2600 is similar in some ways to dispensing mechanism 202 described above, and may be especially useful for dispensing small items such as individual medicine doses packaged in well-known "blister packs" such as blister pack 901, although dispensing mechanism 2600 may be useful for dispensing may other kinds of items as well. Like dispensing mechanism 202, dispensing mechanism 2600 may include one or more buttons or lights, and may have an internal processor that controls the operation of dispensing mechanism 2600. Dispensing mechanism 2600 includes a connector 2601, compatible with connectors 302 on rails 201 and positioned to engage one of connectors 302 when dispensing mechanism 202 is installed in restock drawer 106. Various parts of dispensing mechanism 2600 collectively constitute a housing that defines an opening 2602 at the bottom of dispensing mechanism 2600, through which items are dispensed. Dispensing mechanism 2600 may be removably secured to one of rails 201 using a snap mechanism, one or more screws, or by another method.

Figure 27B:
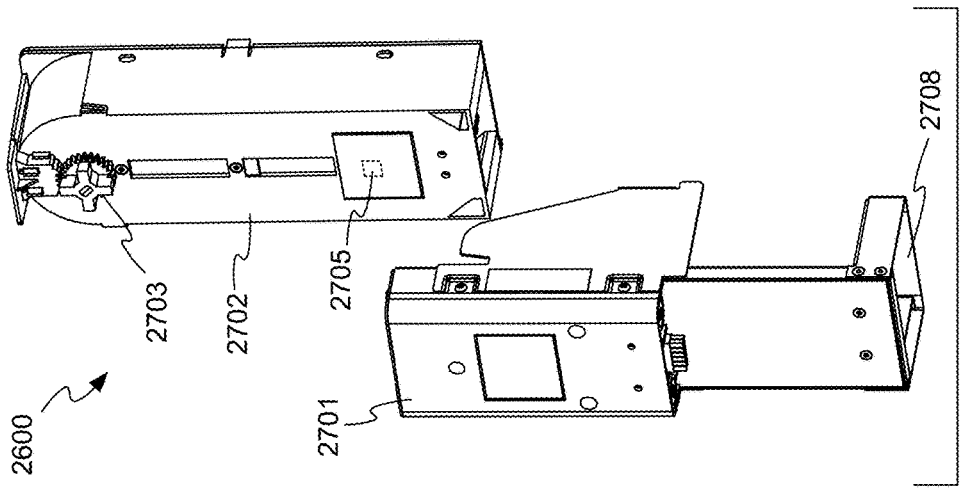
FIGS. 27A and 27B illustrate partially exploded views of the dispensing mechanism of FIGS. 26A and 26B.
Figure 27A:
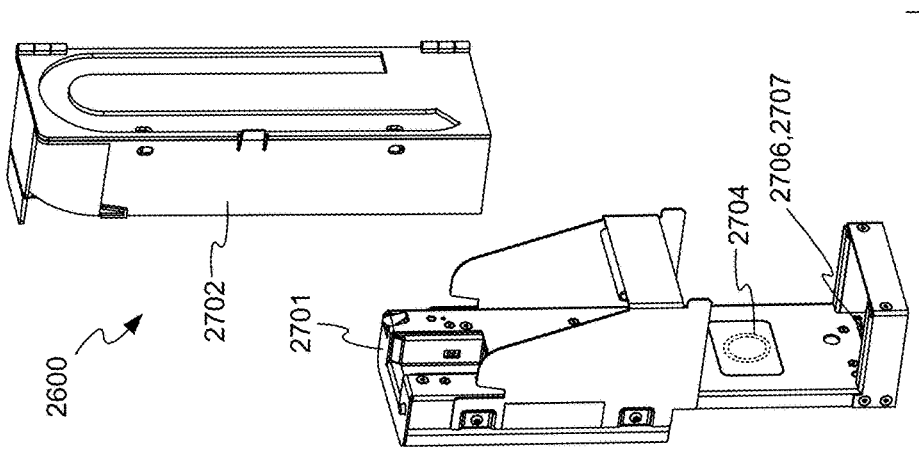

As is shown in FIGS. 27A and 27B, example dispensing mechanism 2600 comprises a dispenser 2701 and a cassette 2702, which are separable. For example, dispenser 2701 and cassette 2702 may snap together, may be separable with the removal of one or a small number of screws, or may be reasonably separable in some other way without damage to either dispenser 2701 or cassette 2702. In this way, restocking may be accomplished by replacing a depleted cassette 2702 with a full cassette 2702. A gear 2703 engages a driving gear (not easily visible in FIG. 27A) within dispenser 2701 when cassette 2702 is assembled to dispenser 2701.

Preferably, as will be discussed in more detail below, cassette 2702 does not contain any active electrical components. All of the active components of example dispensing mechanism 2600 reside in dispenser 2701. For example, an antenna 2704 can excite a passive memory chip 2705 in cassette 2702, to determine the contents of cassette 2702 (written into passive memory chip 2705 when cassette 2702 was filled at a remote location). If desired, antenna 2704 can also be used to update the data in passive memory chip 2705. This wireless data exchange may use any suitable wireless protocol, for example Near Field Communications (NFC), radio frequency identification (RFID), or another wireless protocol.

Dispenser 2701 can preferably automatically detect the installation and removal of cassette 2702. This automatic detection may facilitate the inventory and tracking of items, and also can help prevent illicit diversion of items. The detection may be accomplished in any suitable way, for example periodic polling using antenna 2704, a contact sensor (not shown) that can detect the presence of cassette 2702 electromechanically, or by another technique.

In other embodiments, a dispensing mechanism in accordance with embodiments of the invention may not have the separable architecture of dispensing mechanism 2600, but may be a single unit including space for storing items to be dispense and including an actuator and other components for dispensing items. In other embodiments that do include a cassette, the cassette may include active components, for example a motor or other actuator, light emitters for sensing, or other components.

As are visible in FIG. 27A, one or more light emitters 2706 and light receivers 2707 are positioned near the bottom of dispenser 2701. In operation, light from light emitters 2706 reflects from reflective surface 2708 (visible in FIG.

27B) and returns to light receivers 2707, so long as it is not interrupted by an item being dispensed and falling through the "light curtain" formed across opening. When an item is dispensed through opening 2604, it interrupts the light received by any of light receivers 2707, and dispenser 2701 can note that an item has in fact been dispensed. If no light interruption is detected despite a command to dispense an item, computer 103 may assume that a misfeed or other problem has occurred, or that cassette 2702 is empty. By using more sophisticated monitoring strategies, accidental dispensing of multiple items may be detected. For example, if two interruptions of the light curtain are detected closely spaced in time, a double feed may be indicated. Emitter 2706 may be of any suitable type of emitter, and may emit light in any suitable wavelength or combinations of wavelengths. For example, light emitter 2706 may be a light emitting diode, a laser such as a vertical cavity semiconductor emitting laser (VCSEL) or another kind of light source, and may emit visible light, infrared light, or light in other suitable wavelength bands or combinations of wavelength bands. In other embodiments, surface 2708 may be non-reflective, for example black, and the dispensing of an item may be detected by noting an increase in the intensity of light reaching receivers 2707, rather than a decrease, as light is reflected from the item being dispensed.

In other embodiments, light emitters 2706 and receivers 2707 may be on opposite sides of opening 2604, so that receivers 2707 receive light directly from light emitters 2706 until the light is interrupted by the dispensing of an item.

Figure 28:
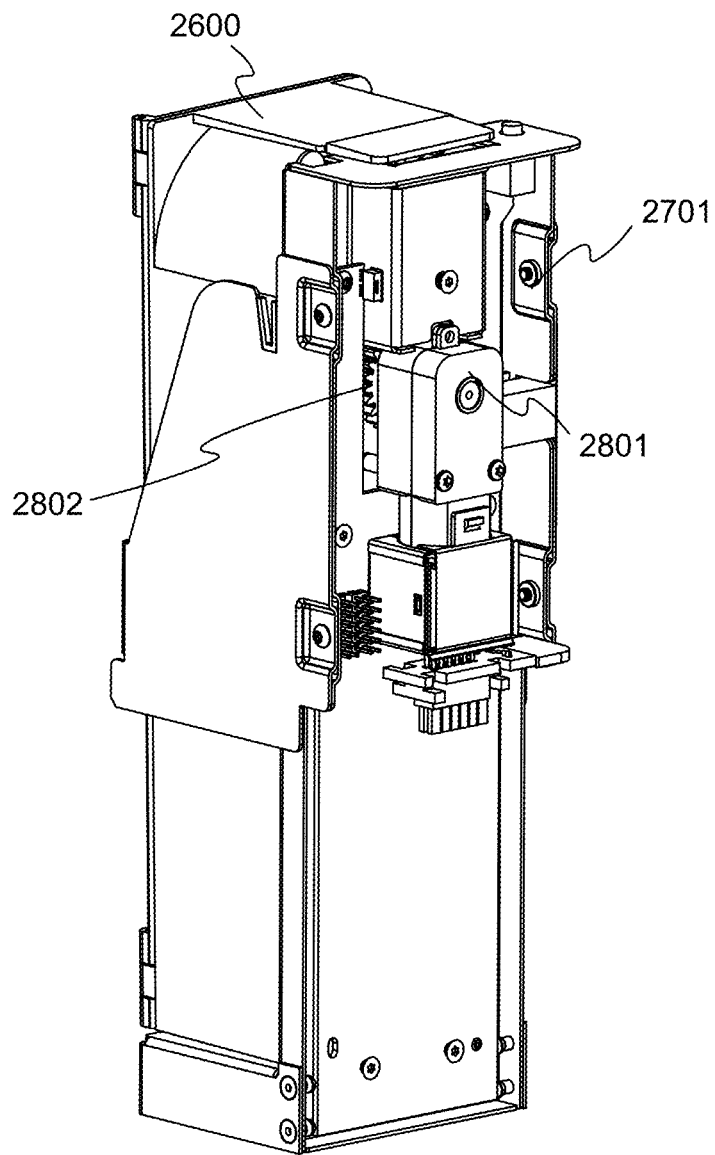
FIG. 28 shows a partially cutaway oblique view of the dispensing mechanism of FIGS. 26A and 26B.

FIG. 28 shows an oblique view of dispensing mechanism 2600 with some parts removed, revealing some internal details of dispenser 2701. A motor 2801 having a right-angle drive turns driving gear 2802, which engages gear 2703 on cassette 2702 to actuate cassette 2702. Motor 2801 may be, for example, a stepper motor whose angular position can be readily moved incrementally and held. In that case, an item may be dispensed by advancing motor 2801 by a number of steps known to correspond to one dispensing operation. If the light curtain does not detect that an item is dispensed, motor 2801 may be advanced further, and if no dispensing is yet detected, an error message may be generated, or it may be assumed that cassette 2702 is empty. Alternatively, motor 2801 may be a simple DC or AC motor, in which case dispensing may be accomplished by simply running motor 2801 until the dispensing of an item is detected, and then shutting off the motor so that motor 2801 is advanced incrementally as far as is needed. A time limit may be imposed, such that if no dispensing is detected within the time limit with motor 2801 running, the motor may be shut off and an error message generated.

In other embodiments, an actuator other than a motor may be used. For example, a solenoid or memory metal actuator may provide a reciprocating motion that is used to drive the driving gear within dispenser 2701 using a ratchet or ratchet-like arrangement. Other kinds of actuators and driving arrangements are possible.

A microprocessor, microcontroller, or similar controlling circuitry may reside within dispenser 2701, and may operate the various active components and sensors of dispenser 2701 in response to high-level commands from a supervisory controller elsewhere within restock drawer 106, or from computer 103. In that case, dispenser 2701 is considered a "smart" dispenser, because it includes some processing intelligence. However, other architectures are possible. For example, logic signals from a supervisory controller elsewhere within restock drawer 106 may operate dispenser 2701.

Figure 29:
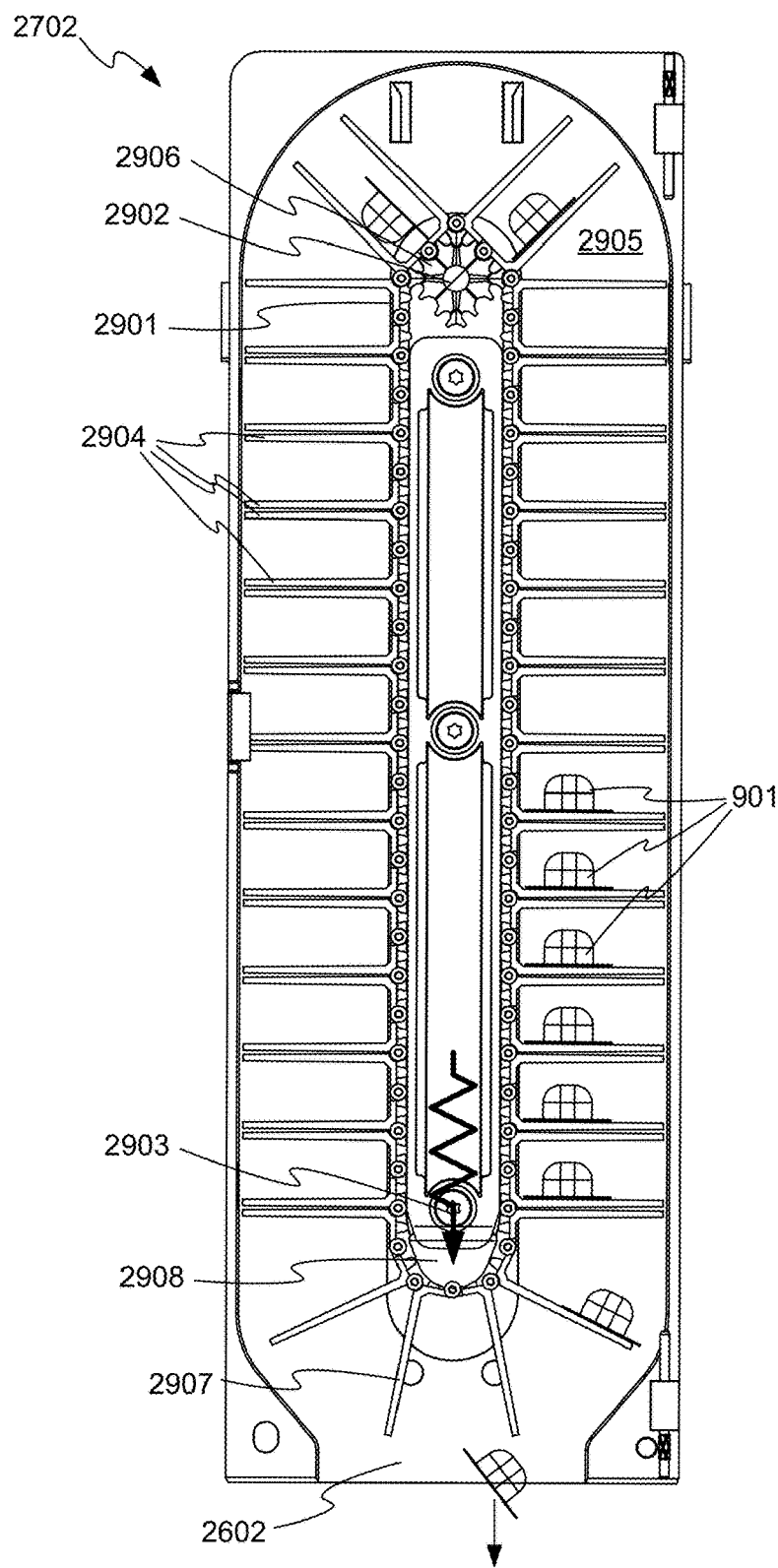
FIG. 29 shows an orthogonal view of a cassette portion of the dispensing mechanism of FIGS. 26A and 26B, with a back cover removed to show some internal workings of the cassette.

FIG. 29 shows an orthogonal view of cassette 2702, with its back cover removed, and showing the internal workings of the cassette. A segmented belt 2901 is supported between drive shaft 2902 and idler shaft 2903. Drive shaft 2902 is connected to gear 2802, such that belt 2901 is driven by gear 2802, and ultimately by motor 2801. Motor 2801 (and thus belt 2901) may be driven in either direction. Paddles 2904 are integrally formed with segments of belt 2901, and form links in belt 2901. Paddles 2904 circulate within chamber 2905 as belt 2901 moves. A sprocket 2906 turns with drive shaft 2902 to drive belt 2901, providing positive relationship between the angular position of drive shaft 2902 and the travel of belt 2901.

The spaces between paddles 2904 form a number of storage compartments, some of which are filled with blister packs 901. To dispense an item, belt 2901 is incrementally advanced until the bottommost paddle 2904 holding an item approaches a vertical orientation, as shown by paddle 2907, and the item falls by gravity through opening 2602 to dispense drawer 107.

While chamber 2905 is shown as being oriented vertically (being taller than it is wide), this is not a requirement. A dispensing mechanism according to embodiments of the invention may also position a chamber in a horizontal orientation (being wider than it is tall).

Sprocket 2906 is non-circular. That is, its cross section taken perpendicular to its axis of rotation is not circular. In the example of FIG. 29, sprocket 2906 has a square cross section.

Figure 30:
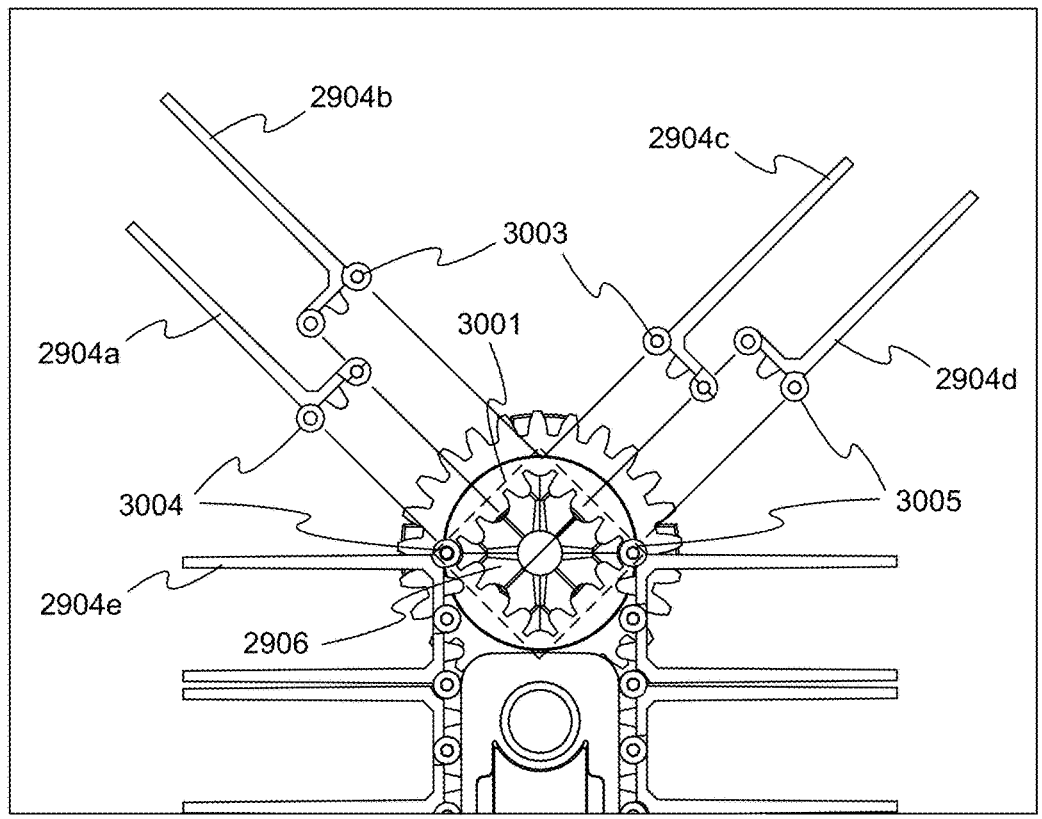
FIG. 30 shows a partially exploded view of the cassette of FIG. 29.

FIG. 30 shows sprocket 2906 and several paddles in a partially exploded view. Sprocket 2906 is outlined in dashed lines 3001 to show its square cross section. Particular paddles 2904a, 2904b, 2904c, and 2904d have been moved from their assembled positions, for clarity of explanation. Each of paddles 2904a-2904d is L-shaped. Paddles 2904a and 2904b join together, for example using pins, at the tips 3002 of their L shapes, and paddles 2904b and 2904c join together at the corners 3003 of their L shapes. Similarly paddles 2904a and 2904e are joined at their corners 3004, and paddles 2904d and 2904f are joined at their corners 3005. Thus, the paddles are joined together in alternating orientation along the length of belt 2901.

Figure 31:
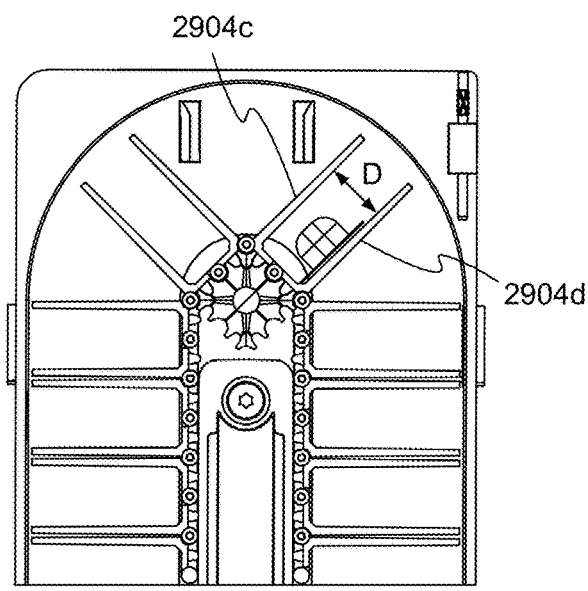
FIG. 31 illustrates the spacing between parts of the cassette of FIG. 29.

This arrangement allows the adjacent pairs of paddles defining compartments for holding items to be dispensed to remain closer together as they traverse the top of cassette 2702 than if sprocket 2906 were round. The spacing between paddles 2904c and 2904d is labeled "D" in FIG. 31. The paddles do not necessarily maintain parallelism through their traversal of the top of cassette 2702, but remain closer than if sprocket 2906 were round. This arrangement may reduce the possibility of jamming of the cassette mechanism.

Referring again to FIG. 29, a spring-loaded idler 2908 maintains tension on belt 2901, and takes up the unevenness of the travel of belt 2901 over square sprocket 2906.

The use of paddles 2904 in this manner provides the ability to store a large number of items to be dispensed, in comparison with prior cassette designs, for example the prior helical screw dispenser. Example cassette 2702 uses 28 pairs paddles 1004, providing storage for up to about 26 items between paddles 2904. More or fewer paddles 2904 could be used, providing a different number of storage spaces, depending on the sizes of the items to be placed in and dispensed from the cassette. While other dimensions are possible, example cassette 2702 is approximately 251 mm tall, 72 mm wide, and 49 mm deep, and thus displaces a volume of less than 900 cubic centimeters, or about 34.6 cubic centimeters for each item that can be stored in cassette 2702. In other embodiments, more items may be stored by placing paddles 2904 closer together, making paddles 2904 smaller, or by other miniaturization techniques. For example, in various embodiments, cassette 2702 may displace, less than 30, less than 25, less than 20, less than 15, or less than 10 cubic centimeters for each item stored in cassette 2702 at full capacity.

In some embodiments, dispensing mechanism 2600 may include one or more sensors for directly detecting movement of a mechanical component of dispensing mechanism 2600. For example, the driving gear within dispenser 2701 may have holes around its main portion, so that the remaining material between the holes functions as broad spokes. A reflective optical sensor may be provided within dispenser 2701 that shines light (for example infrared light) onto the driving gear and can detect whether a return reflection is received. Rotation of the gear then results in an alternating signal from the sensor as the reflective "spokes" and the non-reflective holes alternately pass the sensor. A processor or other circuitry within dispenser 2701 can interpret this signal to verify the motion of the driving gear. This direct measurement provides additional feedback as to the operation of dispensing mechanism 2600. For example, if it is verified using the additional sensor that belt 2901 has moved sufficiently far that an item should be dispensed, but the light curtain sensor does not detect the dispensing of an item, it may be determined that cassette 2702 is empty, or it may be suspected that an error has occurred.

Other kinds of sensors could be used to directly measure mechanical motion. For example, the passing of paddles 2904 may be detected by a reflective optical sensor shining light through an opening the wall of chamber 2905. Preferably, any active parts of the sensing system reside in dispenser 2701, so that cassette 2702 does not include active electrical components.

Figure 32:
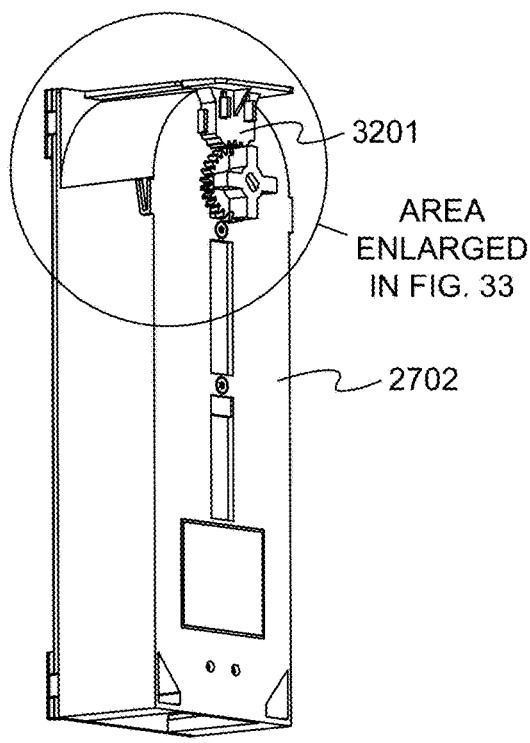
FIG. 32 shows a rear oblique view of the cassette of FIG. 29.
Figure 33:
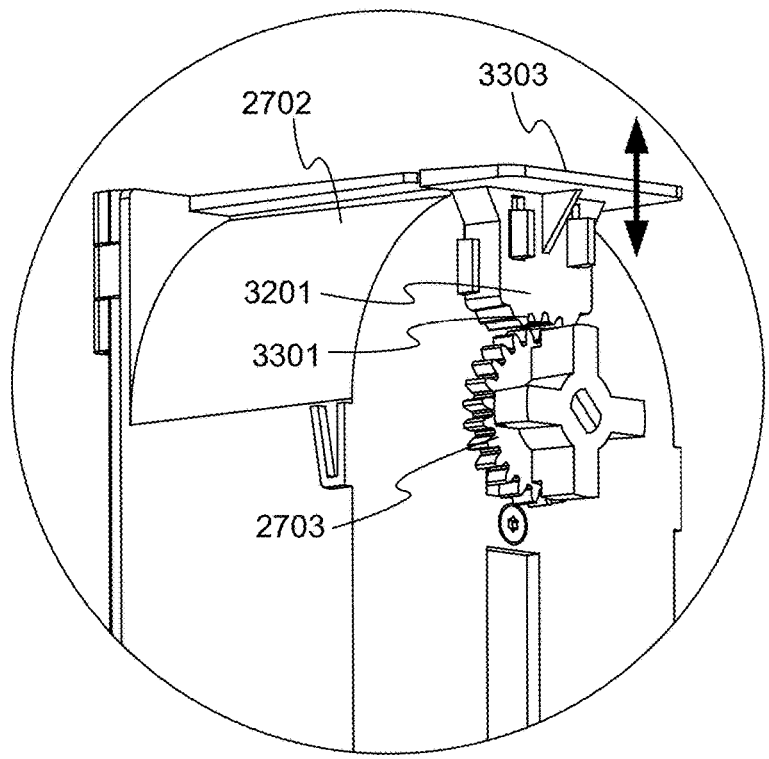
FIG. 33 shows a magnified view of part of FIG. 32.

FIG. 32 shows a rear oblique view of cassette 2702, and FIG. 33 shows a magnified view of part of FIG. 32. FIGS. 32 and 33 illustrate a brake 3201. Brake 3201 is normally engaged, and hinders movement of belt 2901 when engaged. In this example, teeth 3301 in brake 3201 engage with the teeth of gear 2703 on cassette 2702. This may be helpful, for example, during shipment or transport of a full cassette, to prevent intentional or accidental removal of items from cassette 2702 by turning gear 2703.

Preferably, brake 3201 disengages automatically when cassette 2702 in installed into dispenser 2701. For example, tab 3303 on brake 3201 may contact the top of dispenser 2701 as cassette 2702 is installed into dispenser 2701, lifting brake 3201 out of engagement with gear 2703.

Figure 35:
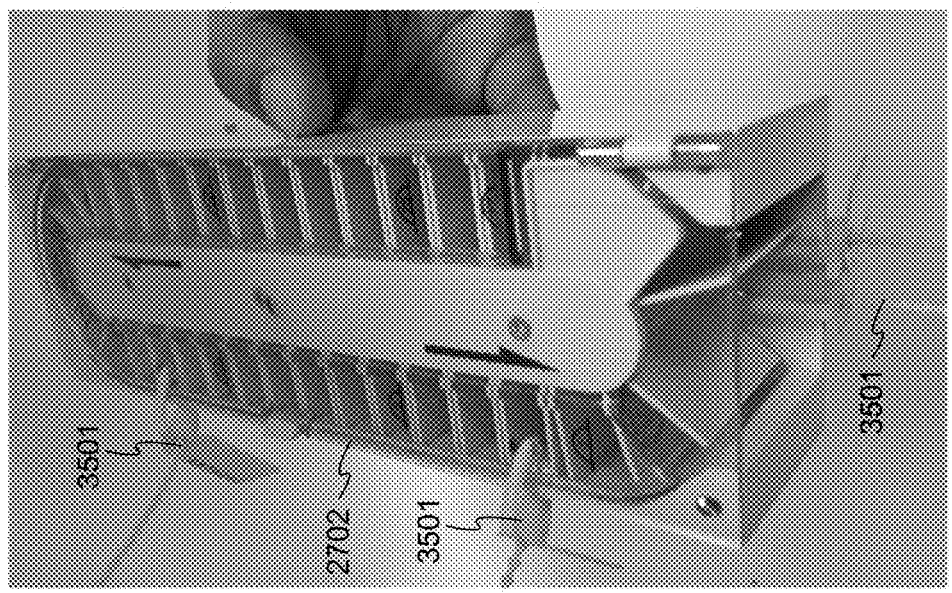
FIG. 35 illustrates a number of ties installed in the openings shown in FIG. 34.
Figure 34:
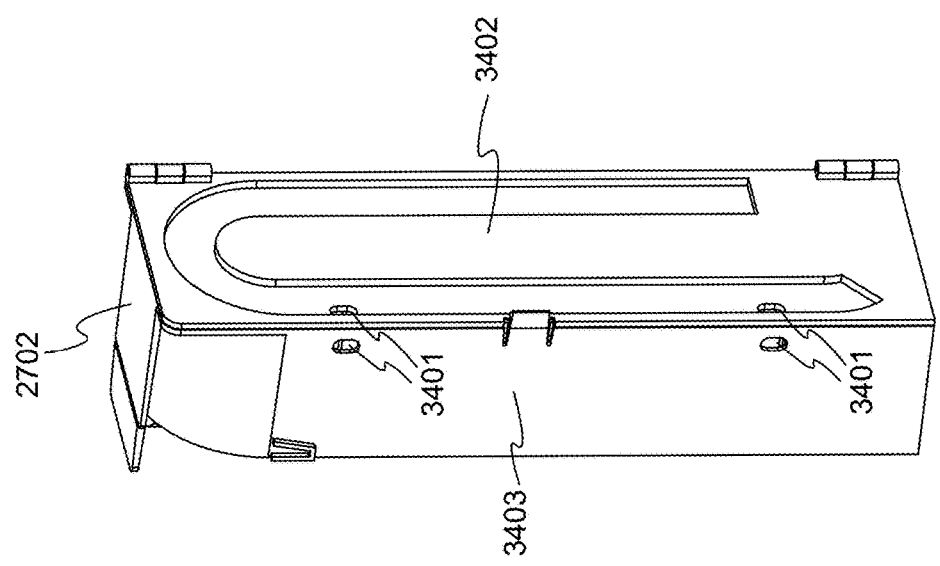
FIG. 34 illustrates the locations of several openings in the cassette of FIG. 29, in accordance with embodiments of the invention.

Other measures may be taken to prevent accidental or intentional diversion of items from cassette 2702. For example, as shown in FIG. 34, openings 3401 may be provided in back 3402 and side 3403 of cassette 2702, to accommodate tamper-evident ties that also disable the operation of cassette 2702. FIG. 35 shows cassette 2702 (with back 3402 removed) with several ties 3501 installed. Ties 3501 may be, for example, plastic "zip" ties or a similar kind of tie, that is not conveniently removable without cutting the tie. Ties 3501 may be installed when cassette is filled, and not legitimately removed until cassette 2702 is ready to be installed in a drawer such as drawer 106. If cassette 2702 arrives at its destination with all of ties 3501 intact, it may be assumed that no tampering or accidental dispensing has occurred. If any of ties 3501 is missing or damaged, diversion may be suspected. When a decision is made to install cassette 2702 in a dispenser or drawer, the restock technician can cut ties 3501 before installation.

Other kinds of tamper-evident mechanisms may be used as well, instead of or in addition to ties 3501.

Additional Dispensing Mechanism for Vials and Other Similarly-Shaped Items

Figure 36B:
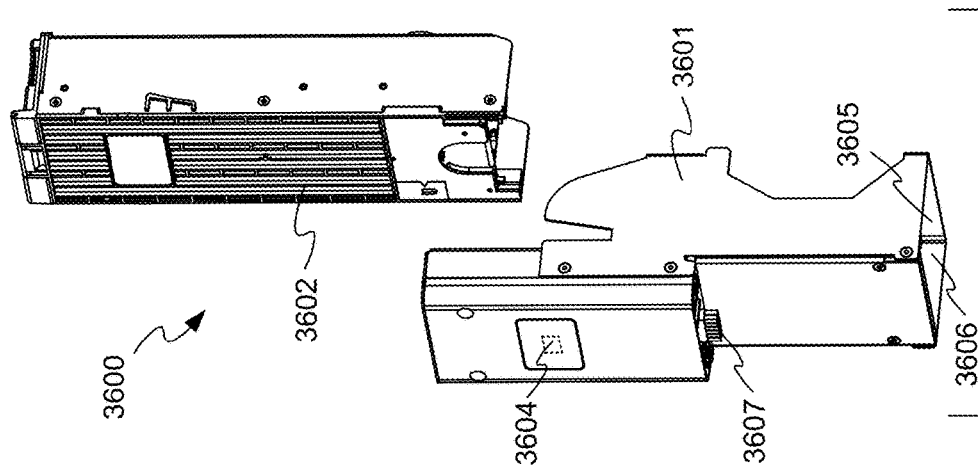
FIGS. 36A and 36B illustrate upper and lower partially exploded oblique views of a dispensing mechanism, in accordance with other embodiments of the invention.
Figure 36A:
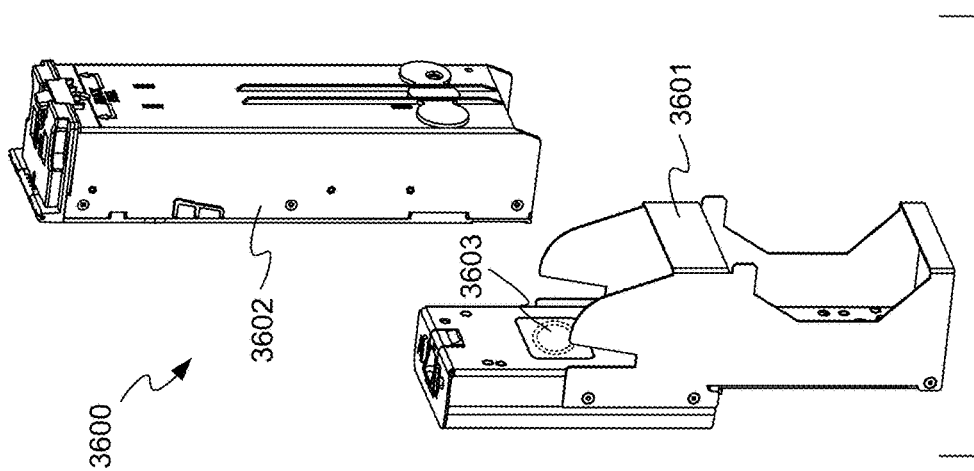

FIGS. 36A and 36B illustrate upper and lower partially exploded oblique views of a dispensing mechanism 3600, in accordance with embodiments of the invention. Dispensing mechanism 3600 is similar in some ways to dispensing mechanism 204 described above, and may be especially useful in dispensing vials such vial 1301 shown in FIG. 13, having a protruding cylindrical top 1302. Vial 1301 may be used, for example, for storing fluids for loading into a hypodermic syringe for injection into a patient. Other similarly-shaped items may also be dispensed by dispensing mechanism 3600.

Referring again to FIGS. 36A and 36B, example dispensing mechanism includes a dispenser 3601 and a cassette 3602, which may be easily separable for restocking dispensing mechanism 3600.

Preferably, cassette 3602 does not contain any active electrical components. All of the active components of dispensing mechanism 3600 reside in dispenser 3601. For example, an antenna 3603 can excite a passive memory chip 3604 in cassette 3602, to determine the contents of cassette 3602 (written into passive memory chip 3604 when cassette 3602 was filled at a remote location). If desired, antenna 3603 can also be used to update the data in passive memory chip 3604. This wireless data exchange may use any suitable wireless protocol, for example Near Field Communications (NFC), radio frequency identification (RFID), or another wireless protocol.

Dispenser 3601 can preferably automatically detect the installation and removal of cassette 3602. This automatic detection may facilitate the inventory and tracking of items, and also can help prevent illicit diversion of items. The detection may be accomplished in any suitable way, for example periodic polling using antenna 3603, a contact sensor (not shown) that can detect the presence of cassette 3602 electromechanically, or by another technique. Dispensing mechanism 3600 may be removably secured to one of rails 201 using a snap mechanism, one or more screws, or by another method.

In other embodiments, a dispensing mechanism in accordance with embodiments of the invention may not have the separable architecture of dispensing mechanism 3600, but may be a single unit including space for storing items to be dispense and including the actuator and other components for dispensing items. In other embodiments that do include a cassette, the cassette may include active components, for example a motor or other actuator, light emitters for sensing, or other components.

Although not visible in FIGS. 36A and 36B, a light emitter and light receivers are positioned near the bottom of dispenser 3601, and operate similarly to light emitter 706 and receivers 707 described above with respect to dispensing mechanism 202. In operation, light from the light emitter reflects from reflective surface 3605 (visible in FIG. 12B) and returns to the light receivers, so long as it is not interrupted by an item being dispensed and falling through the "light curtain" formed across opening 3606. When an item is dispensed through opening 3606, it interrupts the light received by either or both light receivers, and dispenser 3601 can note that an item has in fact been dispensed. If no light interruption is detected despite a command to dispense an item, computer 103 may assume that a misfeed or other problem has occurred, or that cassette 3602 is empty. By using more sophisticated monitoring strategies, accidental dispensing of multiple items may be detected. For example, if two interruptions of the light curtain are detected closely spaced in time, a double feed may be indicated. In other embodiments, surface 3605 may be non-reflective, for example black, and the dispensing of an item may be detected by noting an increase in the intensity of light reaching the receivers, rather than a decrease, as light is reflected from the item being dispensed.

In other embodiments, the light emitters and receivers may be on opposite sides of opening 3606, so that the receivers receive light directly from the light emitters until the light is interrupted by the dispensing of an item.

As is visible in FIG. 36B, a connector 3607, compatible with connectors 302 on rails 201, is positioned to engage one of connectors 302 when dispensing mechanism 3600 is installed in restock drawer 106. Although not shown in FIGS. 36A and 36B, dispensing mechanism 3600 may include a button and light similar to button 601 and light 602 discussed above, for communication between a restocking technician or other user and computer 103 of cabinet 100.

Figure 37:
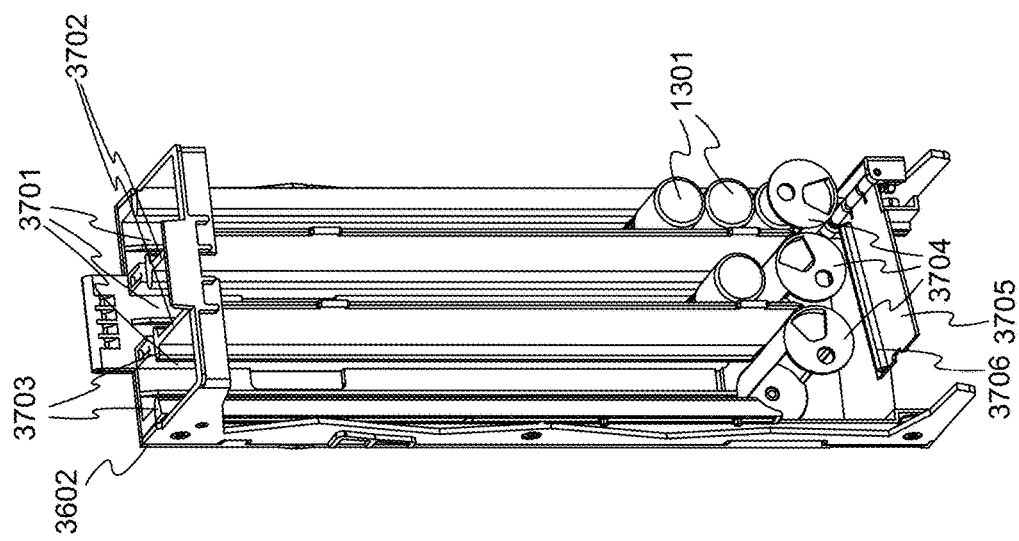
FIG. 37 is a cutaway oblique view of example a cassette partially filled with vials, in accordance with embodiments of the invention.

FIG. 37 is a cutaway oblique view of example cassette 3602, partially filled with vials 1301, and with the top of cassette 3602 removed. As is visible in FIG. 37, cassette 3602 includes a number of vertical channels 3701 of a shape and size to receive a number of vials 1301 and hold the vials in vertical stacks. In cassette 3602, three vertical channels 3701 are present, and vials 1301 are 2 ml vials, having a diameter of about 15 mm, and a height of about 35.5 mm. While other dimensions may be used, example cassette 3602 is about 232 mm high, 72 mm wide, and 54 mm deep (displacing about 902 cubic centimeters), and can hold about 30 vials of the 2 ml size. Thus, example cassette 3602 displaces less than 31 cubic centimeters for each vial that can be stored in cassette 3602. In other uses, 1 ml vials may be used, having a diameter of about 15 mm, in which case cassette 3602 may hold a similar number of vials. Other vial sizes may be used as well. Walls 3702 divide the stacks of vials, and protrusions 3703 may help constrain the vials by their necks. In various embodiments, cassette 3602 may displace less than 30, less than 25, less than 20, or less than 15 cubic centimeters for each vial stored in cassette 3602 at full capacity.

Cassette 3602 also includes a number of open-sided rotatable receivers 3704 at the bottom of vertical channels 3701.

Figure 38:
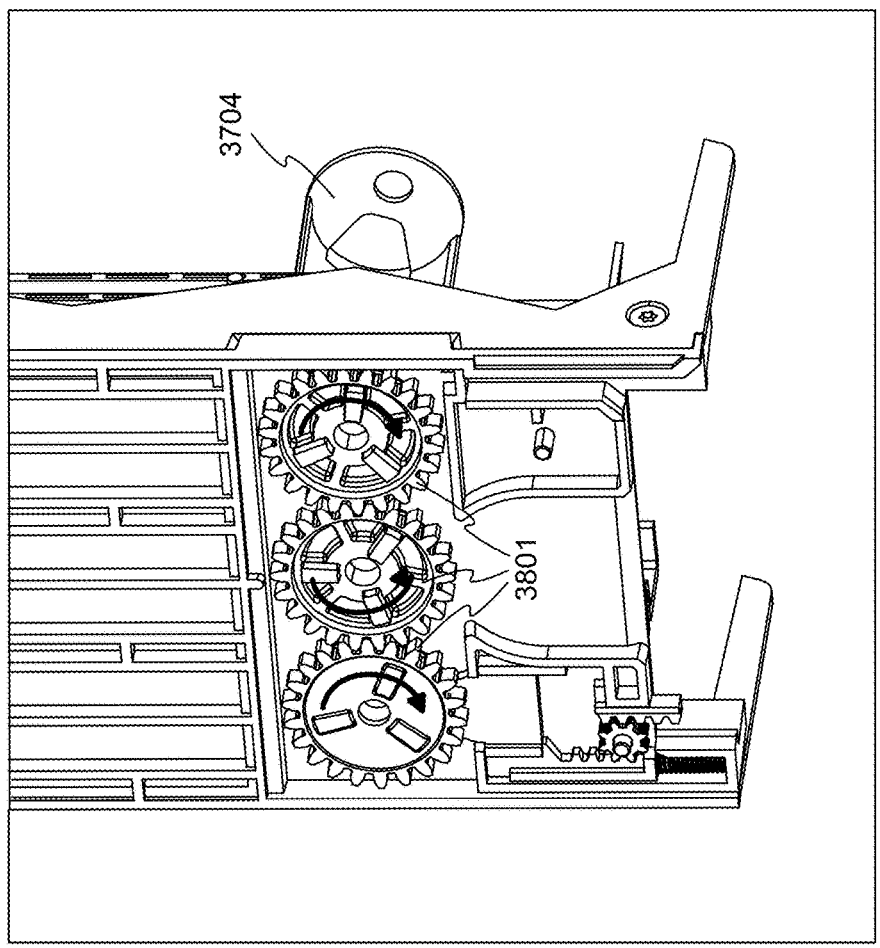
FIG. 38 illustrates a lower oblique rear view of the cassette of FIG. 37.

FIG. 38 illustrates a lower oblique rear view of cassette 3602, showing a set of gears 3801, each of which is coupled to one of open-sided rotatable receivers 3704. Gears 3801 mesh, so that receivers 3704 rotate in synchronization.

Figure 39B:
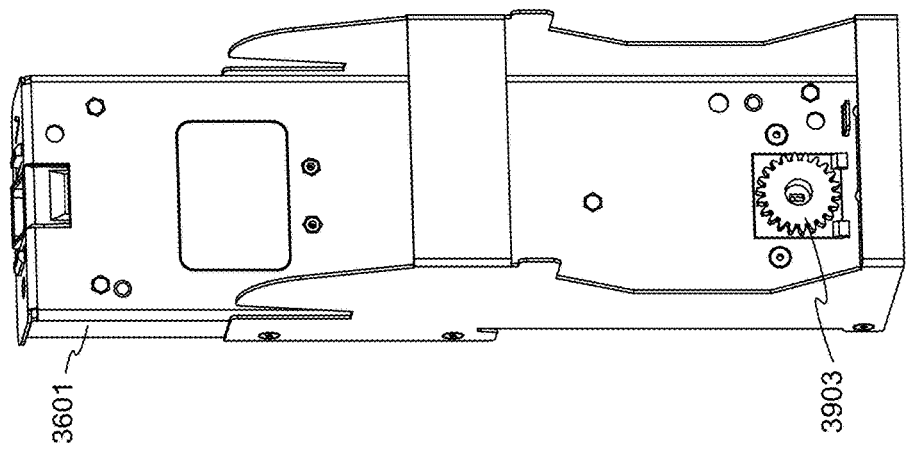
FIG. 39B illustrates an oblique front view of the dispenser.
Figure 39A:
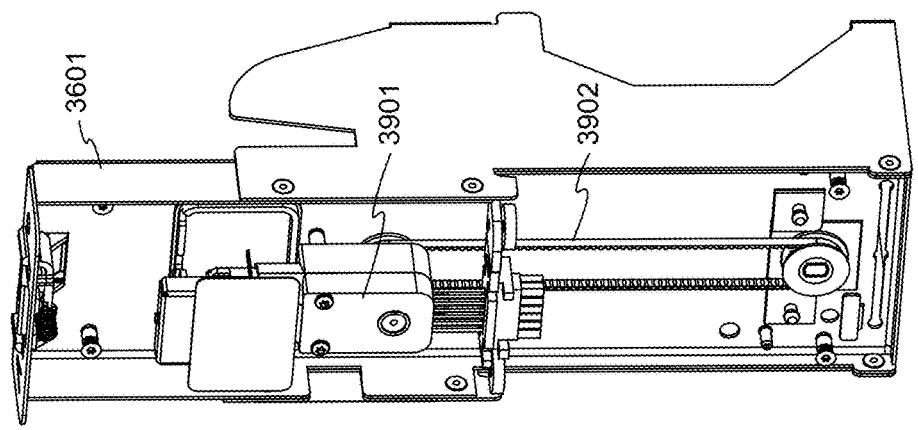
FIG. 39A illustrates a partially-cutaway rear view of a dispenser in accordance with embodiments of the invention.

FIG. 39A illustrates a partially-cutaway rear view of dispenser 3601, and FIG. 39B illustrates an oblique front view of dispenser 3601. Referring to both FIGS. 39A and 39B, a motor 3901 drives a belt 3902, which in turn drives gear 3903. Motor 3901 may be, for example, a stepper motor or a simple DC or AC motor, operated in the manner described above in relation to dispensing mechanism 202. That is, motor 3901 may be incrementally advanced either by control of the steps of a stepper motor, or by running motor 3901 only until the dispensing of an item is detected. In other embodiments, an actuator other than a motor may be used. For example, a solenoid or memory metal actuator may provide a reciprocating motion that is used to drive the gear within dispenser 3601 using a ratchet or ratchet-like arrangement. Other kinds of actuators and driving arrangements are possible.

When dispenser 3601 and cassette 3602 are engaged, gear 3903 meshes directly or indirectly with gears 3801 of cassette 3602, to turn open-sided rotatable receivers 3704. Referring again to FIGS. 37 and 38, gears 3801 rotate in synchronization. While a rotation direction is shown for ease of explanation, the choice of rotation direction is arbitrary, and either direction may be used.

As the gears rotate, the respective open sides of receivers 3704 "take turns" reaching an upward vertical orientation and a downward vertical orientation. For example, the three gears of example cassette 3602 are meshed in such a way that one of the receivers reaches the upward vertical orientation for every 120 degrees of rotation of gears 3801. If different numbers of gears are present, then a different angular separation of the gear positions may be used, but preferably receivers 3704 reach the downward vertical orientation at evenly spaced angular intervals gears 3801.

When one of the receivers reaches its upward vertical orientation and at least one vial is present in the corresponding vertical channel of cassette 3602 (not shown), the vial is free to drop into the respective receiver 3704. As the gears continue to turn, the receivers 3704 alternately reach their upward positions to receive vials, and reach their downward positions to dispense vials. Thus, the vials in cassette 3602 can be dispensed one by one.

In some embodiments, dispensing mechanism 3600 may include one or more sensors for directly detecting movement of a mechanical component of dispensing mechanism 3600. For example, the driven gear within cassette 3602 may have holes around its main portion, so that the remaining material between the holes functions as broad spokes. A reflective optical sensor may be provided within dispenser 3601 that shines light (for example infrared light) onto the driven gear and can detect whether a return reflection is received. Rotation of the gear then results in an alternating signal from the sensor as the reflective "spokes" and the non-reflective holes alternately pass the sensor. A processor or other circuitry within dispenser 3601 can interpret this signal to verify the motion of the driven gear. This direct measurement provides additional feedback as to the operation of dispensing mechanism 3600. For example, if it is verified using the additional sensor that the gear has moved sufficiently far that an item should be dispensed (120 degrees in the example embodiment), but the light curtain sensor does not detect the dispensing of an item, it may be determined that cassette 3602 is empty, or it may be suspected that an error has occurred.

Other kinds of sensors could be used to directly measure mechanical motion. For example, the teeth of gears 3801 may be visible to a reflective optical sensor shining light through an opening the wall of dispenser 3601, and the rotation of the gears may be detected by monitoring the passing of the individual gear teeth. Preferably, any active parts of the sensing system reside in dispenser 3601, so that cassette 3602 does not include active electrical components.

While cassette 3602 is shown as having three vertical channels 3701, other numbers of channels may be used. For example, an alternate cassette may have two vertical channels, and may be suitable for dispensing 5 ml vials having a diameter of about 25 mm.

Referring again to FIG. 37, a hinged flap 3705 can be seen below rotatable receivers 3704. Hinged flap 3705 may be lightly spring loaded so that it is normally in an upward position, but can be deflected by the weight of a vial being dispensed. Hinged flap 3705 may serve to absorb some of the energy of a falling vial, and prevent excessive jostling or bouncing of a vial in the dispense drawer. Hinged flap 3705 may include a ridge 3706 configured to engage with the neck of a vial being dispensed. Ridge 3706 may reduce the tendency of a dispensed vial to rotate during dispensing.

Figure 40:
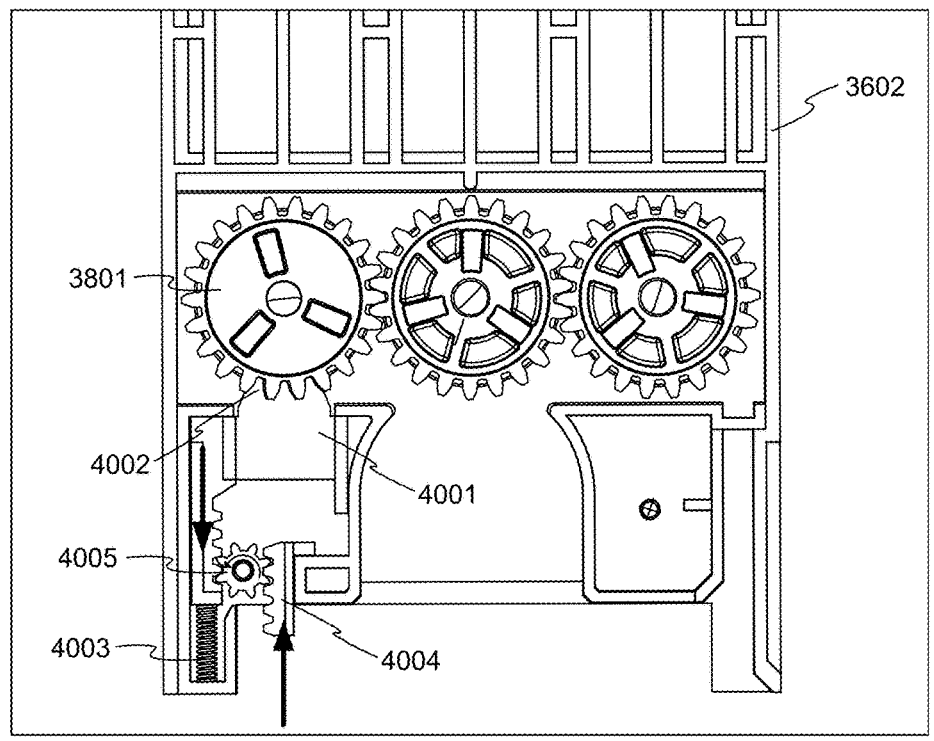
FIG. 40 shows a rear orthogonal view of a lower portion of cassette in accordance with embodiments of the invention, showing the operation of a brake.

FIG. 40 shows a rear orthogonal view of a lower portion of cassette 3602, and illustrates the operation of a brake 4001. Brake 4001 includes gear teeth 4002. When cassette 3602 is installed in dispenser 3601, a part of dispenser 3601 (not shown) pushes rack 4004 upward, which turns gear 4005, and draws brake 4001 downward, out of engagement with gear 3801 so that cassette 3602 can operate to dispense vials or other items. Brake 4001 may be helpful, for example, during shipment or transport of a full cassette, to prevent intentional or accidental removal of items from cassette 3602 by turning gears 3801.

Figure 41:
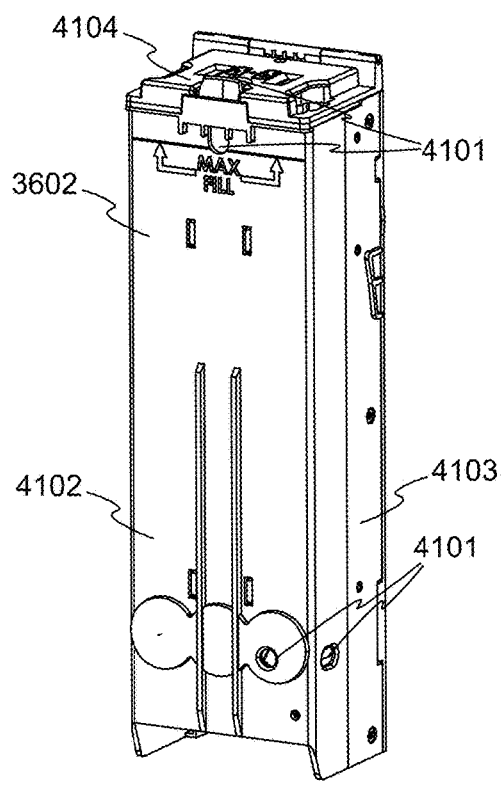
FIG. 41 illustrates the locations of several openings in the cassette of FIG. 37, in accordance with embodiments of the invention.
Figure 42:
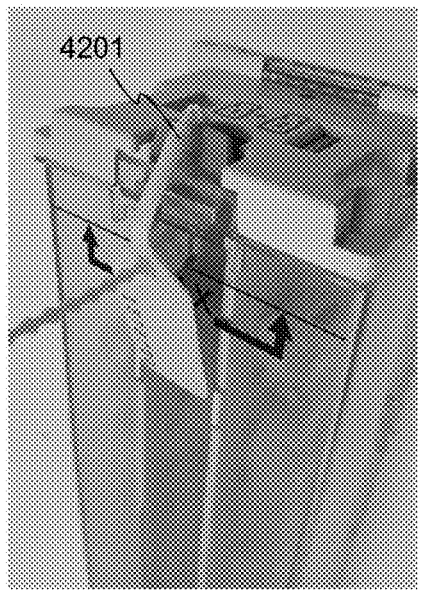
FIGS. 42 and 43 illustrate a number of ties installed in the openings shown in FIG. 41.
Figure 43:
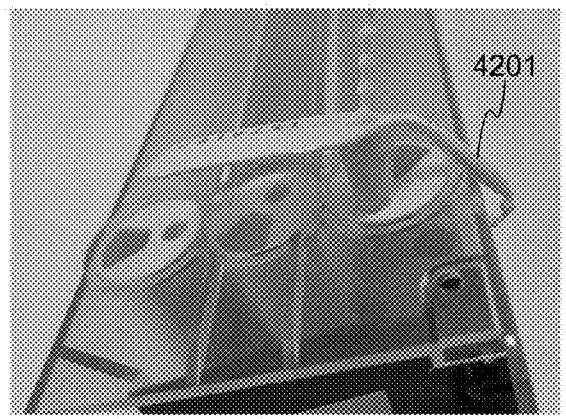

Other measures may be taken to prevent accidental or intentional diversion of items from cassette 3602. For example, as shown in FIG. 41, openings 4101 may be provided in back 4102, side 4103, and top 4104 of cassette 3602, to accommodate tamper-evident ties that also disable the operation of cassette 3602. FIGS. 42 and 43 show cassette 3602 with ties 4201 installed. Ties 4201 may be, for example, plastic "zip" ties or a similar kind of tie, that is not conveniently removable without cutting the tie. Ties 4201 may be installed when cassette is filled, and not legitimately removed until cassette 3602 is ready to be installed in a drawer such as drawer 106. If cassette 3602 arrives at its destination with all of ties 4201 intact, it may be assumed that no tampering or accidental dispensing has occurred. If any of ties 4201 is missing or damaged, diversion may be suspected. When a decision is made to install cassette 3602 in a dispenser or drawer, the restock technician can cut and remove ties 4201 before installation.

Other kinds of tamper-evident mechanisms may be used as well, instead of or in addition to ties 4201.

Additional Dispenser for Syringes and Other Similarly-Shaped Items

Figure 44B:
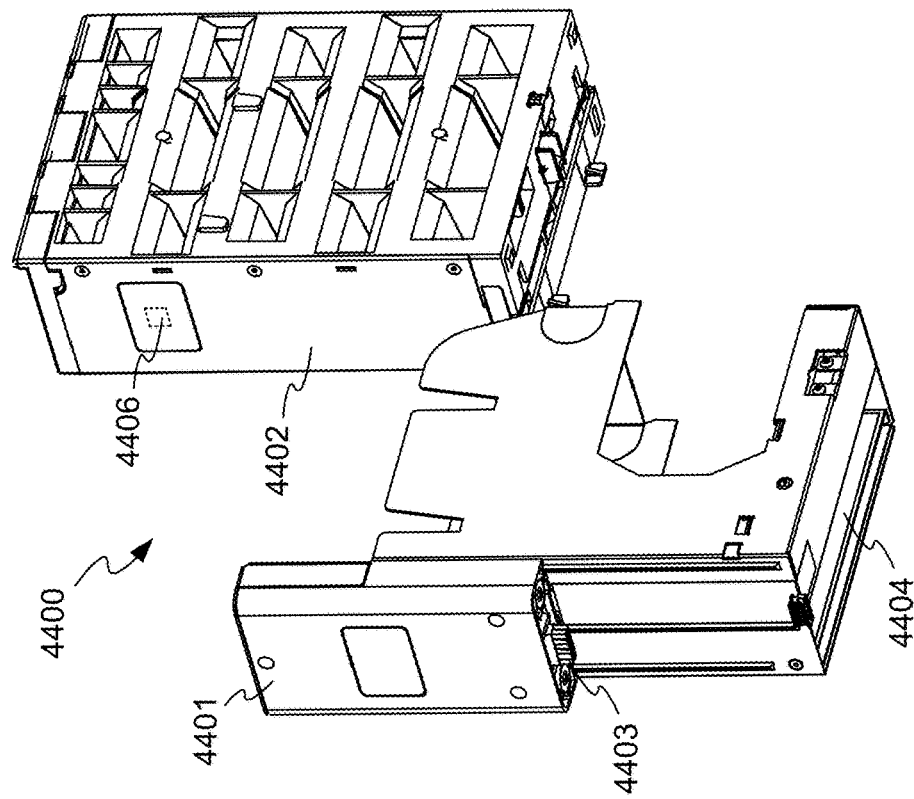
FIGS. 44A and 44B illustrate upper and lower views of a dispensing mechanism in accordance with other embodiments of the invention.
Figure 44A:
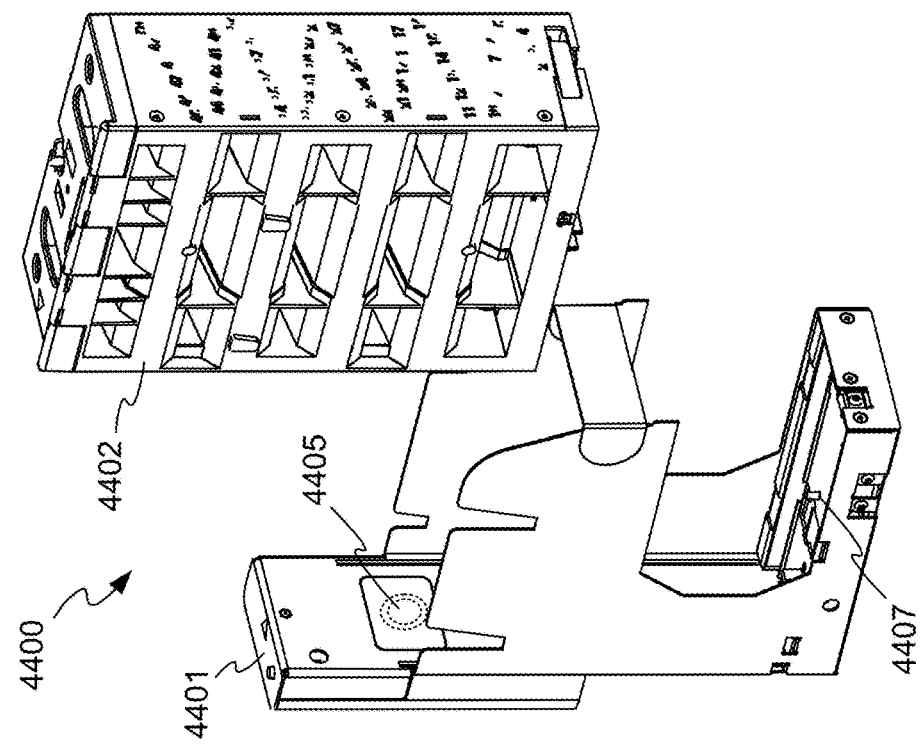

FIGS. 44A and 44B illustrate upper and lower views of a dispensing mechanism 4400 in accordance with embodiments of the invention. Dispensing mechanism 4400 may be especially useful for dispensing cylindrical items such as syringes, although dispensing mechanism 4400 may be useful for dispensing other similarly-shaped items as well.

Example dispensing mechanism 4400 comprises a dispenser 4401 and a cassette 4402, which are separable. For example, dispenser 4401 and cassette 4402 may snap together, may be separable with the removal of one or a small number of screws, or may be reasonably separable in some other way without damage to either dispenser 4401 or cassette 4402. In this way, restocking may be accomplished by replacing a depleted cassette 4402 with a full cassette 4402.

As is visible in FIG. 44B, a connector 4403, compatible with connectors 302 on rails 201, is positioned to engage one of connectors 302 when dispensing mechanism 4400 is installed in restock drawer 106. Dispenser 4401 defines an opening 4404 at the bottom of dispensing mechanism 203, through which items are dispensed. Dispensing mechanism 4400 may be removably secured to one of rails 201 using a snap mechanism, one or more screws, or by another method.

Preferably, cassette 4402 does not contain any active electrical components. All of the active components of dispensing mechanism 4400 reside in dispenser 4401. For example, an antenna 4405 can excite a passive memory chip 4406 in cassette 4402, to determine the contents of cassette 4402 (written into passive memory chip 4406 when cassette 4402 was filled at a remote location). If desired, antenna 4405 can also be used to update the data in passive memory chip 4406. This wireless data exchange may use any suitable wireless protocol, for example Near Field Communications (NFC), radio frequency identification (RFID), or another wireless protocol.

Dispenser 4401 can preferably automatically detect the installation and removal of cassette 4402. This automatic detection may facilitate the inventory and tracking of items, and also can help prevent illicit diversion of items. The detection may be accomplished in any suitable way, for example periodic polling using antenna 4405, a contact sensor (not shown) that can detect the presence of cassette 4402 electromechanically, or by another technique.

The main body of cassette 4402 may be made of a clear material, so that a user can see the contents of cassette 4402.

In other embodiments, a dispensing mechanism in accordance with embodiments of the invention may not have the separable architecture of dispensing mechanism 4400, but may be a single unit including space for storing items to be dispense and including an actuator and other components for dispensing items. In other embodiments that do include a cassette, the cassette may include active components, for example a motor or other actuator, light emitters for sensing, or other components.

Although not shown in FIGS. 44A and 44B, a button and light similar to button 601 and light 602 discussed above, for communication between a restocking technician or other user and computer 103 of cabinet 100.

Figure 45:
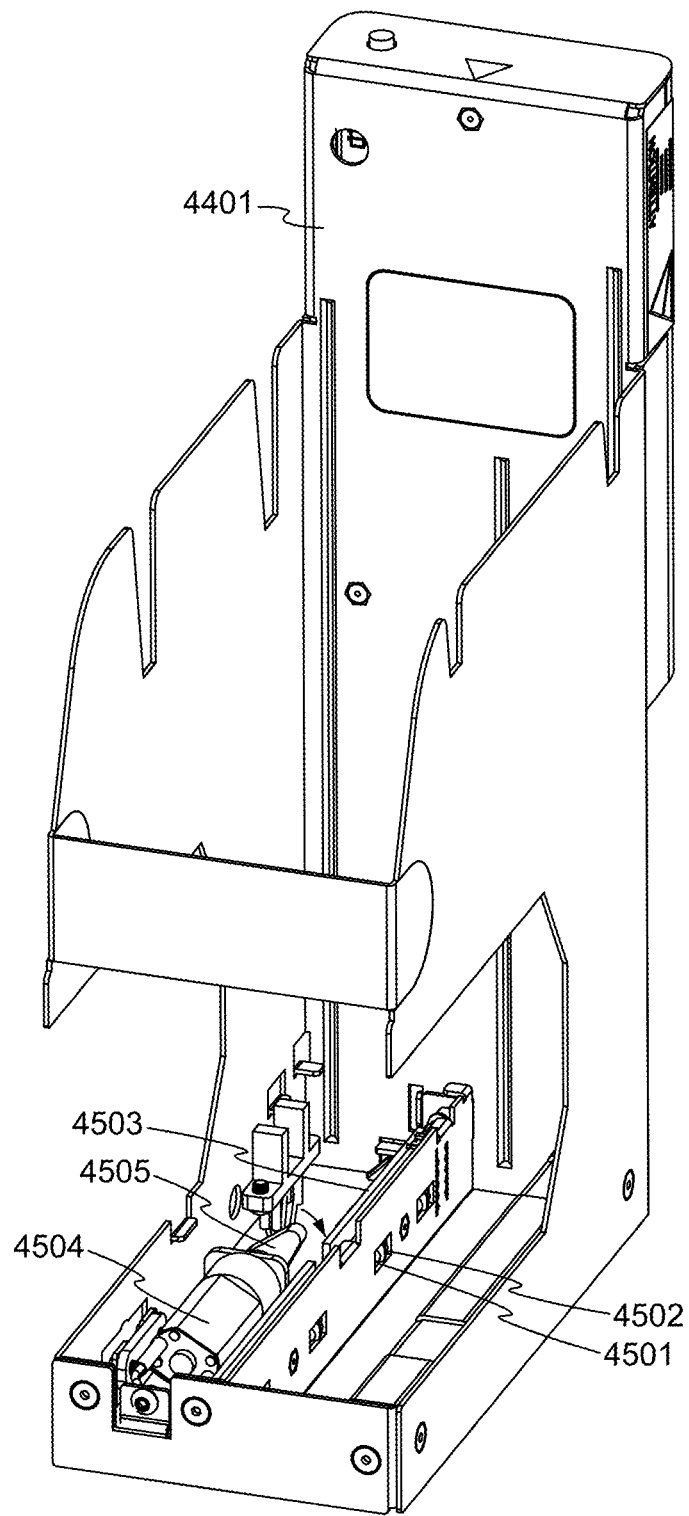
FIG. 45 shows an oblique view of a dispenser in accordance with embodiments of the invention with some parts removed, revealing internal details of the operation of the dispenser.

FIG. 45 shows an oblique view of dispenser 4401 with some parts removed, revealing internal details of the operation of dispenser 4401.

One or more light emitters and receivers 4501, 4502 may be positioned near the bottom of dispenser 4401. In operation, light from light emitters may reflect from a reflective surface of dispenser 4401 (not visible in FIG. 45) and return to the light receivers, so long as it is not interrupted by an item being dispensed and falling through the "light curtain" formed across opening. When an item is dispensed through opening 4404, it interrupts the light received by one or more of the light receivers, and dispenser 4401 can note that an item has in fact been dispensed. If no light interruption is detected despite a command to dispense an item, computer 103 may assume that a misfeed or other problem has occurred, or that cassette 4402 is empty. By using more sophisticated monitoring strategies, accidental dispensing of multiple items may be detected. For example, if two interruptions of the light curtain are detected closely spaced in time, a double feed may be indicated. The one or more light emitters may be of any suitable type of emitter, and may emit light in any suitable wavelength or combinations of wavelengths. For example, a light emitter in an embodiment of the invention may be a light emitting diode, a laser such as a vertical cavity semiconductor emitting laser (VCSEL) or another kind of light source, and may emit visible light, infrared light, or light in other suitable wavelength bands or combinations of wavelength bands. In other embodiments, the surface may be non-reflective, for example black, and the dispensing of an item may be detected by noting an increase in the intensity of light reaching receivers 4502, rather than a decrease, as light is reflected from the item being dispensed.

In other embodiments, light emitters and receivers 4501, 4502 may be on opposite sides of opening 4404, so that receivers 4502 receive light directly from light emitters 4501 until the light is interrupted by the dispensing of an item.

A cable (not visible) couples connector 4403 directly or indirectly with a circuit board 4503, to which a motor 4504 is connected. Motor 4504 may be, for example, a stepper motor whose angular position can be readily moved incrementally and held. In that case, an item may be dispensed by advancing motor 4504 by one rotation. If the light curtain does not detect that an item is dispensed, motor 4504 may be advanced further, and if no dispensing is yet detected, an error message may be generated, or it may be assumed that cassette 4402 is empty. Alternatively, motor 4504 may be a simple DC or AC motor, in which case dispensing may be accomplished by simply running motor 4504 until the dispensing of an item is detected, and then shutting off the motor. A time limit may be imposed, such that if no dispensing is detected within the time limit with motor 4504 running, the motor may be shut off and an error message generated.

Motor 4504 turns a cam 4505 in the direction shown, the function of which is explained in more detail below.

A microprocessor, microcontroller, or similar controlling circuitry may reside within dispenser 4401, and may operate the various active components and sensors of dispenser 4401 in response to high-level commands from a supervisory controller elsewhere within restock drawer 106, or from computer 103. In that case, dispenser 4401 is considered a "smart" dispenser, because it includes some processing intelligence. However, other architectures are possible. For example, logic signals from a supervisory controller elsewhere within restock drawer 106 may operate dispenser 4401.

Figure 46:
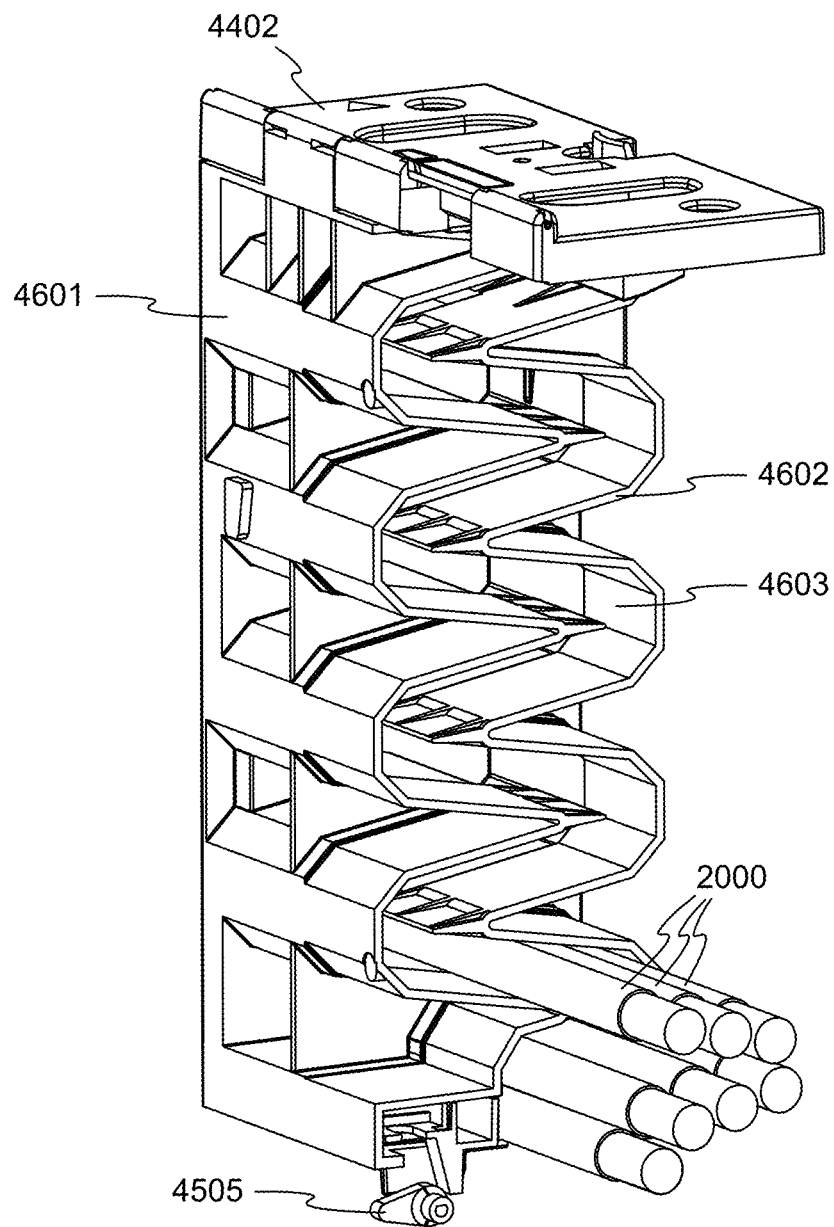
FIG. 46 illustrates a cutaway oblique view of a cassette in accordance with embodiments of the invention.

FIG. 46 illustrates a cutaway oblique view of cassette 4402, and also cam 4505 (which is part of dispenser 4401 rather than cassette 4402). Cassette 4402 is formed by two side pieces 4601 and 4602, which cooperate to define a serpentine channel 4603 between them. A number of syringes 2000 are disposed in serpentine channel 4603, and feed toward the bottom of cassette 4402 as syringes are dispensed. While other dimensions are possible, example cassette 4402 is about 234 mm high, 71 mm deep, and 153 mm wide, and thus displaces an overall volume of less than 2600 cubic centimeters, and can hold up to 50 or more syringes 2000. Cassette 4402 thus displaces about 52 cubic centimeters for each syringe that can be stored in cassette 4402. While syringes 2000 having a 2 ml capacity are shown, cassette 4402 may be configured to dispense syringes having a smaller overall length by placing a spacer (not shown) within cassette 4402. In various embodiments, cassette 4402 may displace less than 50, less than 40, less than 30, or less than 25 cubic centimeters for each item stored in cassette 4402 at full capacity.

Figure 47A:
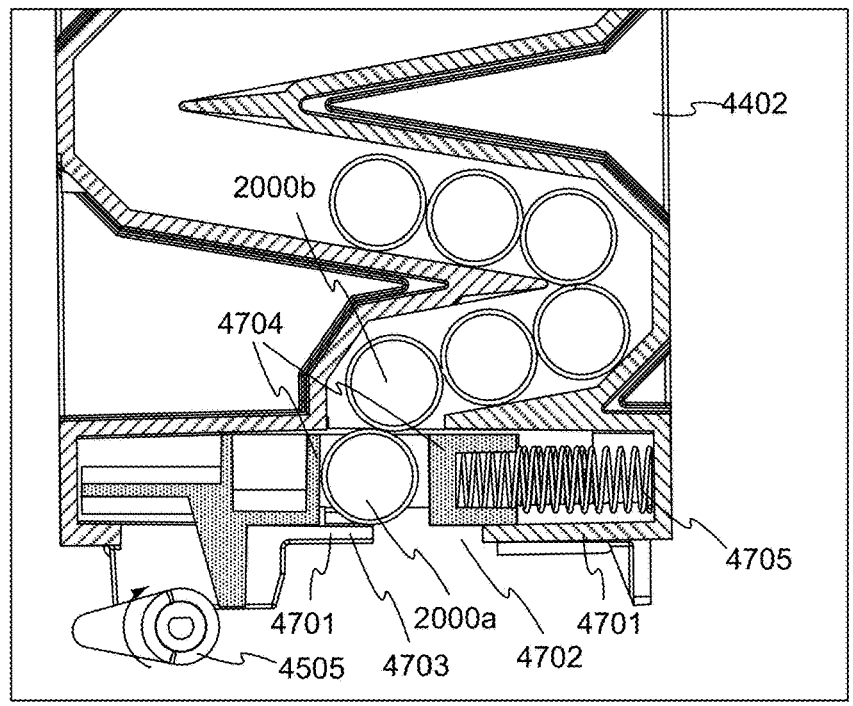
FIGS. 47A-47C show orthogonal section views of the lower part of the cassette of FIG. 46.
Figure 47B:
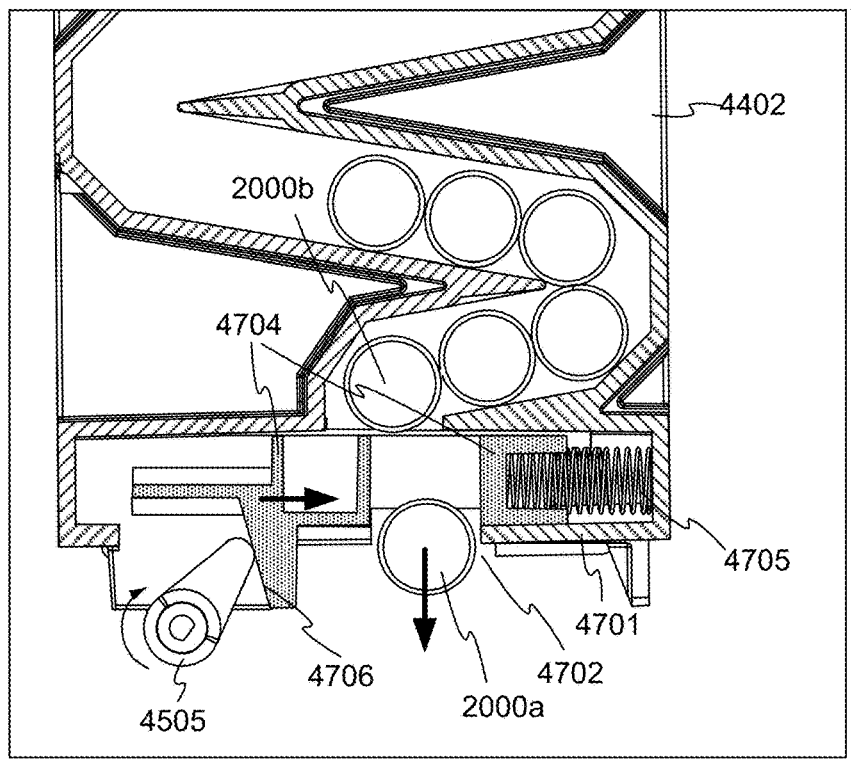
Figure 47C:
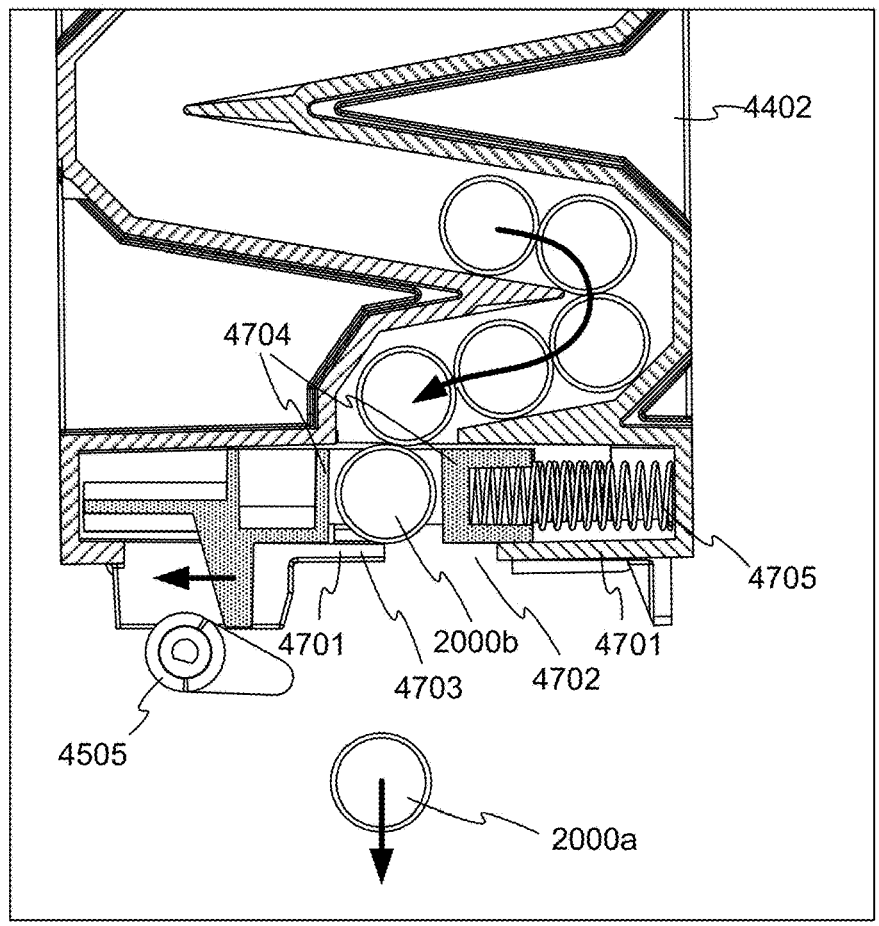

FIGS. 47A-47C show orthogonal section views of the lower part of cassette 4402, as well as cam 4505, and their operation to dispense a syringe 2000. A bottom 4701 of cassette 4402 defines an opening 4702 and a ledge 4703. A movable slide 4704 defines a slot in which syringe 2000a is positioned in FIG. 22A. Slide 4704 is biased to the left by spring 4705, such that syringe 2000a remains suspended by ledge 4703. Syringe 2000a is in position to be dispensed, while cassette 4402 contains additional syringes such as syringe 2000b. Spring 4705 also ensures that the syringes in cassette 4402 are not accidentally dispensed when cassette 4402 is separated from dispenser 4401, for example during transport from a central pharmacy to cabinet 100.

When it is desired to dispense a syringe, motor 4504 (not shown in FIGS. 47A-47C) turns cam 4505 as shown in FIG. 47B. Cam 4505 acts against surface 4706 of slide 4704, moving slide 4704 to the right, aligning the slot in slide 4704 with opening 4702 in bottom 4701 of cassette 4402. Syringe 2000a can accordingly drop through opening 4702 and into dispense drawer 107.

In FIG. 47C, cam 4505 has rotated past its contact with slide 4704, allowing spring 4705 to force slide 4704 back to its nominal position. Sensor electronics may sense the dispensing of syringe 2000a, or that slide 4704 is back to its nominal position, and may shut off motor 4504, stopping cam 4505. Syringe 2000b drops into the slot in slide 4704, resting on ledge 4703, in preparation for its future dispensing.

In other embodiments, an actuator other than a motor may be used. For example, a solenoid or memory metal actuator may provide a translational motion that is used to directly translate slide 4704 against spring 4705. Other kinds of actuators and driving arrangements are possible.

In some embodiments, dispensing mechanism 4400 may include one or more sensors for directly detecting movement of a mechanical component of dispensing mechanism 4400. For example, slide 4704 may be generally non-reflective, but may include a reflective sticker placed for detection by a reflective optical when slide 4704 moves under the action of cam 4505. The passing of the reflective sticker, as detected by the sensor, verifies that slide 4704 has actually moved. A similar effect may be achieved by placing a magnet on slide 4704 and detecting its passing of a Hall Effect sensor. Similarly, the movement of cam 4505 could be directly sensed. A processor or other circuitry within dispenser 4401 can interpret a signal produced by the sensor to verify the motion of the slide or cam. This direct measurement provides additional feedback as to the operation of dispensing mechanism 4400. For example, if it is verified using the additional sensor that slide 4704 has moved sufficiently far that an item should be dispensed, but the light curtain sensor does not detect the dispensing of an item, it may be determined that cassette 4402 is empty, or it may be suspected that an error has occurred.

Figure 48:
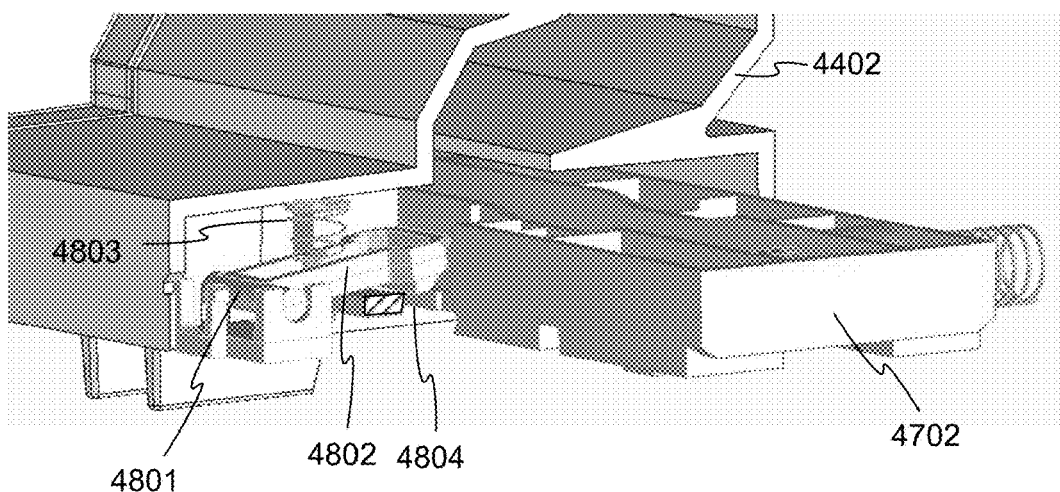
FIG. 48 shows a cutaway oblique view of a portion of the cassette of FIG. 47, and illustrates the operation of a brake.

FIG. 48 shows a cutaway oblique view of a portion of cassette 4402, and illustrates the operation of a brake 4801. Brake 4801 includes a hooked lever 4802. When cassette 4402 is disengaged from dispenser 4401, hooked lever 4802 is biased downward by spring 4803, so that hooked lever 4802 hooks into opening 4804, preventing motion of slide 4704. When cassette 4402 is engaged with dispenser 4401, a feature of dispenser 4401 (for example pin 4407 visible in FIG. 44A) pushes hooked lever 4802 into the upward position shown, so that slide 4704 can move freely. Brake 4801 may be helpful, for example, during shipment or transport of a full cassette, to prevent intentional or accidental removal of items from cassette 4402 by moving slide 4704.

Figure 49B:
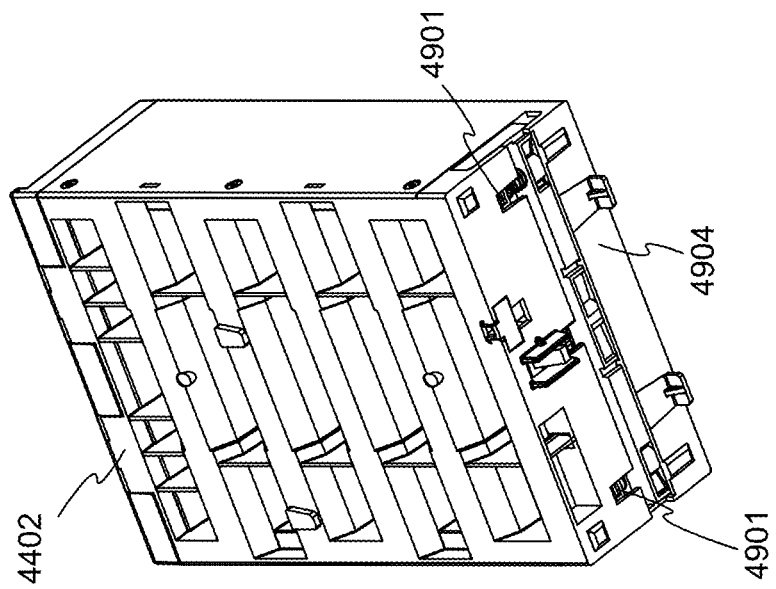
FIGS. 49A and 49B show the locations of several openings in the cassette of FIG. 47, in accordance with embodiments of the invention.
Figure 49A:
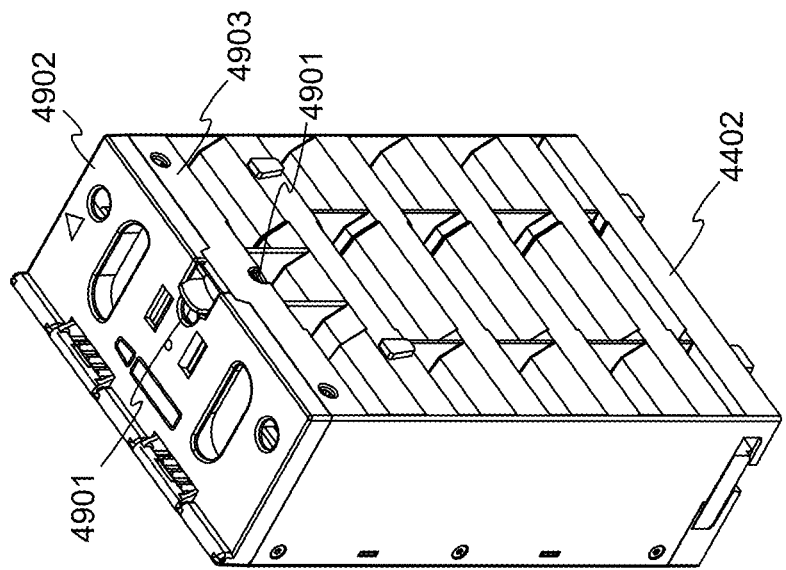
Figure 50:
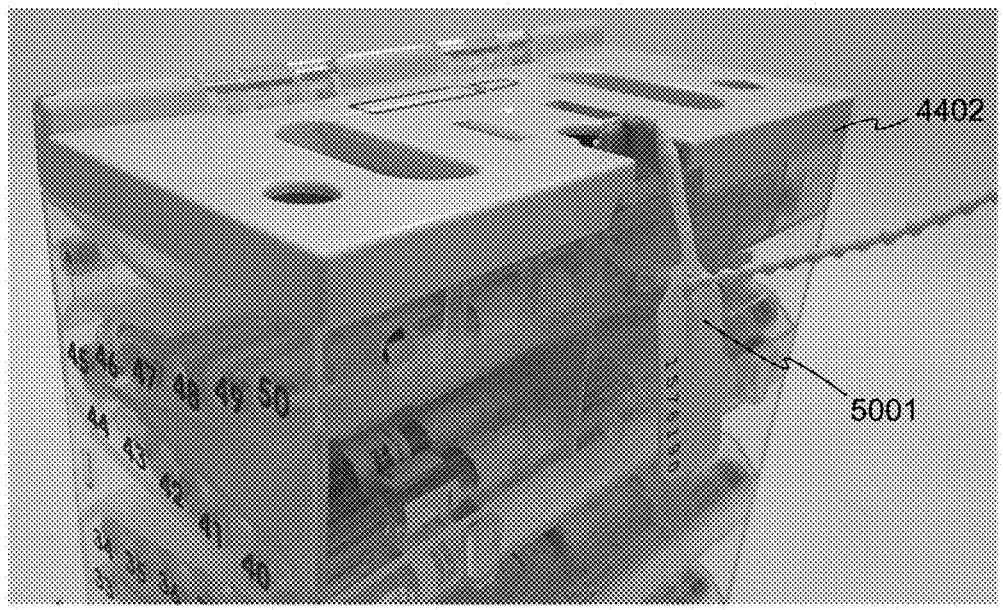
FIGS. 50 and 51 show several ties inserted into the openings shown in FIGS. 49A and 49B.
Figure 51:
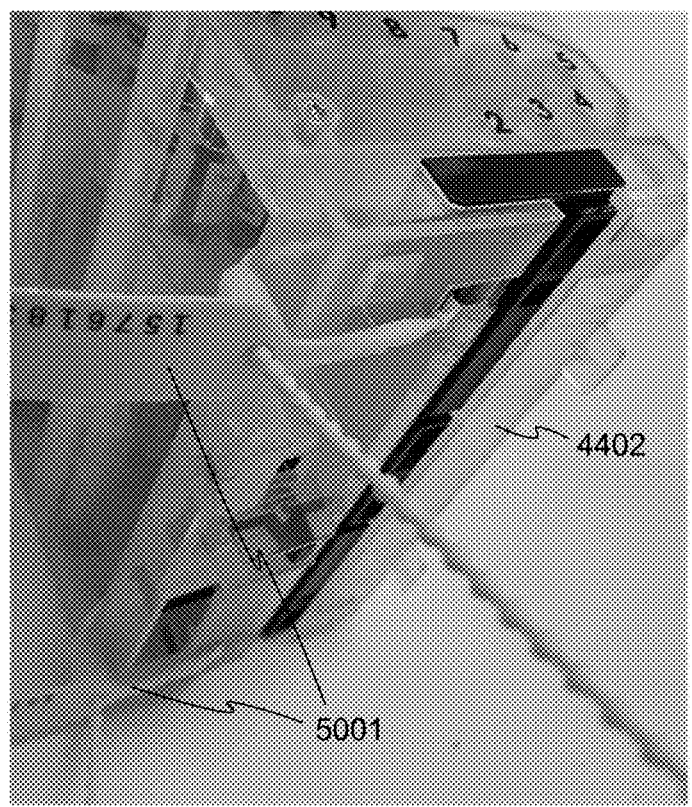

Other measures may be taken to prevent accidental or intentional diversion of items from cassette 4402. For example, as shown in FIGS. 49A and 49B, which are upper and lower oblique views of cassette 4402, openings 4901 may be provided in top 4902, side 4903, and bottom 4904 of cassette 4402, to accommodate tamper-evident ties that also disable the operation of cassette 4402. FIGS. 50 and 51 show cassette 4402 with ties 5001 installed. Ties 5001 may be, for example, plastic "zip" ties or a similar kind of tie, that is not conveniently removable without cutting the tie. Ties 5001 may be installed when cassette is filled, and not legitimately removed until cassette 4402 is ready to be installed in a drawer such as drawer 106. If cassette 4402 arrives at its destination with all of ties 5001 intact, it may be assumed that no tampering or accidental dispensing has occurred. If any of ties 5001 is missing or damaged, diversion may be suspected. When a decision is made to install cassette 5502 in a dispenser or drawer, the restock technician can cut and remove ties 5001 before installation.

Other kinds of tamper-evident mechanisms may be used as well, instead of or in addition to ties 5001.

Light Detection

In each of the embodiments described above, one or more light emitters and detectors are used to create a "light curtain" at the bottom of each dispenser, for detecting items being dispensed, or that an item may not have been dispensed when desired. Additional details of example implementations and uses for the light emitters and detectors are given below.

Figure 52:
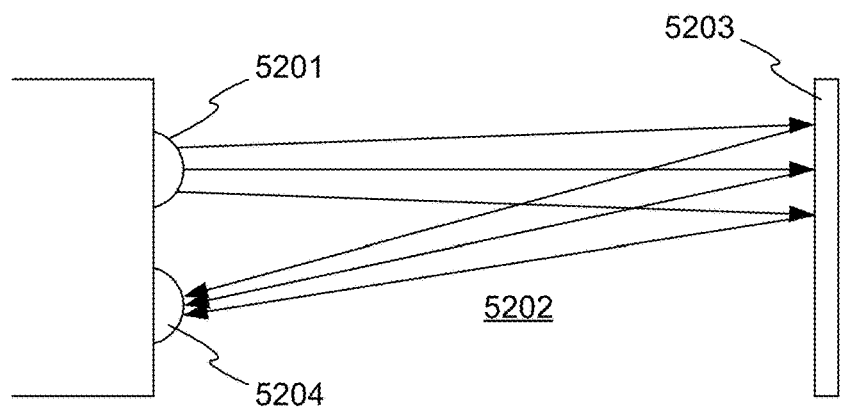
FIG. 52 schematically illustrates an arrangement of a light curtain in accordance with embodiments of the invention.

FIG. 52 schematically illustrates an arrangement of a light curtain, using only one emitter and one detector for simplicity of explanation. A light emitter 5201 emits light through space 5202 toward a surface 5203. Light emitter 5201 may be, for example, an infrared light emitting diode (LED) emitting light at a wavelength of about 940 nm, or may be another kind of light emitter. In some embodiments, emitter 5201 may be an SFH 4641 infrared LED emitter available from Osram Sylvania having offices in Wilmington, Mass., USA.

Surface 5203 may be reflective, for example a mirrored or diffuse white surface, so that some of the light reflected from surface 5203 is directed to a sensor 5204. Sensor 5204 may be, for example, a model VEMT3700F phototransistor available from Vishay Intertechnology of Malvern, Pa., USA. Sensor 5204 produces a signal indicating the intensity of light falling on it. In the configuration of FIG. 52, the travel of light from emitter 5201 to surface 5203 and back to sensor 5204 is unobstructed, so that sensor 5204 will produce a signal indicating that it is receiving light.

Figure 53:
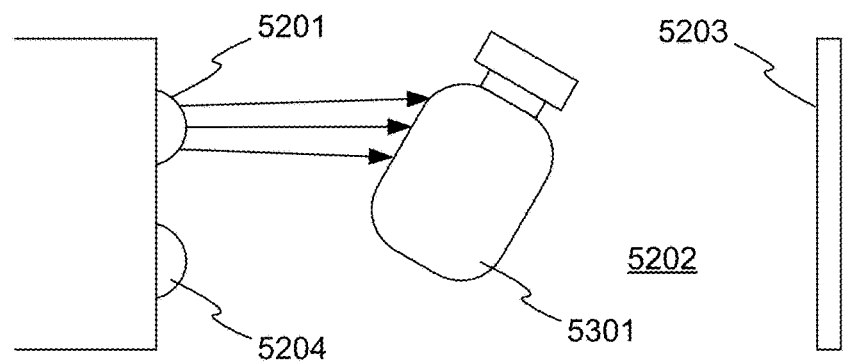
FIG. 53 shows the light curtain of FIG. 52 with the light being interrupted by a dispensed item.

When an item is dispensed through space 5202, the light is interrupted, as shown in FIG. 53. For example, vial 5301 interrupts the light emanating from emitter 5201 so that it does not reach surface 5203, and does not reflect to sensor 5204. Some light may scatter from the surface of vial 5301, but little will reach sensor 5204, and the signal produced by sensor 5204 in this state indicates that little or no light is reaching sensor 5204. In this arrangement, the dispensing of an item is indicated by a decrease in the light detected by sensor 5204.

Figure 54:
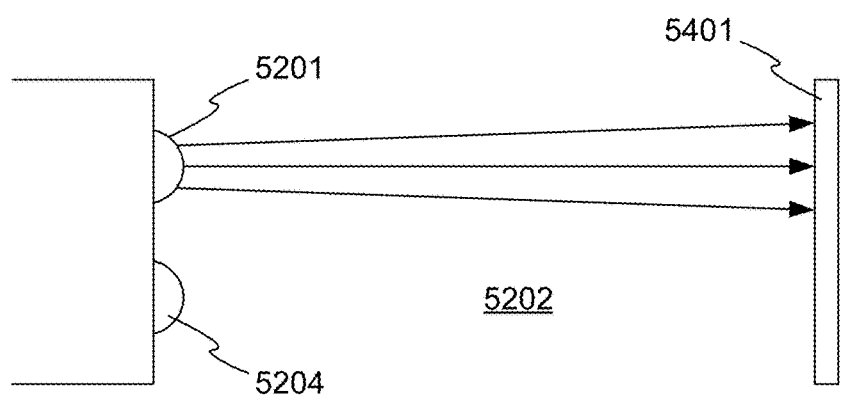
FIG. 54 schematically illustrates an arrangement of a light curtain in accordance with other embodiments of the invention.

In other embodiments, surface 5203 may be non-reflective, for example black. This arrangement may be especially useful when the items to be dispensed are themselves highly reflective. For example, FIG. 54 shows a light curtain having a black surface 5401, with no item being dispensed. Surface 5401 substantially absorbs the light hitting it from emitter 5201, and this sensor 5204 will produce a signal indicating that it is receiving little or no light.

Figure 55:
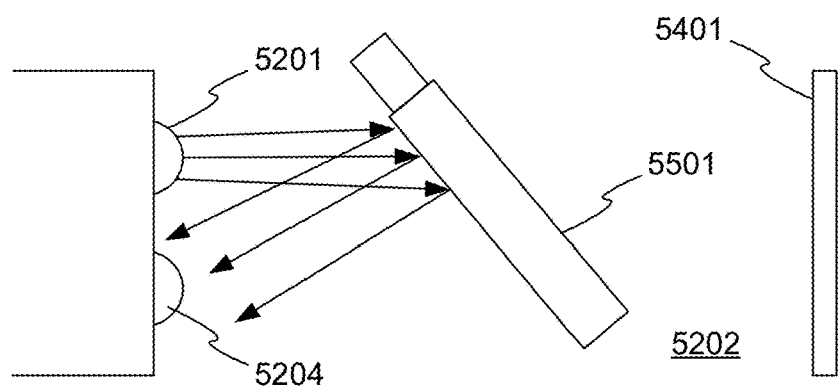
FIG. 55 shows the light curtain of FIG. 54 with the light being reflected by a dispensed item.

FIG. 55 illustrates the dispensing of an item between emitter 5201 and non-reflective surface 5401. In this example, a syringe 5501 is reflective, and scatters light toward sensor 5204, so that sensor 5204 will produce a signal indicating that it is receiving light when syringe 5501 passes through space 5202. In this arrangement, the dispensing of an item is indicated by an increase in the light detected by sensor 5204.

Figure 56:
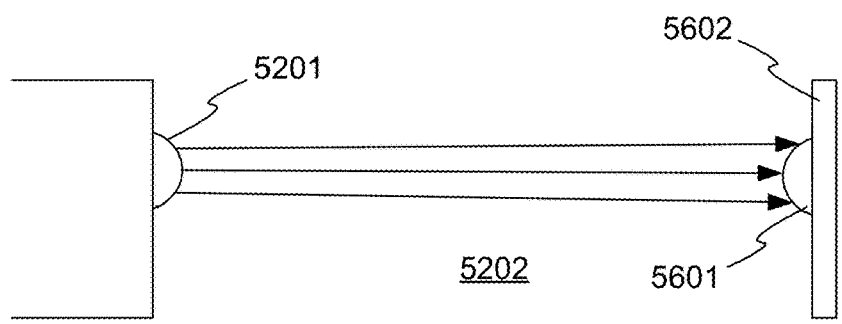
FIG. 56 schematically illustrates an arrangement of a light curtain in accordance with other embodiments of the invention.

In other embodiments, a "transmissive" light curtain may be used, that does not rely on the reflection of light for detecting dispensed items. For example, FIG. 56 shows an emitter 5201 and a receiver 5601 on an opposite side 5602 of space 5202 from emitter 5201. Receiver 5601 receives light directly from emitter 5201.

Figure 57:
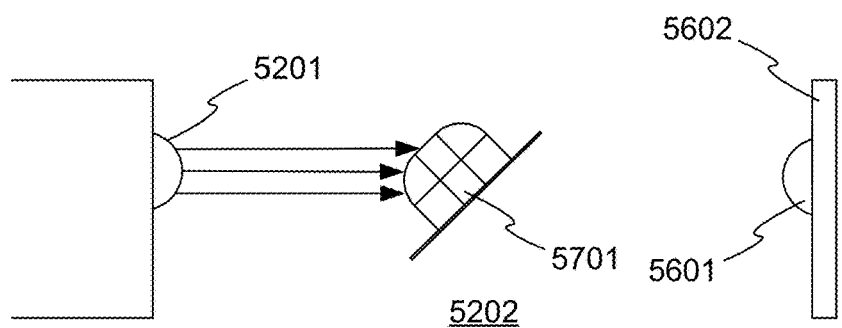
FIG. 57 shows the light curtain of FIG. 56 with the light being interrupted by a dispensed item.

FIG. 57 illustrates the dispensing of an item between emitter 5201 and receiver 5601. In this example, a blister pack 5701 interrupts the light emanating from emitter 5201 so that it does not reach receiver 5601. In this arrangement, the dispensing of an item is indicated by a decrease in the light detected by sensor 5601.

In other embodiments, a combination of these techniques may be used. For example, a sensor may be monitored to detect both increases and decreases in received light.

Figure 58:
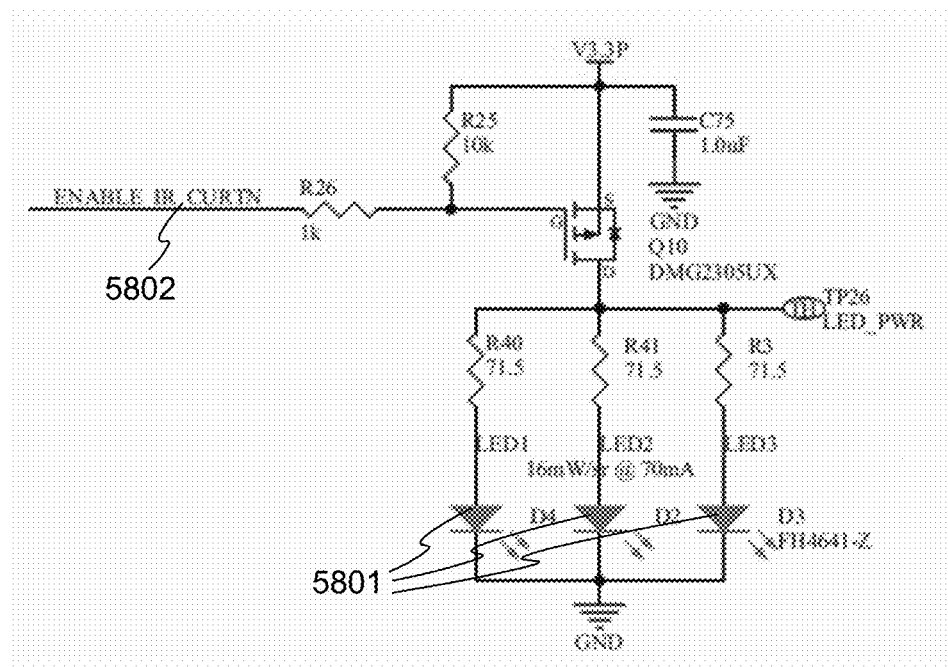
FIG. 58 shows light emitter circuitry in accordance with embodiments of the invention.
Figure 59:
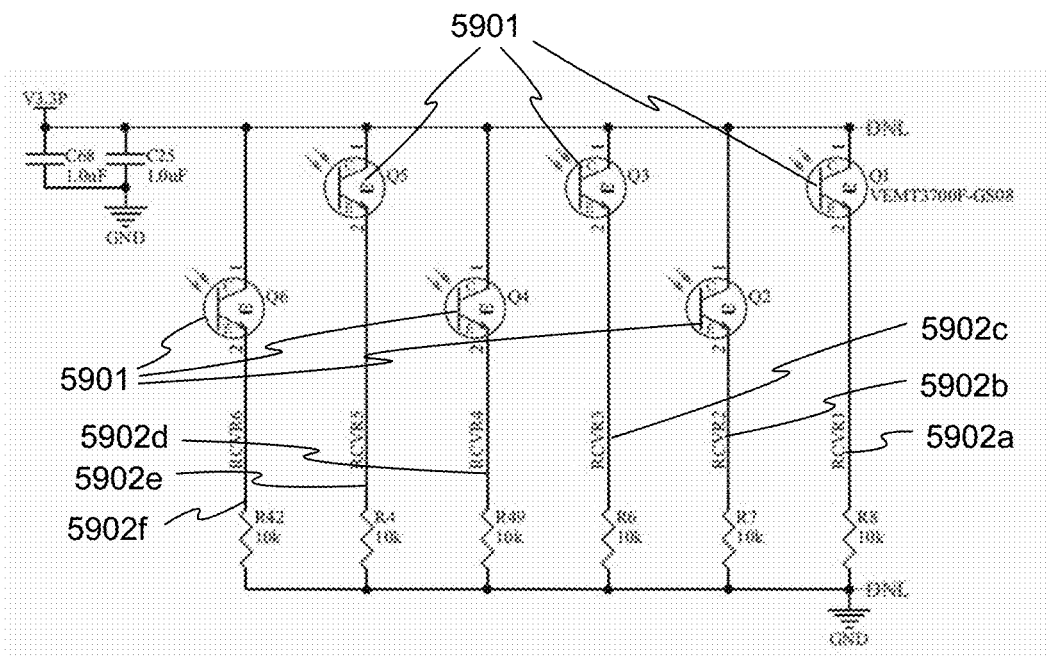
FIG. 59 shows light detection circuitry in accordance with embodiments of the invention.
Figure 60:
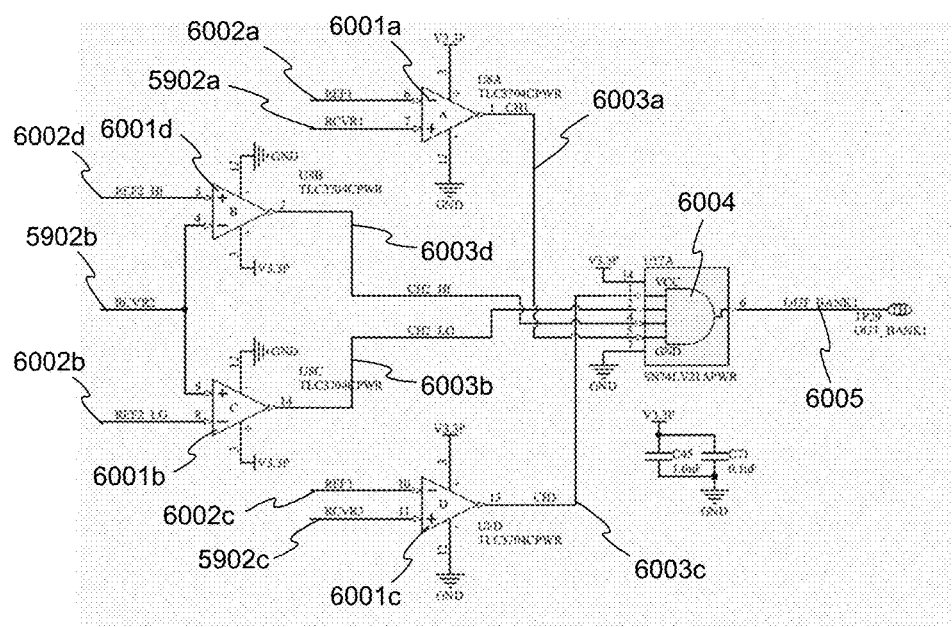
FIG. 60 shows light detection logic circuitry in accordance with embodiments of the invention.

FIGS. 58-60 show schematic diagrams of circuitry for an example system having three light emitters and six light receivers. As shown in FIG. 58, three emitters 5801 can be turned on or off, for example by a controller within cabinet 100 or within a specific dispenser, using input 5802.

As shown in FIG. 59, six light receivers in the form of phototransistors 5901 produce outputs 5902a-5902f indicating the intensity of light being received by the respective phototransistors 5901. In this example, each output is a voltage.

FIG. 60 illustrates the generation of a detection signal from the outputs 5902a-c of three of phototransistors 5901. Output 5902a is fed to a comparator 6001a, which compares the voltage of output 5902a with a first reference voltage 6002a. If output 5902a exceeds reference voltage 6002a, then output 6003a goes to a digital "high" value, but is otherwise low.

Similarly, comparator 6001c compares the voltage of output 5902c with a reference voltage 6002c, and produces output 6003c.

Output 5902b is fed to two comparators 6001b and 6001d. Comparator 6001b operates similarly to comparators 6001a and 6001c, producing a "high" output at output 5903b when the voltage of sensor output 5902b exceeds reference value 6002b. However, comparator 6001d operates in the opposite sense, comparing sensor output voltage 5902b with a high reference 6002d. Output 6003d is "high" when output 5902b is below reference voltage 6002d, but is otherwise low.

All of outputs 6003a-d are fed to a quad-input AND gate 6004, which produces a "high" detection signal 6005 only when all four of the inputs are high. That is, detection signal 6005 is high only when outputs 5902a-c exceed references 6002a-c, and output 5902b is below reference 6002d. With regard to comparators 6001c, this corresponds to the situation shown in FIG. 52, where three receivers are receiving light sufficient to exceed a threshold. With regard to the fourth comparator 6001d, reference 6002d may be set high enough that receiver output 5902b normally does not exceed it, but low enough to possibly "see" glinting reflections. The use of two different comparator senses is sometimes called "window" detection.

Detection output 6005 will normally be high, but will go low when any one or any number of comparators 6001a-d gives a low signal. Output 6005 may generate an interrupt in a processor coupled to the appropriate dispensing mechanism to signal the dispensing of an item. In other embodiments, detection signal 6005 may be polled.

The controller may watch for the detection signal immediately after commanding that an item be dispensed, to confirm proper dispensing or to detect a failure to dispense an item.

However, the controller may monitor detection signal 6005 at other times as well, to detect a detection signal not produced in conjunction with the dispensing of an item. If detection signal 6005 goes low at such a time, it may be suspected that a diversion attempt is underway, with a finger or tool being inserted into the dispensing mechanism from below. A warning signal may be generated to indicate the suspected diversion or tampering.

Receiver outputs 5902d-f may be processed in a similar way, to provide a second detection signal. Any workable number of emitters and receivers may be used, with any number triggering on a decrease of light reaching the respective receiver or triggering on an increase of light reaching the respective receiver.

For example, in a system similar to the system of FIGS. 54 and 55, using a black surface 5401 and relying on reflection from an item being dispensed for detection, most or all of the receivers may be configured to generate a detection signal upon an increase of light being received.

Any or all of the reference voltages may be settable by a controller, for calibration purposes. For example, each of the reference voltages may be the output of a respective digitally-controlled potentiometer. The references may be re-calibrated for each dispense request, for example by turning on emitters 5801 and adjusting the reference voltages to find the tripping point for each comparator 6001. Once the tripping point is found, the reference voltage may be re-adjusted to a percentage of the tripping voltage. Preferably, each reference is calibrated individually.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. It is to be understood that any workable combination of the elements and features disclosed herein is also considered to be disclosed.

The invention has now been described in detail for the purposes of clarity and understanding. However, those skilled in the art will appreciate that certain changes and modifications may be practiced within the scope of the appended claims.

What is claimed is:

1. A system for detecting items, the system comprising:
one or more light emitters directed across an opening;
one or more light receivers, each of the light receivers generating a signal indicating the intensity of light received by the respective light receiver;
a dispensing mechanism that contains one or more items to be dispensed, and is configured to cause the items to be dispensed one at a time through the opening, wherein the dispensing mechanism includes a housing for storing the items to be dispensed, and wherein the dispensing mechanism includes an actuator that moves in response to electrical signals to cause items to be dispensed from the housing;
circuitry that compares each of the signals from the one or more light receivers with a respective reference signal and generates an electrical detection signal based on the result of the comparisons, wherein the detection signal indicates one or more conditions selected from the group of conditions consisting of a) any one or any number of the one or more light receivers is producing an output signal that is below one of the reference signals, and b) any one or any number of the one or more light receivers is producing an output signal that is above one of the reference signals; and
a controller that receives the detection signal, wherein the controller is configured to:
command the dispensing of an item;
monitor the output of the circuitry for a detection signal produced in conjunction with the dispensing of the item; and
during a time when no dispensing is required, monitor the output of the circuitry for a detection signal that is not produced in conjunction with the dispensing of any item.

2. The system of claim 1, wherein the one or more light emitters are positioned to emit light toward a reflective surface, and wherein the detection signal indicates a decrease in the intensity of the light reflected from the surface and received by one or more of the one or more light receivers.

3. The system of claim 1, wherein the one or more light emitters are positioned to emit light toward a non-reflective surface, and wherein the detection signal indicates an increase in the intensity of the light received by one or more of the one or more light receivers.

4. The system of claim 1, wherein the one or more light receivers are positioned to receive light directly from the one or more light emitters, and wherein the detection signal indicates a decrease in the intensity of the light received directly by one or more of the one or more light receivers.

5. The system of claim 1, wherein at least one of the signals output by at least one of the light receivers is compared against both an upper reference signal and a lower reference signal, and wherein the detection signal is generated when the output signal exceeds the upper reference signal or falls below the lower reference signal.

6. The system of claim 1, wherein the controller is configured to generate a warning upon receipt of a detection signal that is not produced in conjunction with the dispensing of any item.

7. The system of claim 6, wherein the warning indicates the possibility of a diversion attempt.

* * * * *